United States Patent
Penn, IV et al.

(10) Patent No.: US 11,871,969 B2
(45) Date of Patent: Jan. 16, 2024

(54) SYSTEM AND METHOD FOR OSSEOUS RECONSTRUCTION AND REPAIR AND IMPLANT DEVICE

(71) Applicant: ACUSTITCH, LLC, Orlando, FL (US)

(72) Inventors: John N. Penn, IV, Orlando, FL (US); John M. Menezes, Las Vegas, NV (US)

(73) Assignee: ACUSTITCH, LLC, Orlando, FL (US)

( * ) Notice: Subject to any disclaimer, the term of this patent is extended or adjusted under 35 U.S.C. 154(b) by 28 days.

(21) Appl. No.: 17/685,832

(22) Filed: Mar. 3, 2022

(65) Prior Publication Data

US 2022/0387086 A1    Dec. 8, 2022

Related U.S. Application Data

(60) Provisional application No. 63/155,908, filed on Mar. 3, 2021.

(51) Int. Cl.
*A61B 17/80* (2006.01)
*A61B 17/88* (2006.01)
(Continued)

(52) U.S. Cl.
CPC ...... *A61B 17/8009* (2013.01); *A61B 17/8023* (2013.01); *A61B 17/8071* (2013.01);
(Continued)

(58) Field of Classification Search
CPC .......... A61B 2017/681; A61B 17/8004; A61B 17/8009; A61B 17/8023; A61B 17/8061;
(Continued)

(56) References Cited

U.S. PATENT DOCUMENTS

| | | |
|---|---|---|
| 2,026,266 A | 12/1935 | Booty |
| 4,119,092 A | 10/1978 | Gil |

(Continued)

FOREIGN PATENT DOCUMENTS

| | | |
|---|---|---|
| EP | 1764051 | 3/2007 |
| EP | 2494929 | 5/2012 |

(Continued)

*Primary Examiner* — Larry E Waggle, Jr.
*(74) Attorney, Agent, or Firm* — Terry M. Sanks, Esq.; Beusse Sank, PLLC

(57) ABSTRACT

An implant device includes a connection bridge to cause retraction or distraction of first and second bone segments. The connection bridge overlaps a surface of the segments and exerts a force to one of the first and second bone segments by translation motion of connection bridge. The bridge includes a first insertion structure mountable to the first segment and has at least one rack. An internal repositioning tool has a pinion to engage the rack causing the motion. A locking mechanism selectively locks the motion of the repositioning tool. A second insertion structure mounts to the second segment or a third bone segment between the first and second segments. The second structure includes a housing to house at least one of the pinion and the lock mechanism and receive a portion of the at least one rack to engage the at least one the pinion and the lock mechanism.

19 Claims, 41 Drawing Sheets

(51) Int. Cl.
*A61B 17/68* (2006.01)
*A61B 17/56* (2006.01)

(52) U.S. Cl.
CPC ........ *A61B 17/88* (2013.01); *A61B 2017/564* (2013.01); *A61B 2017/681* (2013.01)

(58) Field of Classification Search
CPC .. A61B 17/8071; A61B 17/8076; A61B 17/88
See application file for complete search history.

(56) References Cited

U.S. PATENT DOCUMENTS

| | | | |
|---|---|---|---|
| 5,129,903 A * | 7/1992 | Luhr | A61B 17/8004 606/282 |
| 5,672,177 A | 9/1997 | Seldin | |
| 5,700,263 A | 12/1997 | Schendel | |
| 6,126,660 A | 10/2000 | Dietz | |
| 6,277,124 B1 | 8/2001 | Haag | |
| 6,454,778 B2 | 9/2002 | Kortenbach | |
| 6,692,503 B2 | 2/2004 | Foley et al. | |
| 6,916,320 B2 | 7/2005 | Michelson | |
| 6,969,398 B2 * | 11/2005 | Stevens | A61B 17/8009 606/217 |
| 7,011,658 B2 * | 3/2006 | Young | A61B 17/7077 606/90 |
| 7,041,105 B2 | 5/2006 | Michelson | |
| 7,090,676 B2 | 8/2006 | Huebner et al. | |
| 7,097,645 B2 | 8/2006 | Michelson | |
| 7,112,202 B2 | 9/2006 | Michelson | |
| 7,211,093 B2 | 5/2007 | Sauer et al. | |
| 7,338,502 B2 | 3/2008 | Rosenblatt | |
| 7,537,604 B2 | 5/2009 | Huebner | |
| 7,862,572 B2 | 1/2011 | Meade et al. | |
| 7,875,033 B2 | 1/2011 | Richter et al. | |
| 7,993,354 B1 | 8/2011 | Brecher et al. | |
| 8,062,296 B2 | 11/2011 | Orbay et al. | |
| 8,100,922 B2 | 1/2012 | Griffith | |
| 8,162,996 B2 | 4/2012 | Schelling | |
| 8,167,918 B2 | 5/2012 | Strnad et al. | |
| 8,172,884 B2 | 5/2012 | Bouman | |
| 8,211,143 B2 | 7/2012 | Stefanchik et al. | |
| 8,257,403 B2 | 9/2012 | Den Hartog et al. | |
| 8,257,406 B2 | 9/2012 | Kay et al. | |
| 8,636,738 B2 | 1/2014 | McClintock et al. | |
| 8,709,021 B2 | 4/2014 | Chu et al. | |
| 8,764,770 B2 | 7/2014 | Moon et al. | |
| 8,771,295 B2 | 7/2014 | Chu | |
| 8,834,533 B2 | 9/2014 | Michelson | |
| 8,858,604 B2 | 10/2014 | Biyani et al. | |
| 9,044,220 B2 | 6/2015 | Chu | |
| 9,089,262 B2 | 7/2015 | Hashiba | |
| 9,211,197 B2 | 12/2015 | Baynham | |
| 9,241,750 B2 | 1/2016 | Bush, Jr. et al. | |
| 9,339,267 B2 | 5/2016 | Dreyfuss et al. | |
| 9,375,212 B2 | 6/2016 | Martin et al. | |
| 9,486,250 B2 | 11/2016 | Altarac et al. | |
| 9,554,793 B2 | 1/2017 | Lane et al. | |
| 9,724,089 B1 | 8/2017 | Martin et al. | |
| 9,737,295 B2 | 8/2017 | Ichikawa et al. | |
| 9,770,272 B2 | 9/2017 | Thoren et al. | |
| 9,775,600 B2 | 10/2017 | Brecher et al. | |
| 9,775,652 B2 * | 10/2017 | Altarac | A61B 17/7059 |
| 9,788,830 B2 | 10/2017 | Martin et al. | |
| 9,888,914 B2 | 2/2018 | Martin et al. | |
| 9,925,061 B2 | 3/2018 | Baynham | |
| 9,943,348 B2 | 4/2018 | Schelling | |
| 9,962,204 B2 | 5/2018 | Mirghasemi et al. | |
| 10,004,490 B2 | 6/2018 | Martin et al. | |
| 10,022,120 B2 | 7/2018 | Martin et al. | |
| 10,159,515 B2 | 12/2018 | Ehmke et al. | |
| 10,292,698 B2 | 5/2019 | Meade | |
| 10,463,409 B2 | 11/2019 | Castaneda et al. | |
| 10,478,237 B2 | 11/2019 | Silva et al. | |
| 10,582,958 B2 | 3/2020 | Wotton | |
| 10,603,031 B2 | 3/2020 | Sauer | |
| 10,660,677 B2 | 5/2020 | Cummins et al. | |
| 10,709,437 B2 | 7/2020 | Martin et al. | |
| 2002/0161374 A1 | 10/2002 | Cohen et al. | |
| 2010/0076444 A1 | 3/2010 | Staehler et al. | |
| 2011/0319939 A1 | 12/2011 | Kretzer et al. | |
| 2012/0209271 A1 | 8/2012 | Cohen et al. | |
| 2015/0196396 A1 * | 7/2015 | Thomas | A61F 2/28 623/23.47 |
| 2019/0314088 A1 * | 10/2019 | Kemper | A61B 17/80 |
| 2020/0205982 A1 | 7/2020 | Chin et al. | |

FOREIGN PATENT DOCUMENTS

| | | |
|---|---|---|
| EP | 2370002 | 7/2018 |
| EP | 3357433 | 10/2019 |
| WO | 2006023870 | 3/2006 |
| WO | 2014040369 | 3/2014 |

* cited by examiner

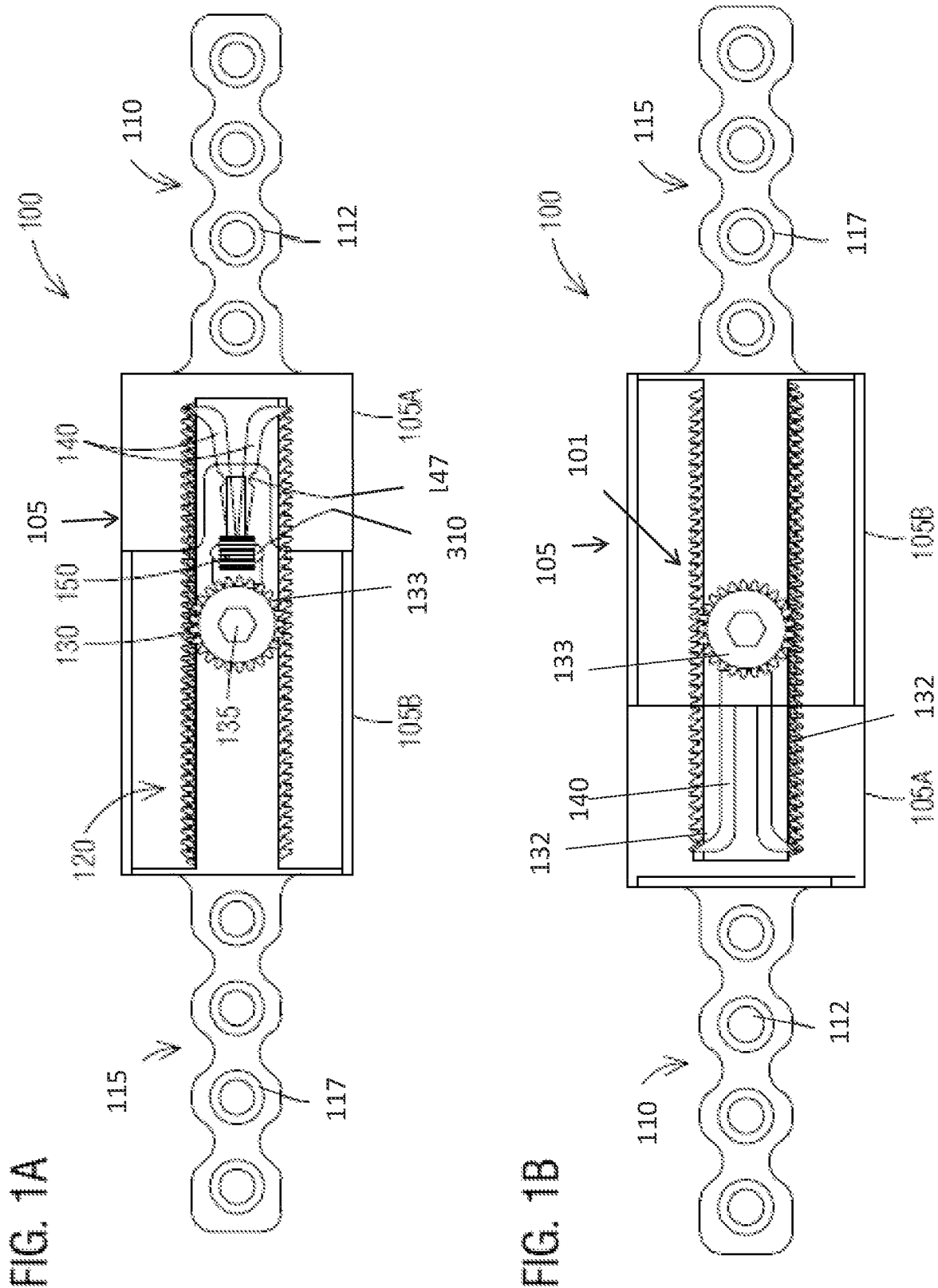

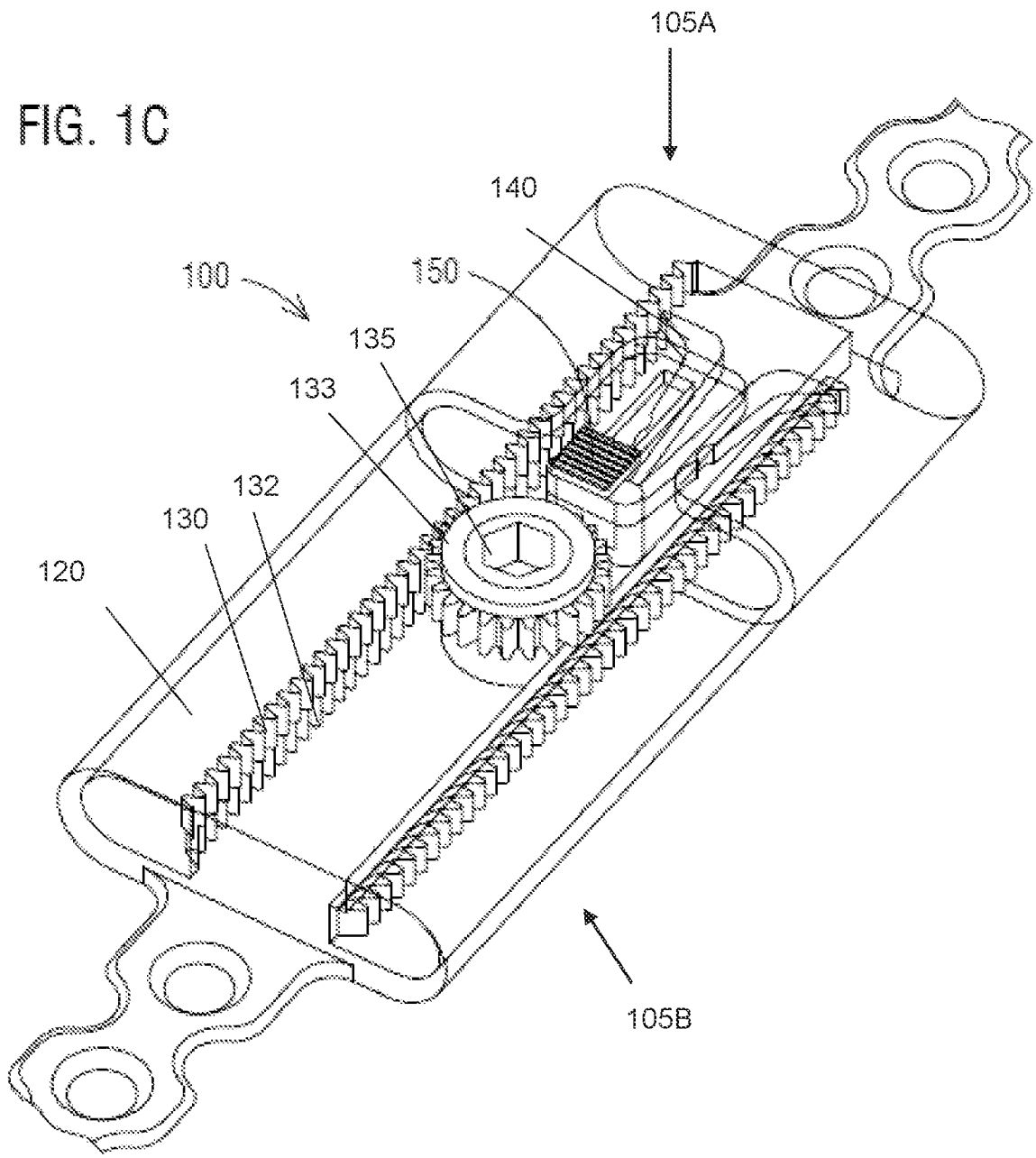

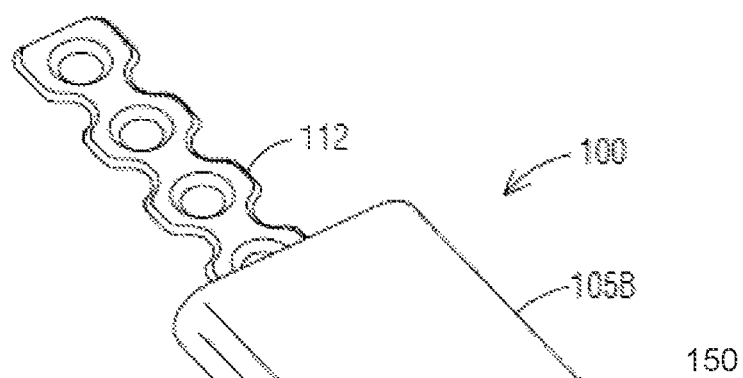
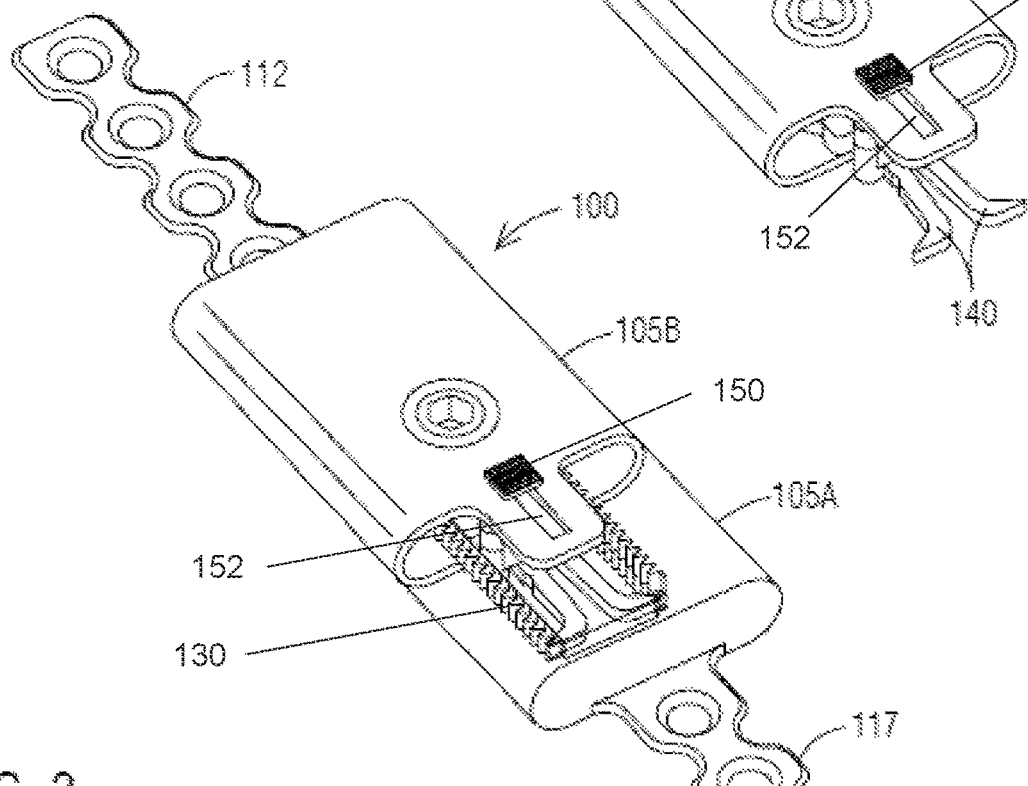
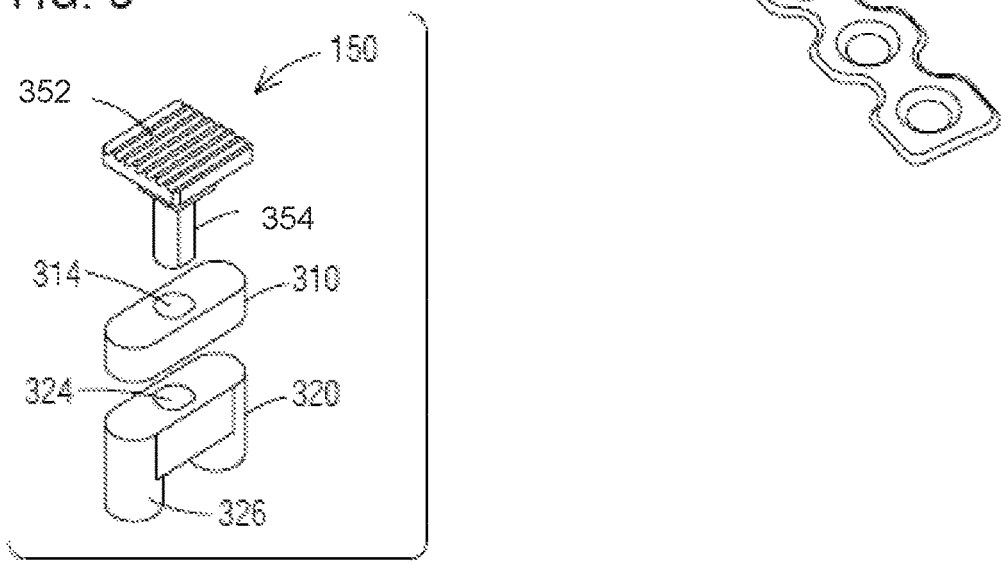

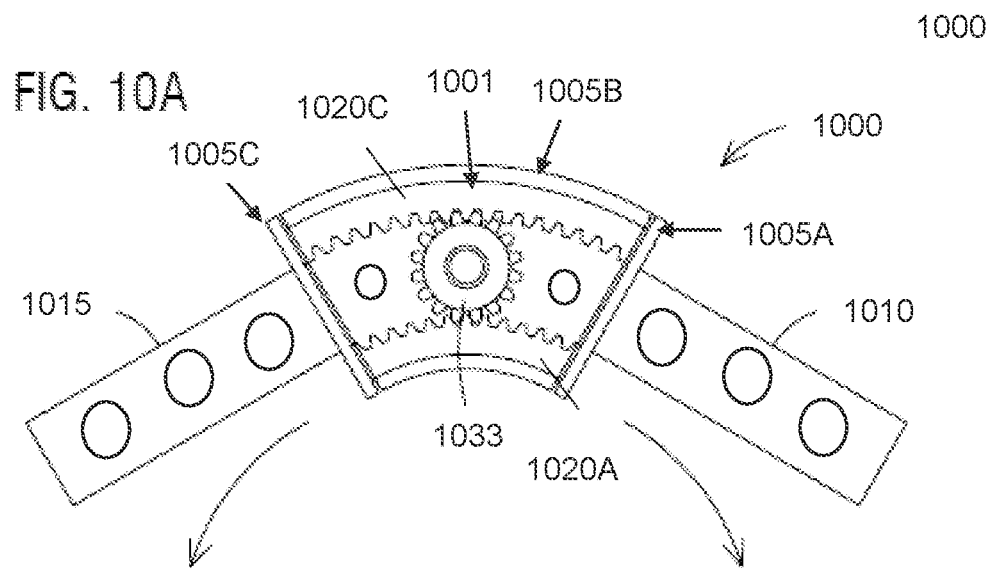
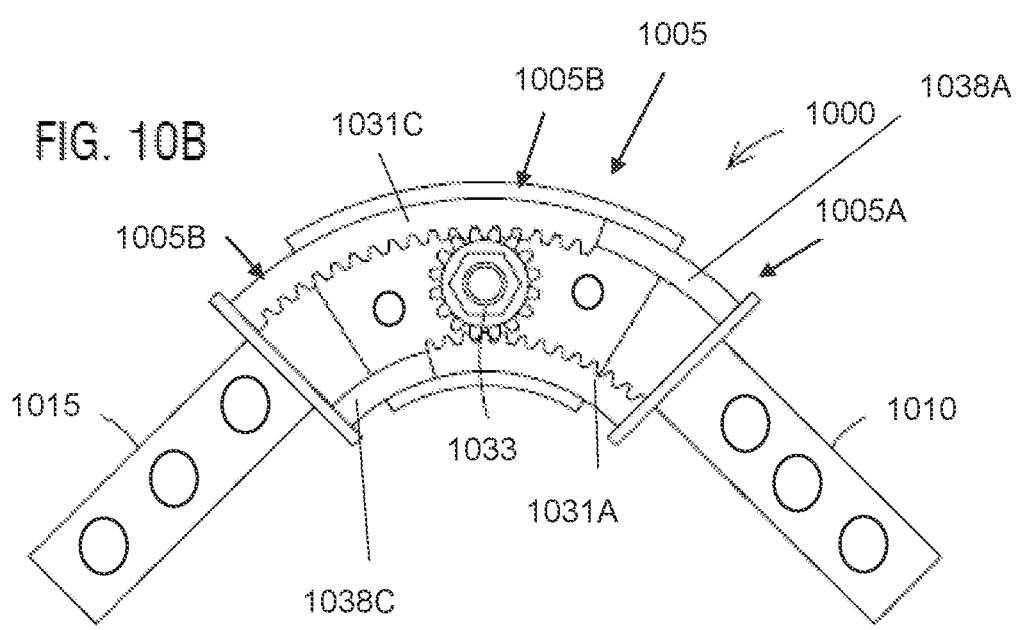

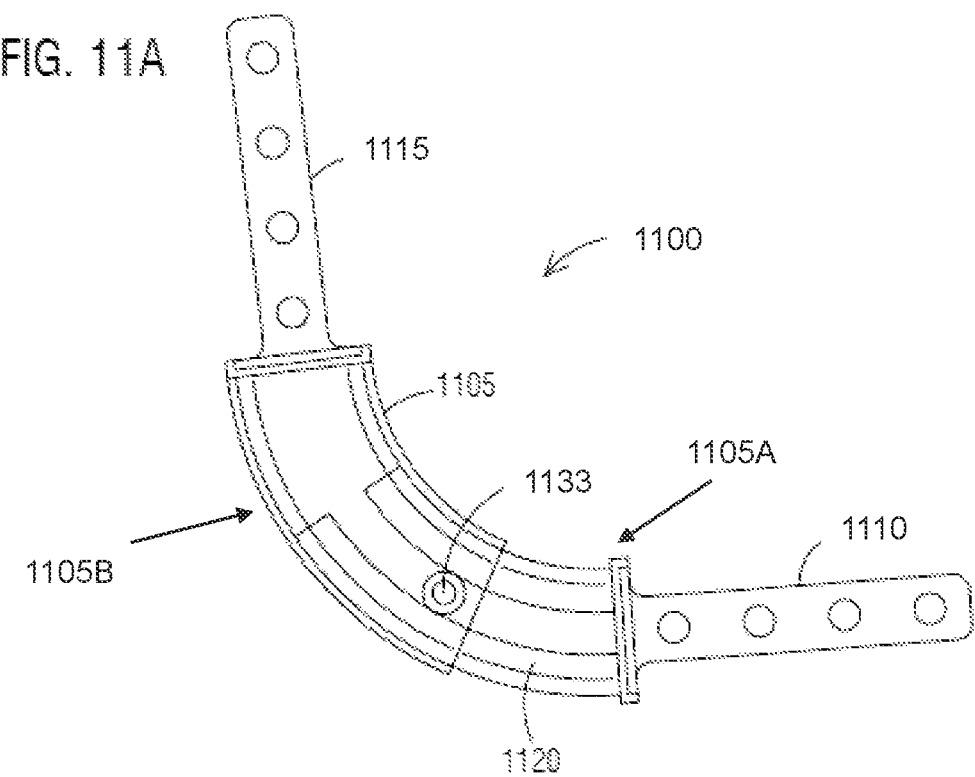
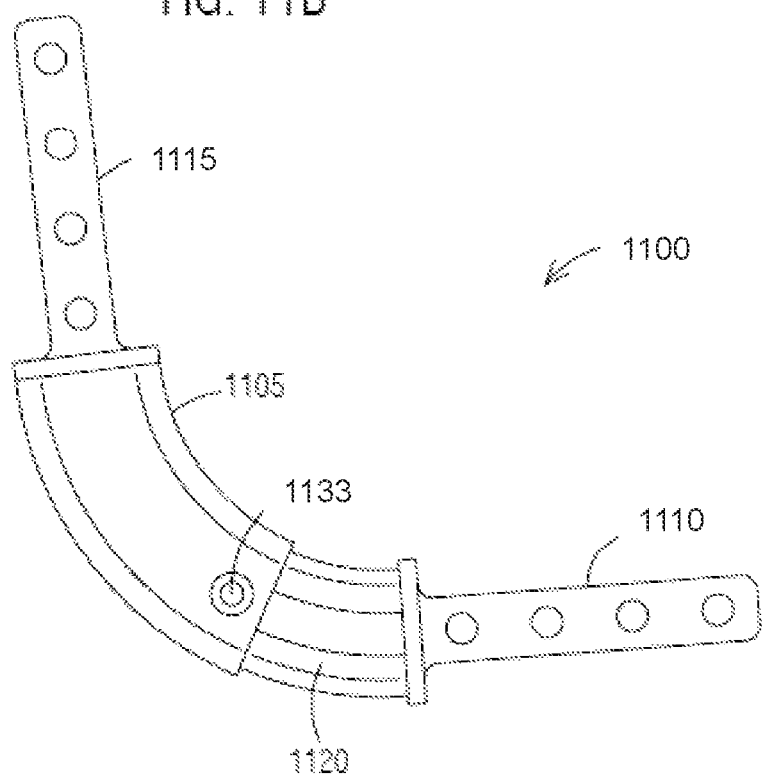

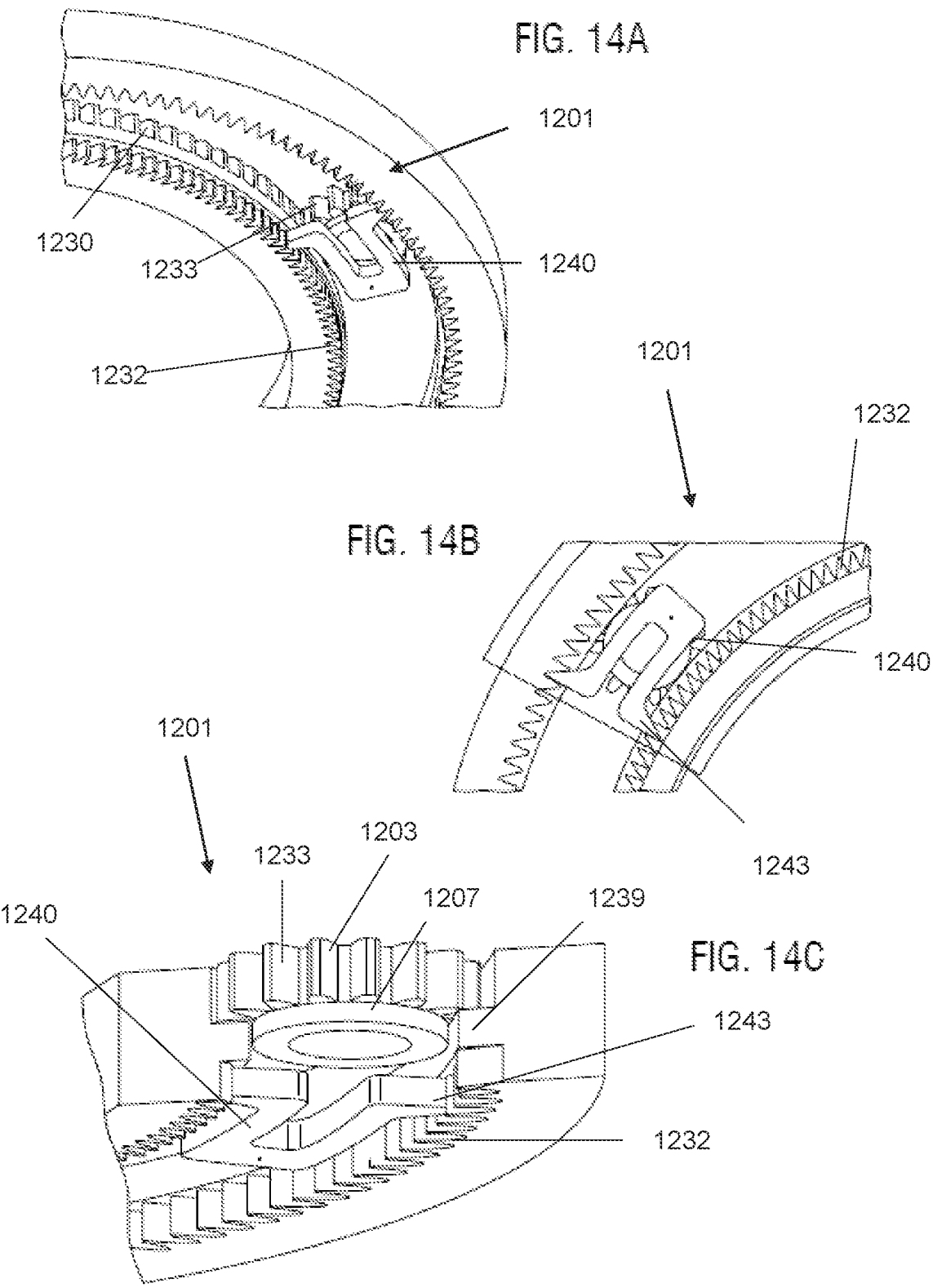

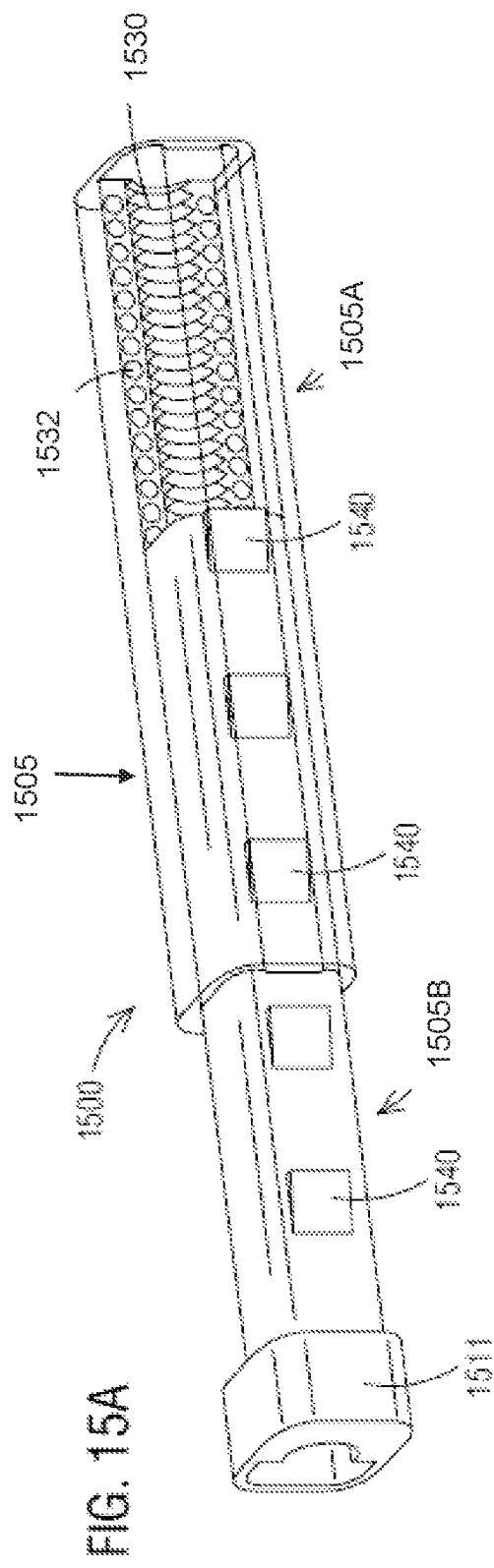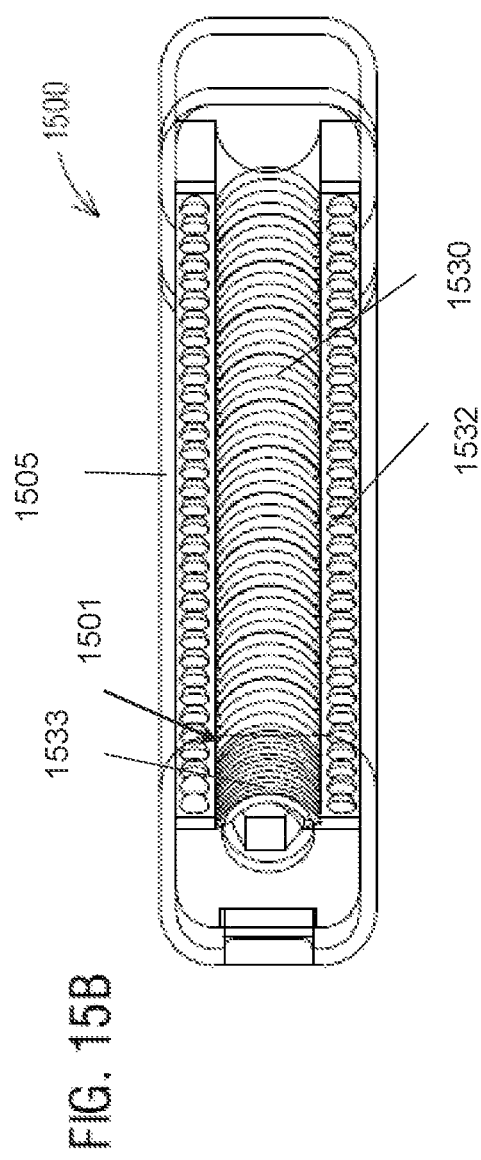

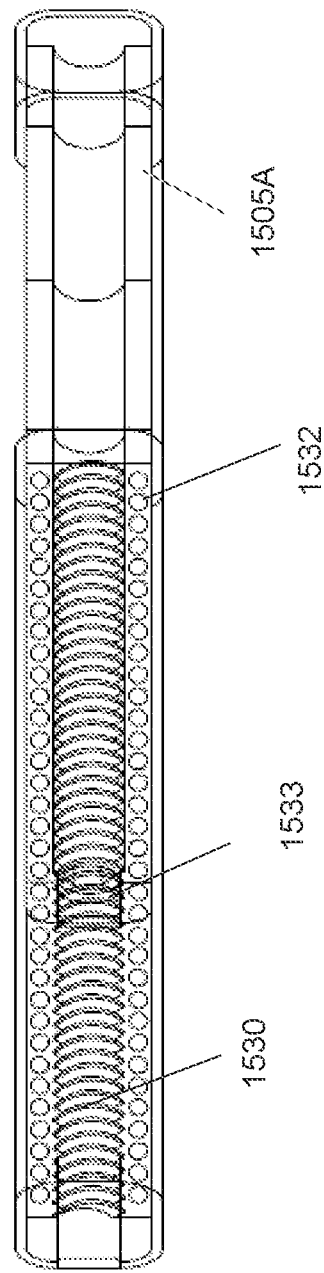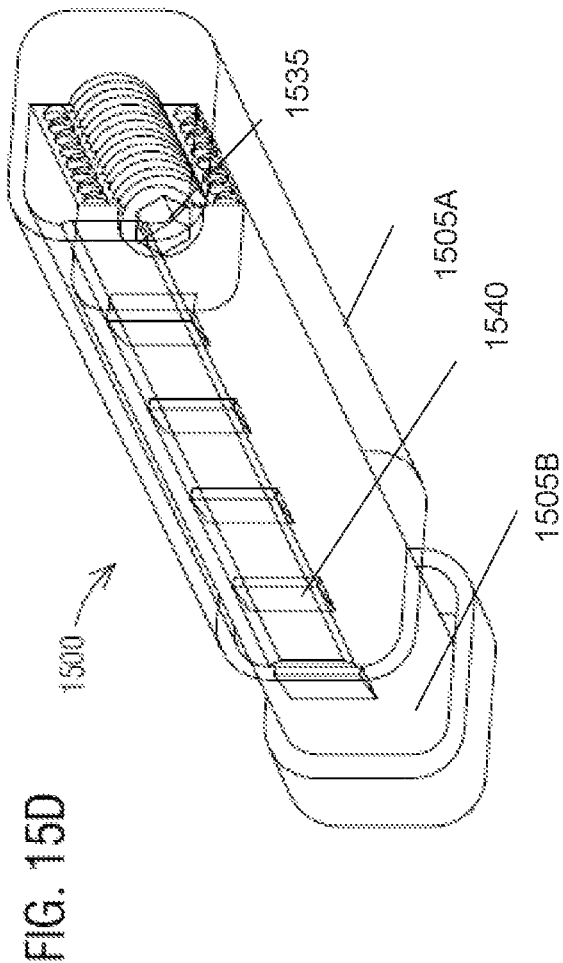

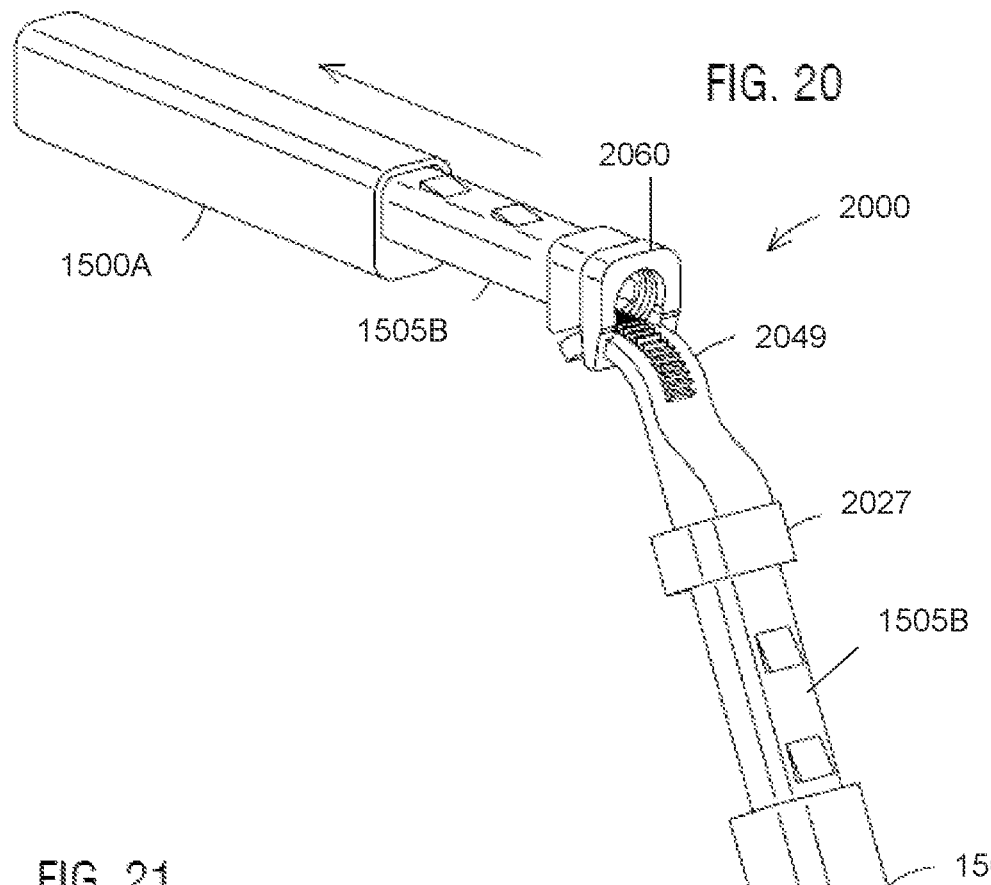
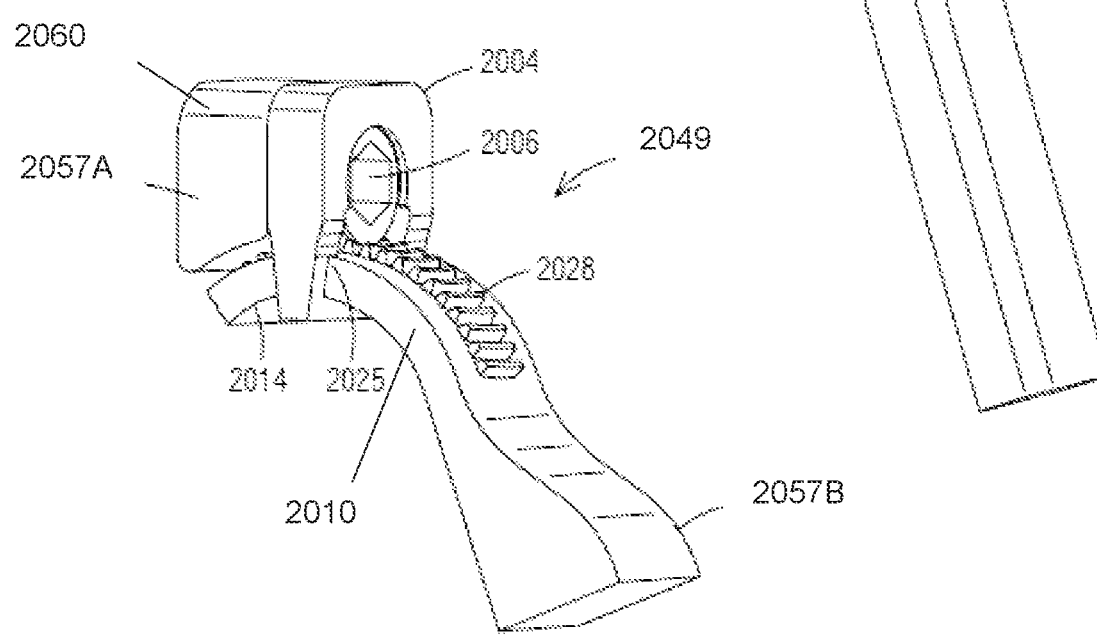

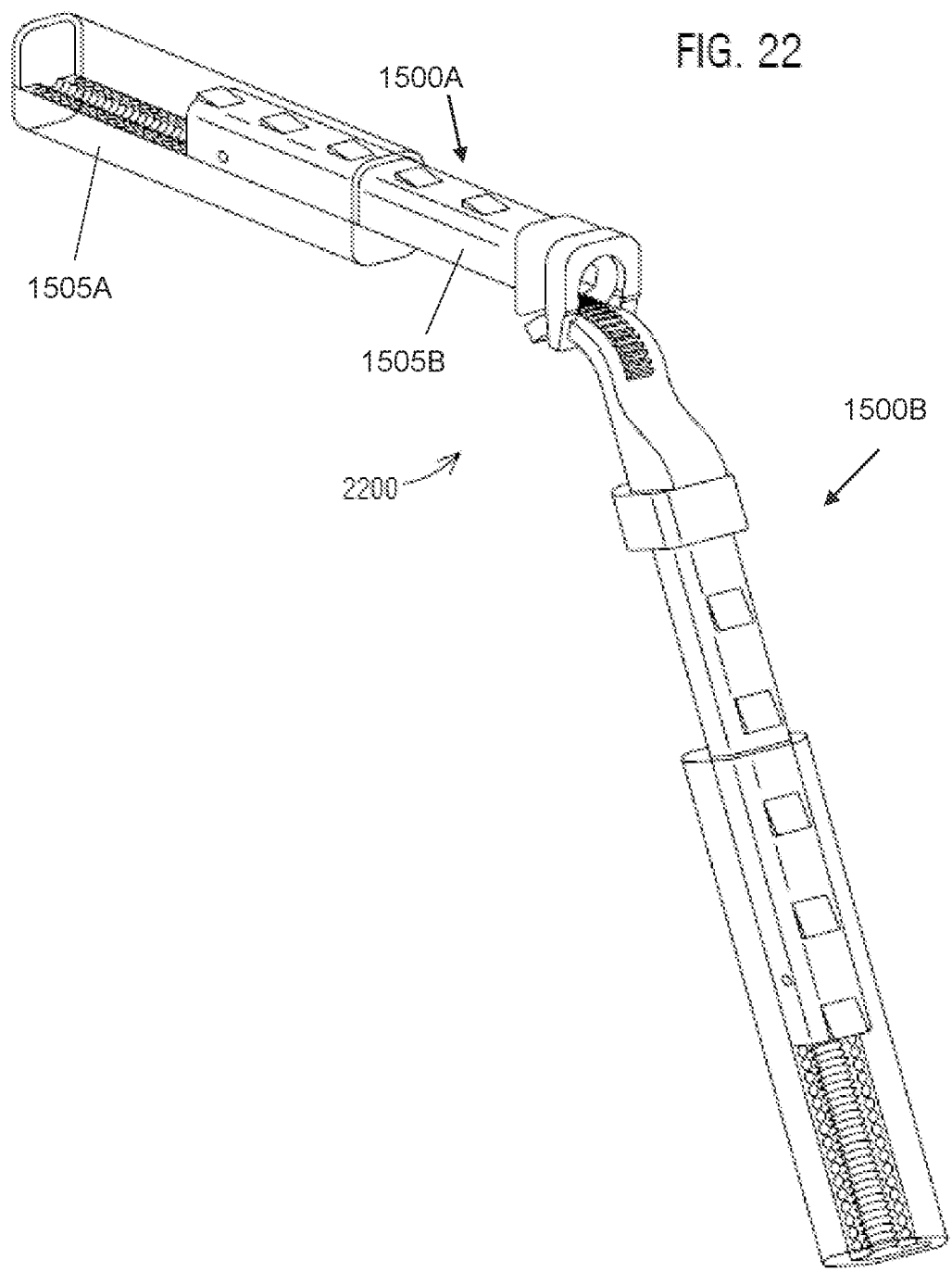

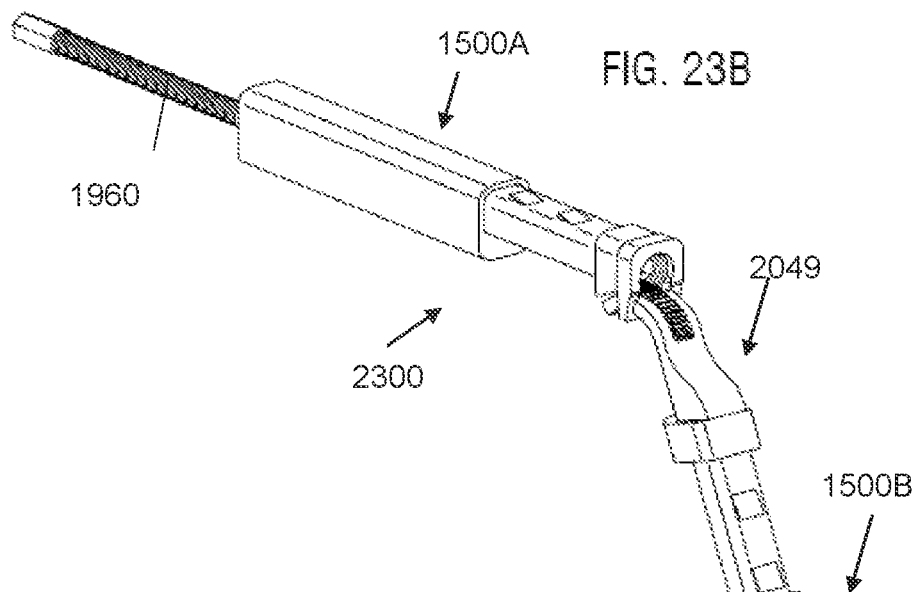
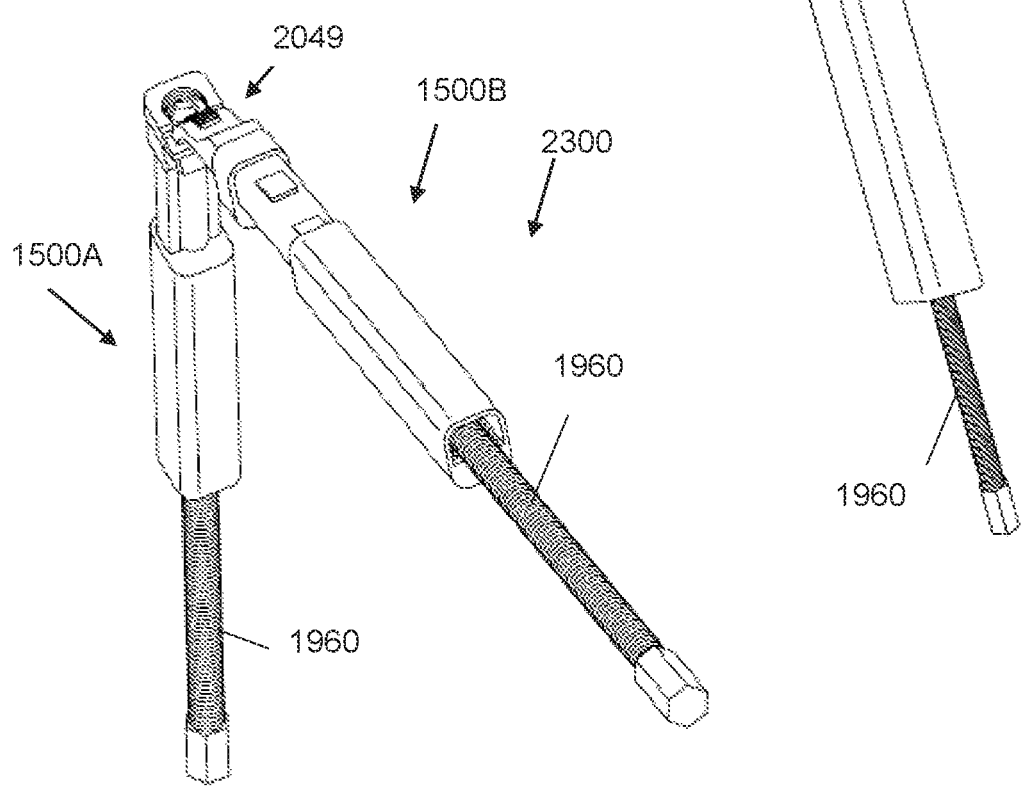

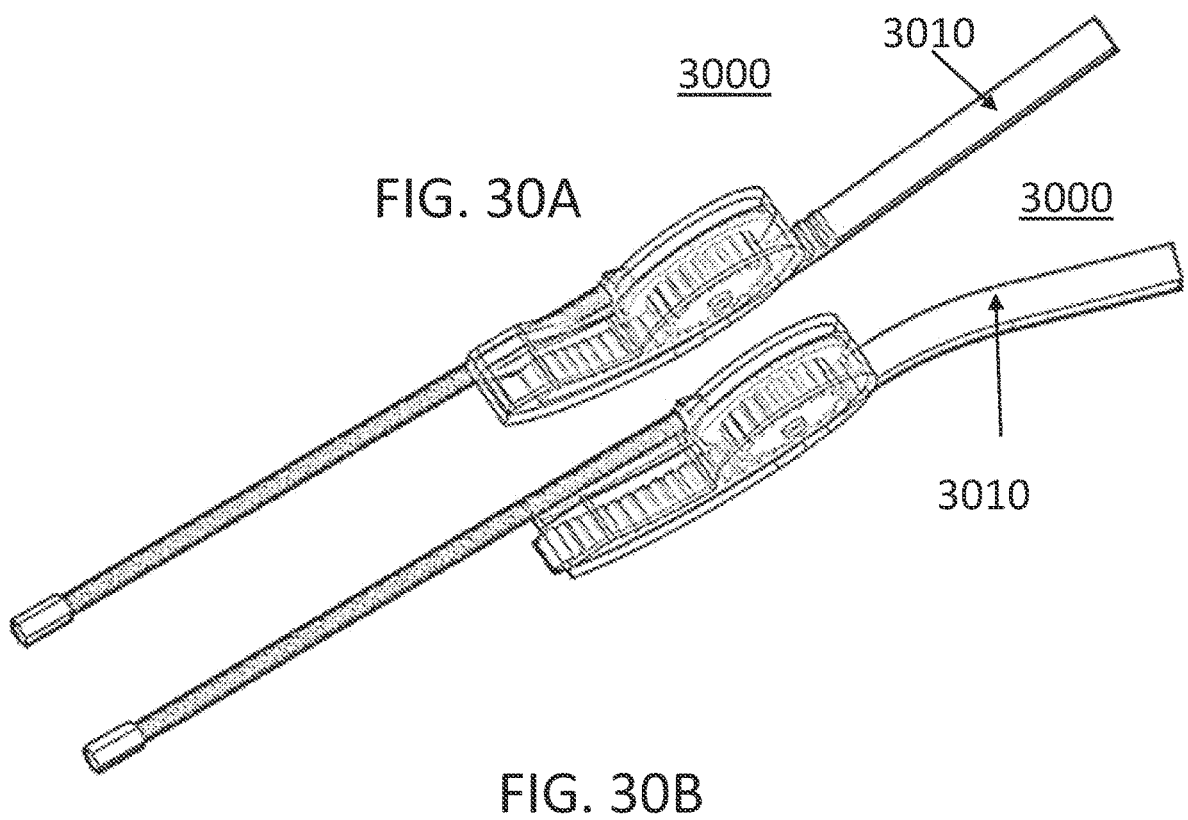

SYSTEM AND METHOD FOR OSSEOUS RECONSTRUCTION AND REPAIR AND IMPLANT DEVICE

CROSS-REFERENCE TO RELATED APPLICATIONS

This application claims priority benefit of U.S. Provisional Application No. 63/155,908 filed Mar. 3, 2021, titled "SYSTEM AND METHOD FOR OSSEOUS RECONSTRUCTION AND REPAIR," which is incorporated herein by reference.

BACKGROUND

Bones are rigid structures that provide architectural support for the body. At the tissue level, bones are an intricate combination of mineralized connective tissue, bone marrow, endosteum, periosteum, blood vessels and nerves.

There are two types of bone, cortical and trabecular, which contribute to bone structure and strength. Cortical bone has tightly compacted rigid outer walls and has a porosity between 5-10%. Cortical bone accounts for approximately 80% of adult bone mass. Trabecular bone is porous and less regular with porosity ranging between approximately 50-0%. Trabecular bones account for the remaining approximate 20% of adult bone mass. These qualities impart a balance between the skeleton's ability to resist excessive strain while providing adequate elasticity to allow it to absorb energy. The difference is important to note as it is the denser cortical bone to which fixation systems are attached securely.

Fractures, defined as a crack or break in a bone, typically occur due to excessive force being applied to the bone. There are over one million bone fracture cases in the United States each year. As a non-limiting example, trauma cases such as car accidents, falls, gunshot wounds, sports collisions, battle wounds, and others have existed throughout history. Trauma may require reconstruction and other forms of surgical repairs to address complex injuries. These repairs may involve both hard fractures (fractured bone) and soft-tissue fractures (lacerated or crushed skin and/or muscle). Such an injury is a major cause of morbidity and mortality throughout the life course, and the resultant financial burden placed on global health economies is large, generally in excess of tens of billions of dollars each year.

In contrast, an osteotomy is a surgery involving the planned/deliberate creation of a fracture or cut of the bone to facilitate the change of its shape or position for purposes of reconstruction. Reconstruction can include, but is not limited to, the designed shortening, lengthening, reshaping, and/or repositioning of a bone or segment of bone. The purposes of reconstruction can be a secondary surgery for a deformity due to trauma-caused bone fracture involving a subsequent non-union or mal-union of the fragments. Additionally, they can include cases with a need for bone lengthening/grafting to optimize form and/or function associated with congenital or developmental conditions such as hemi facial macrosomia or scoliosis.

Fractures have a variety of patterns. They include a greenstick fracture which is an incomplete fracture where the broken bone is not completely separated; a transverse fracture where the break is in a straight line across the bone; a spiral fracture where the break spirals around the bone which is common in a twisting injury; an oblique fracture where a diagonal break occurs across the bone; a compression fracture where the bone is crushed, causing the broken bone to be wider or flatter in appearance; a comminuted fracture where the break is in three or more pieces and fragments are present at the fracture site; and a segmental fracture where the same bone is fractured in two places, so there is a "floating" segment of bone.

The basic principles of internal bone fixation or reconstruction require a knowledge of both hard tissues such as bone as well as the surrounding soft tissues such as blood vessels, nerves, tendons and joints. In facial fractures, for example, approaches to repair are limited by the need to preserve, with as little scarring as possible, the critical anatomic elements of the skin and facial anatomy. In general, there is a movement toward minimally invasive techniques which require less exposure of the bone and the use of fewer and smaller incisions to facilitate rapid healing and reduce scarring.

There are several steps involved in bone fracture repair or reconstruction. One step is repositioning (reduction or distraction) the bone segments to create the needed spatial/anatomical relationships. Another step is to fix/stabilize/strengthen the repositioned structure. The repositioning and fixation steps are often accomplished with the use of a variety of fixation systems. Most use elongated plates that are positioned and attached across the intended/repositioned gap between adjacent bones or bone fragments. The repositioning of the bone segments into a restored anatomic relationship and stabilization allows the patient to heal and reestablish both form and function. A critical aspect of any surgical approach, whether open or minimally invasive, is the preservation of adjacent structures including muscles, tendons, nerves and as much as possible the periosteum (the thin layer around with bone which supplies healing osteoblasts).

In long bones, because they are force-bearing structures, the type of stabilization is also important. The degree of stabilization is different for each method with the spectrum of low to high stability ranging from casting to external fixation to bridge plating of the cortical bone to intramedullary nail (only possible in long bones with a large marrow space). Compression plating and lag screws are also at the top in terms of rigidity, but compression plating, in particular, has issues with being unable to control the degree of compression with over-compression impairing healing.

According to the inventors, due to a lack of inventiveness and the wide variety of bone fracture repairs and reconstructions, there has not been discovered any single prior art fixation system that is flexible, efficient and effective for use in the majority of situations. As noted above, many prior art systems involve some form of a one-piece, elongated plate that is commonly installed using these steps in general: (a) the bone segment is either brought out to length or reduced to establish the normal or desired anatomic shape; and (b) while maintained in this desired position, holes for screws are drilled into the bone, and screws are inserted to attach the plate to the bone segments and stabilize them.

The combination of steps is difficult, time consuming. and often cannot be accomplished while maintaining the exact intended, repositioned bone fragment spatial arrangement. Any loss of the desired spatial arrangement can lead to functional and/or healing issues for the patient. If the steps are performed through minimal incisions or through approaches that are limited by local anatomy, such as in the facial skeleton, this adds additional technical challenges.

Most prior art fixation systems do not provide adjustment of bone position once the fixation screws have attached the plate(s) to the bone(s). Those that do typically provide a linear repositioning/reduction adjustment which may not be adequate for optimal approximation of the fragmented bone. The prior art fixation systems are for very specific applications and also require substantial surgical training time to acquire even minimal proficiency.

Fixation systems can be made of corrosion-resistant metal or other materials both non-resorbable (permanent), and resorbable. The most common non-resorbable material is titanium as it is strong, light weight, and does not illicit a biological response. Titanium can further be configured in either solid or porous structures. The porous structures can be combined with biologics or bone graft tissue. Other materials that can be used include chromium cobalt, ceramic or hydroxyapatite. Hydroxyapatite (HA) is a biologically compatible calcium composite such as calcium phosphate mineral with the chemical formula $Ca_{10}(PO_4)_6(OH)_2$. HA-like compounds compose approximately 65% of bone, making them an appealing option for a synthetic bone composite.

Resorbable (absorbable) fixation systems have been developed as well. These are generally used in growing children to minimize the effect of permanent fixation on growth. They also have the advantage of being resorbed over time reducing the risk of long-term hardware related complications. Absorbable plates can be made of polymers such as polyglycolic acid (PGA), polylactic acid (PLA), polydioxanone (PDS), or various combinations of these polymers.

In view of the current prior art fixation technology, today's surgeons need systems for bone reconstruction that achieve improved bone fracture repair outcomes in an easier, more time-efficient manner.

BRIEF SUMMARY

Embodiments disclose a system and method for bone treatment, reconstruction and/or repair including internally repositioning and stabilizing bone which has been destabilized due to either fracture or designed osteotomy. The embodiments also disclose an implant device of the system for attachment to bone segments of at least one bone.

An implant device includes a connection bridge to cause retraction or distraction of first and second bone segments of a bone. The connection bridge is mountable to overlap an outer surface of the bone and configured to, in at least one plane, exert a force of retraction or distraction to one of the first and second bone segments in response to translation motion of connection bridge. The connection bridge includes a first insertion structure mountable to in overlapping relationship with an outer surface of the first bone segment. The first insertion structure has at least one rack. The connection bridge includes an internal repositioning tool having a pinion to engage the at least one rack to cause the translational motion. The connection bridge includes a locking mechanism to selectively lock the translational motion. The connection bridge includes a second insertion structure mountable to in overlapping relationship with an outer surface of the second bone segment or a third bone segment between the first bone segment and the second bone segment. The second insertion structure includes a housing to internally house at least one of the pinion and the lock mechanism and receive a portion of the at least one rack of the first insertion structure within the housing to engage the at least one the pinion and the lock mechanism internally housed in the housing.

An osseous repair system includes the implant device and a plurality of fasteners to fasten the implant device to an outer surface of a first bone segment and an outer surface of a second bone segment. The system includes a tool to interface with the implant device to cause translational motion of at least one of a first insertion structure of the implant device relative to a second insertion structure of the implant device to adjust a distance between the first bone segment and the second bone segment.

A method for treating a condition of a bone includes fastening the implant device to a first bone segment and a second bone segment by a first tool used by a surgeon. The method includes causing translational motion of a first insertion structure of the implant device relative to a second insertion structure of the implant device to adjust a distance between the first bone segment and the second bone segment using a second tool interfaced to the implant device. The method includes during the causing of the translational motion, causing one of retraction and distraction of the first bone segment relative to the second bone segment using the implant device to treat the condition where the implant device includes a fixed distance defined by pitch of a rack of teeth for predetermined measured growth in a direction associated with the translation motion.

BRIEF DESCRIPTION OF THE SEVERAL VIEWS OF THE DRAWINGS

To easily identify the discussion of any particular element or act, the most significant digit or digits in a reference number refer to the figure number in which that element is first introduced.

FIG. 1A illustrates a top view of an implant device in accordance with one embodiment with portions of a connection bridge shown transparent.

FIG. 1B illustrates a bottom view of the implant device in accordance with one embodiment with portions of a connection bridge shown transparent.

FIG. 1C illustrates a perspective view of the implant device in accordance with one embodiment with portions of the connection bridge shown as transparent.

FIG. 2A illustrates a perspective view of a second half of the connection bridge of the implant device in accordance with one embodiment and with the first half of the connection bridge removed.

FIG. 2B illustrates a bottom view of implant device with the first half of the connection bridge shown transparent and the second half opaque in accordance with one embodiment.

FIG. 3 illustrates an exploded view of a slide switch of the connection bridge in accordance with one embodiment.

FIG. 10A illustrates a top view of an implant device in accordance with a fourth embodiment and in a first position.

FIG. 10B illustrates a top view of an implant device in accordance with the fourth embodiment and in a second position.

FIG. 11A illustrates a top view of an implant device in accordance with a fifth embodiment with a portion of the connector bridge shown as transparent.

FIG. 11B illustrates a bottom view of an implant device in accordance with the fifth embodiment.

FIG. 14A illustrates a bottom perspective view of a portion of a rack and pinion for one or more embodiments.

FIG. 14B illustrates a bottom view of a portion of a repositioning tool with locking ratchet arms of FIG. 14A.

FIG. 14C illustrates an end view of the repositioning tool of FIG. 14A.

FIG. 15A illustrates a perspective view of the implant device in accordance with a seventh embodiment in a first position.

FIG. 15B illustrates a perspective view of the implant device in accordance with the seventh embodiment in a second position.

FIG. 15C illustrates a perspective view of the implant device in accordance with the seventh embodiment in a third position.

FIG. 15D illustrates a perspective view of the implant device in accordance with the seventh embodiment in a fourth position.

FIG. 20 illustrates a perspective view of at least two implant devices joined together in accordance with an eighth embodiment.

FIG. 21 illustrates a rack and pinion adapter in accordance with the eighth embodiment.

FIG. 22 illustrates a perspective view of the at least two implant devices joined together in accordance with the eighth embodiment.

FIG. 23A illustrates a perspective view of at least two implant devices joined together and in a first position.

FIG. 23B illustrates a perspective view of at least two implant devices joined together and in a second position.

FIG. 30A illustrates a top view of an implant device with a built-in adjustment handle or tool.

FIG. 30B illustrates a top view of an implant device with a built-in adjustment handle or tool.

DETAILED DESCRIPTION

Figure 1D:
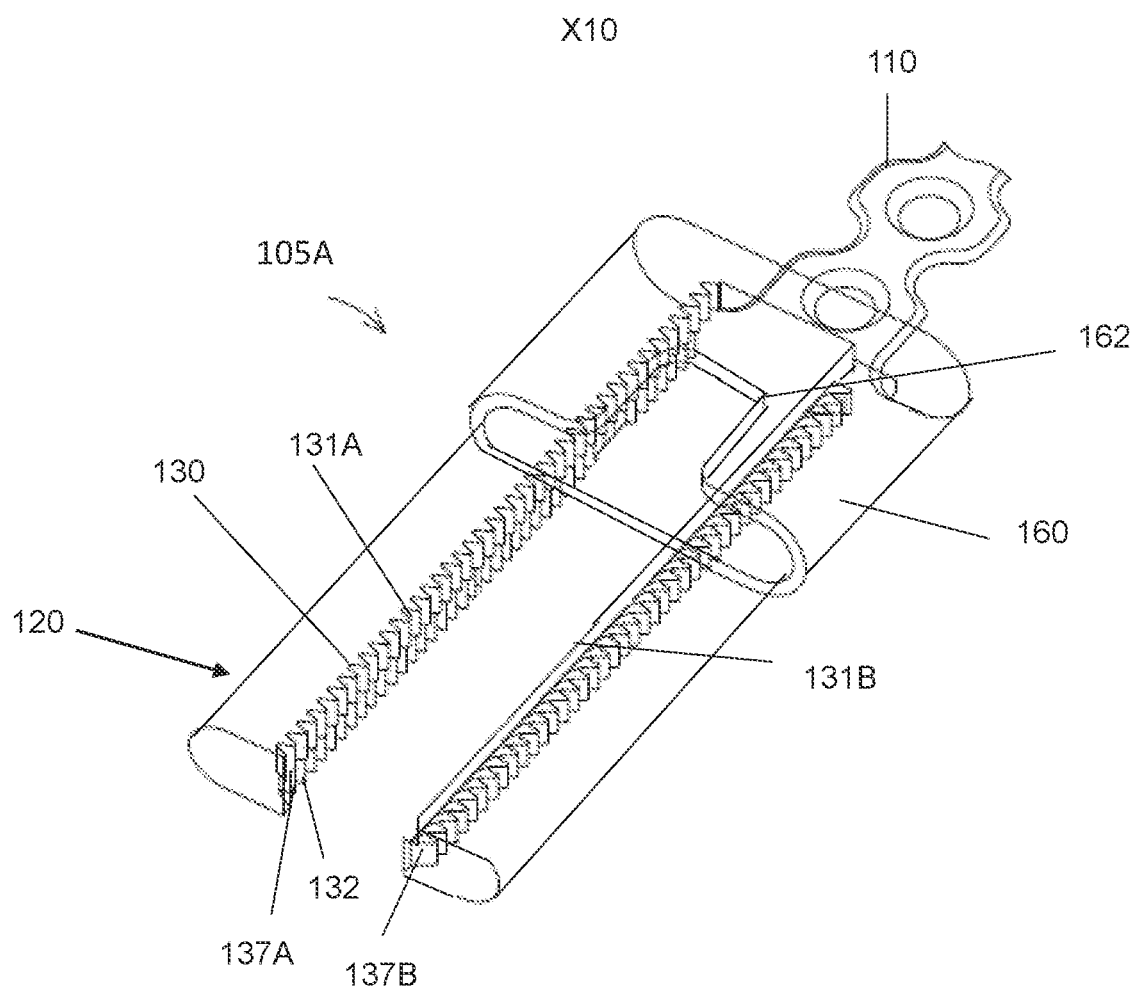
FIG. 1D illustrates a perspective view of the first insertion structure of the implant device in accordance with one embodiment.

Embodiments are described herein with reference to the attached figures wherein like reference numerals are used throughout the figures to designate similar or equivalent elements. The figures are not drawn to scale and they are provided merely to illustrate aspects disclosed herein. Several disclosed aspects are described below with reference to non-limiting example applications for illustration. It should be understood that numerous specific details, relationships, and methods are set forth to provide a full understanding of the embodiments disclosed herein. One having ordinary skill in the relevant art, however, will readily recognize that the disclosed embodiments can be practiced without one or more of the specific details or with other methods. In other instances, well-known structures or operations are not shown in detail to avoid obscuring aspects disclosed herein. The embodiments are not limited by the illustrated ordering of acts or events, as some acts may occur in different orders and/or concurrently with other acts or events. Furthermore, not all illustrated acts or events are required to implement a methodology in accordance with the embodiments.

Notwithstanding that the numerical ranges and parameters setting forth the broad scope are approximations, the numerical values set forth in specific non-limiting examples are reported as precisely as possible. Any numerical value, however, inherently contains certain errors necessarily resulting from the standard deviation found in their respective testing measurements. Furthermore, unless otherwise clear from the context, a numerical value presented herein has an implied precision given by the least significant digit. Thus, a value 1.1 implies a value from 1.05 to 1.15. The term "about" is used to indicate a broader range centered on the given value, and unless otherwise clear from the context implies a broader range around the least significant digit, such as "about 1.1" implies a range from 1.0 to 1.2. If the least significant digit is unclear, then the term "about" implies a factor of two, e.g., "about X" implies a value in the range from 0.5× to 2×, for example, about 100 implies a value in a range from 50 to 200. Moreover, all ranges disclosed herein are to be understood to encompass any and all sub-ranges subsumed therein. For example, a range of "less than 10" can include any and all sub-ranges between (and including) the minimum value of zero and the maximum value of 10, that is, any and all sub-ranges having a minimum value of equal to or greater than zero and a maximum value of equal to or less than 10, e.g., 1 to 4.

In general, embodiments disclosed herein may be applicable to bone fracture cases caused by trauma as well as reconstructive cases where a purposeful osteotomy is made to create a desired bone structure.

Embodiments disclosed herein are an integrated system and method which the inventors have found to be highly efficient and effective when used for the repair or reconstruction of bone. The embodiments enable the design and creation of customizable fixation plate arrangements for the specific repair or reconstruction of fractures or designed osteotomies in different planes. The planes of adjustment may be defined as 'X' in the same plane tangential to the surface of the plate in its long axis. The plane of adjustment may be defined as 'Y' in the tangential to the surface of a plate 90 degrees to the X axis. The planes of adjustment may be defined as 'Z' perpendicular to the plane created by the X and Y axis. A connecting bridge structure, discussed herein, may be adjustable in a linear fashion along either the X or the Y plane, a curved fashion along the X and Y planes or a combination thereof. In addition to providing a better surgical and functional result, the embodiments disclosed herein ultimately lead to shorter surgical time, which saves money, leads to lower doses of anesthesia, and reduces the opportunity to acquire secondary infections.

As defined herein, the term "fixation plates" refers to suitable surgical mounts that can be affixed, mounted, connected to an outer surface of a bone using bone fasteners or ultrasonically activated bonding, for example. The plates may be made of biocompatible material for implantation.

The embodiments disclosed herein also disclose specialized tools which provide for access to hard-to-reach anatomical locations where drilling and installation of bone-fixation screws/fasteners takes place.

In some embodiments, the implant device for reconstruction, repair or treatment of a condition of bone provides incremental adjustment that includes a fixed distance defined by a teeth pitch of a rack for predetermined measured growth in a direction associated with the translation motion. The rack may be used with a locking mechanism to lock the translation motion to a particular tooth.

In some embodiments, the osseous repair system may include at least one implant device, a tool to fasten the plates with bone fasteners and a tool to access the repositioning tool.

The implant device and related osseous repair system may be used on a long bone osteotomy. The implant device may be used to treat craniofacial abnormalities such as by mandible osteotomy, including for pediatric patients. The implant device may be used for the treatment of bone fractures or to lengthen bones. The implant device may be used for the treatment of bone conditions by retraction or distraction of bone segments of at least one bone.

The repair systems described herein may use cortical bone screws/fasteners or ultrasonically activated bonding. The auxiliary tool may be built into the implant device or removable.

FIG. 1A illustrates a top view of an implant device 100 in accordance with one embodiment with portions of a connection bridge shown transparent. The implant device 100 will be described in relation to views of the implant device 100 shown in FIGS. 1A-1F, 2A-2B, and 4.

Figure 1E:
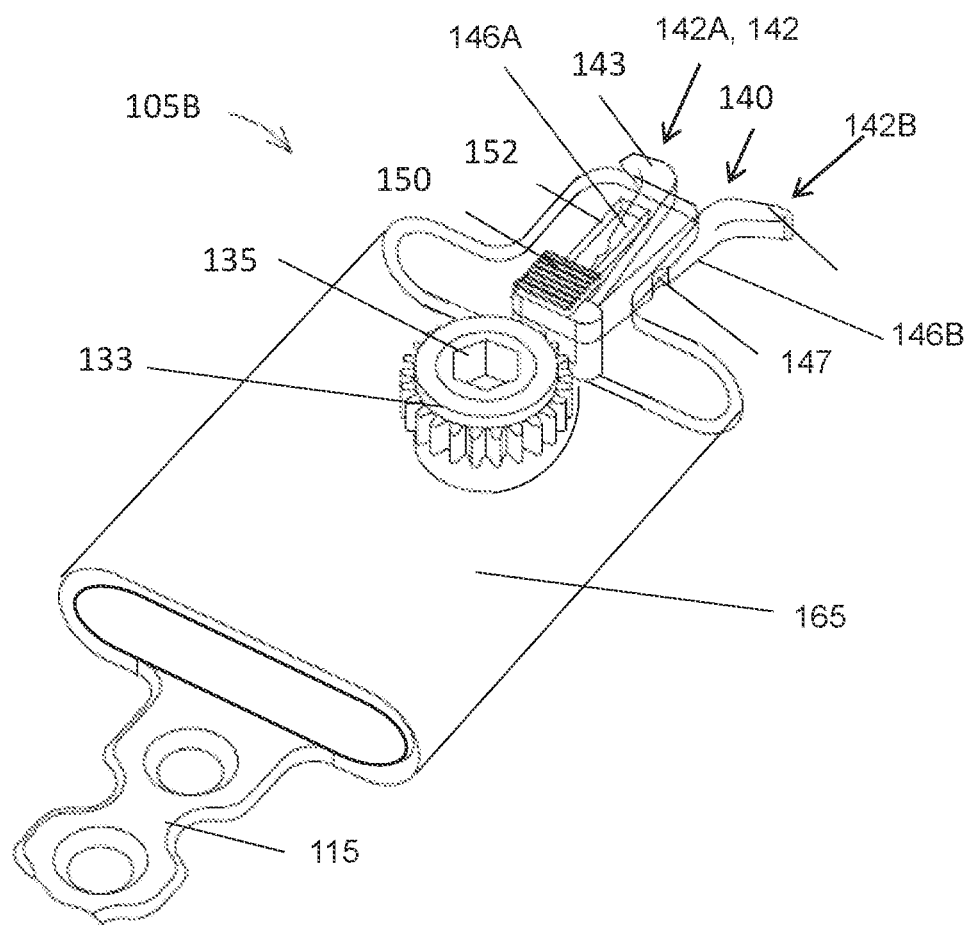
FIG. 1E illustrates a perspective view of the second insertion structure of the implant device in accordance with one embodiment.
Figure 1F:
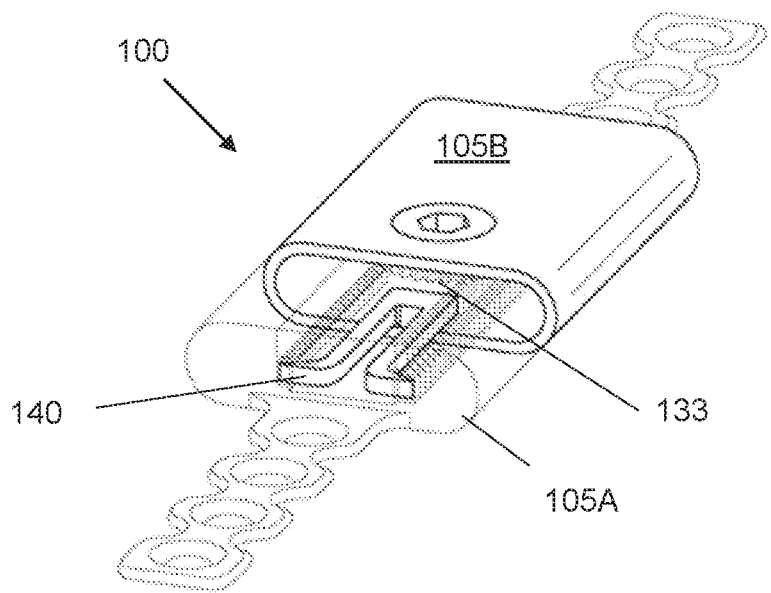
FIG. 1F illustrates an end view of the implant device in accordance with one embodiment, with some components omitted to prevent crowding.
Figure 4:
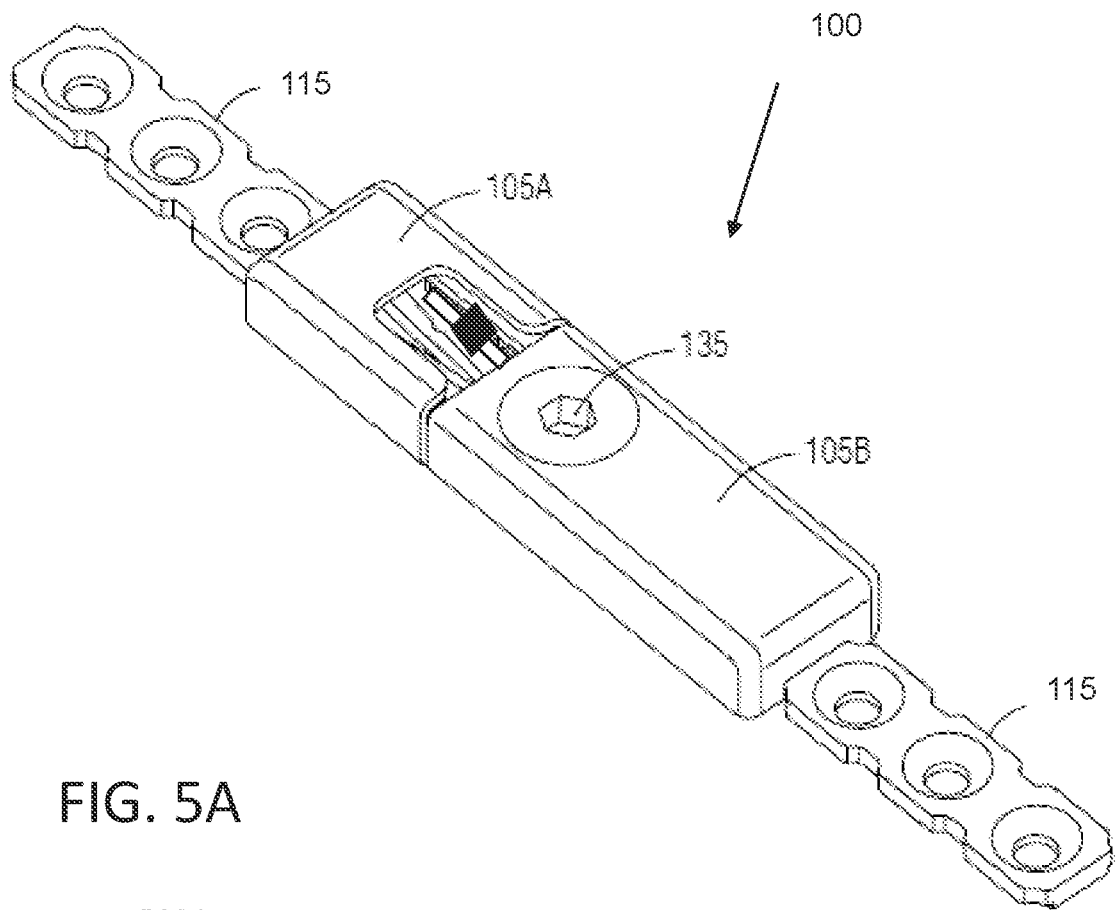
FIG. 4 illustrates a top perspective view of the implant device in accordance with one embodiment.

FIG. 1B illustrates a bottom view of the implant device 100 in accordance with one embodiment with a connection bridge shown transparent. FIG. 1C illustrates a perspective view of the implant device 100 in accordance with one embodiment with the connection bridge shown as transparent. FIG. 1D illustrates a perspective view of the first insertion structure 105A of the implant device 100 in accordance with one embodiment. FIG. 1E illustrates a perspective view of the second insertion structure 105B of the implant device 100 in accordance with one embodiment. FIG. 1F illustrates an end view of the implant device 100 in accordance with one embodiment, with some components omitted to prevent crowding. For example, the slide switch has been omitted from this view. FIG. 2A illustrates a perspective view of a second half of the connection bridge of the implant device 100 in accordance with one embodiment and with the first half of the connection bridge removed. FIG. 2B illustrates a bottom view of an implant device 100 with the first half of the connection bridge shown transparent and the second half opaque in accordance with one embodiment. FIG. 4 illustrates a bottom perspective view of the implant device 100 in accordance with one embodiment with the connection bridge shown opaque.

Figure 5A:
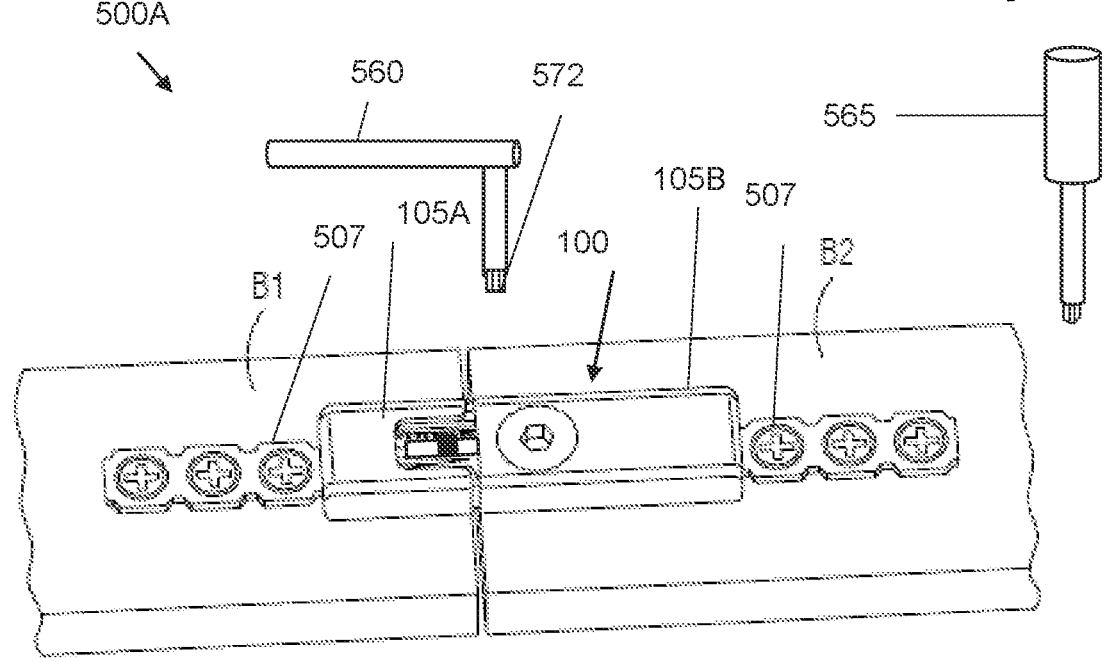
FIG. 5A illustrates the osseous repair system attached to bone sections in accordance with one embodiment.

The implant device 100 may include implant components made of biocompatible material for implantation within the body or external to the body, as will be apparent from the description herein. The implant device 100 includes a telescopic connection bridge 105 to cause retraction or distraction of first and second bone segments B1 and B2, shown in FIG. 5A. The telescopic connection bridge 105 includes a first insertion structure 105A connectable to the first bone segment B1 (FIG. 5A) and a second insertion structure 105B connectable to the second bone segment B2 (FIG. 5A).

The connection bridge 105 may be mounted to overlap an outer surface of the bone (i.e., bone segments B1 and B2) and which is configured to, in at least one plane, exert a force of retraction or distraction to one of the first and second bone segments in response to translation motion of connection bridge. The first insertion structure 105A may be mountable to in overlapping relationship with an outer surface of the first bone segment B1. The first insertion structure 105A may have a guide structure 120 with at least one rack having a curved configuration or a straight (linear) configuration. In this example, the first insertion structure 105A may include a housing 160 (FIG. 1D).

The connection bridge 105 may include an internal repositioning tool 101 having a pinion 133 and a pinion rack of the at least one rack to cause the translational motion. The connection bridge 105 may include a locking mechanism to selectively lock the translational motion of the repositioning tool 101.

The second insertion structure 105B may be mountable to in overlapping relationship with an outer surface of the second bone segment B2 or a third bone segment B3 (FIG. 27) between the first bone segment and the second bone segment. The second insertion structure includes a housing 165 to internally house at least one of the pinion 133 and at least a portion of the lock mechanism 140 and receive a portion of the at least one rack of the first insertion structure within the housing to engage the at least one the pinion and the lock mechanism. The lock mechanism 140 may include a ratchet 140.

By way of non-limiting example, the second insertion structure 105B may have at least one pinion 133 and at least one ratchet 140. Each pinion 133 is a gear with gear teeth. By way of non-limiting example, the first insertion structure 105A may have a guide structure 120 with a first rack 130 and a second rack 132. By way of non-limiting example, the embodiment of FIGS. 1A-1F provides a straight or linear configuration of the at least one rack. A portion of the guide structure 120 is insertable into the housing of the second insertion structure 105B to interface with the pinion 133 of the at least one pinion and a second rack 132 to interface with a ratchet 140 of the at least one ratchet. The ratchet 140 is insertable into the first insertion structure 105A and selectively locks the first insertion structure 105A to the second insertion structure 105B. The first rack 130 and second rack 132 may be separate and/or in stacked relation, as seen in FIG. 1D. The rotation of the pinion 133 of the repositioning tool 101, with its axis perpendicular to the movement between the plates 110 and 115, for example, activates the ratchet 140 advancing it incrementally, tooth by tooth or receptacle by receptacle. Otherwise, when the ratchet is locked, translational movement is prevented by the first insertion structure 105A and/or between the first and second insertion structures 105A, 105B. The first insertion structure can have the pinion and the second insertion structure can have the ratchet or vice versa. The term "rack" as used herein may be a guide with engaging teeth. The second rack may be a rail or guide track.

A gear rack may include a bar or rod with gear teeth that engage a pinion or, less frequently, a worm gear, together with which it forms a drive for transforming rotary motion into translatory (translational) motion or vice versa (rack-and-gear drive). The gear rack may be made with spur, helical, herringbone, saw or circular teeth. The translatory (translational) motion of the first insertion structure, for example, may be straight or curved (one plane or multiplanar). The gear rack may be configured for a single translational motion whether straight or curved or a double action translational motion whether straight or curved.

Although the embodiments herein include a second insertion structure that has both the pinion and ratchet mounted to and/or within the housing of the second insertion structure 105B, the pinion may be in one insertion structure while the ratchet (i.e., lock mechanism) is in a different insertion structure. In the example of FIGS. 1A-1F, the ratchet (i.e., lock mechanism) is mounted in the housing 165 of the second insertion structure 105B but includes a portion which extends beyond the housing 165 for insertion into the housing 160 of the first insertion structure 105A.

In some embodiments, the drive teeth of the guide structure 120 for the pinion are bidirectional, while the ratchet teeth of the guide structure 120 are saw toothed and unidirectional. A much lower distraction forces are shared by the teeth (pinion/rack plus the ratchet/rack).

In some embodiments, the guide structure 120 of the implant device may include a combined the pinion rack and racket rack into one shared dual-purpose rack.

The implant device 100 may include a first fixation plate 110, which may have at least one receptacle 112 at or between a first end and a second end of the first fixation plate 110 or in a pattern. The implant device 100 may include a second fixation plate 115, which may have at least one receptacle 117 at or between a first end and a second end of the second fixation plate 115 or in a pattern. The first fixation plate 110 may be integrated the housing 160 or the guide structure 120 of the first insertion structure 105A. The second fixation plate 115 may be integrated with the housing of the second insertion structure 105B.

The rack 130 and pinion 133 form a rack and pinion repositioning tool 101 connected to the first insertion structure 105A and the second insertion structure 105B to adjust placement of at least one of the first fixation plate 110 and/or the second fixation plate 115 in at least one of a first plane and a second plane.

By way of non-limiting example, the rack 130 and pinion 133 form the repositioning tool 101 that provides top access at a tool keyhole 135. The tool keyhole 135 is accessible on a top surface of the housing 165 of the second insertion structure 105A, for example, to mate with a tool (such as a hex tool). The patient or surgeon may apply a force of torque in a first direction, to cause the pinion to rotate in the first rotation direction. The patient or surgeon may apply a force of torque in a second direction, to cause the pinion to rotate in a second rotation direction. The direction will control whether the implant device is causing retraction or distraction between bone segments. For example, the first direction may cause retraction of the bone segments by retracting of (or reducing the distance between) the second insertion structure 105A relative to the first insertion structure 105A. The second direction may cause distraction of the bone segments by distracting of (or increasing the distance between) the second insertion structure 105B relative to the first insertion structure 105A. The embodiments should not be limited to a top access. The embodiments may include different side access methods, such as methods which use worm gear arrangement. This may be important because in some instances the keyhole "land" is in a place that is not conducive for top access adjustment due to scarring or access issues. During the surgical planning process using the VSP tool 3644 (FIG. 36), the placement of the access to the repositioning tool 101 may be planned and the implant device design adjusted accordingly.

The (first) rack 130 and pinion 133 of the repositioning tool 101 may engage an inline ratchet 140 (i.e., lock mechanism) to control and lock the increment of adjustment of the repositioning tool 101. As shown, the ratchet 140 is made of at least one leaf spring 142 or beams/shafts that flex within the elastic limits of the chosen structural plate material. An example will be described in relation to two springs. The leaf springs 142 include ratchet prongs 143, which protrude in opposite directions into a notch of mated ratchet teeth or receptacles in the second rack 132. The tip of each ratchet prong 143 of the ratchet 140 is shaped to lock movement in one direction while providing movement in the other direction when a force greater than the leaf spring's 142 holding force is applied in that direction. For example, the rate of bone growth is approximately ½ mm per 12 hours. Each click of the ratchet 140 achieves this amount of adjustment in only one direction.

Figure 38A:
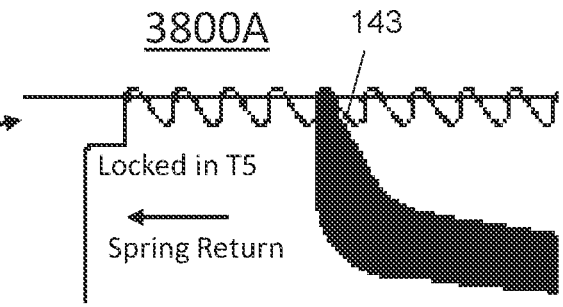
FIGS. 38A-38D illustrate the locking mechanism of the implant device with a fixed distance defined by pitch of a rack of teeth for predetermined measured growth in a direction associated with the translation motion.
Figure 37B:
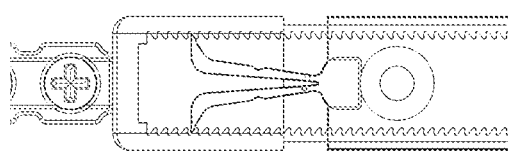
Figure 38B:
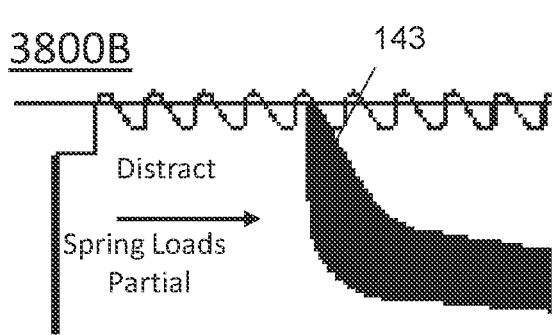
Figure 37C:
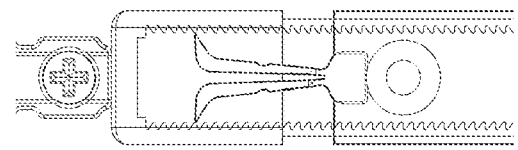
Figure 38C:
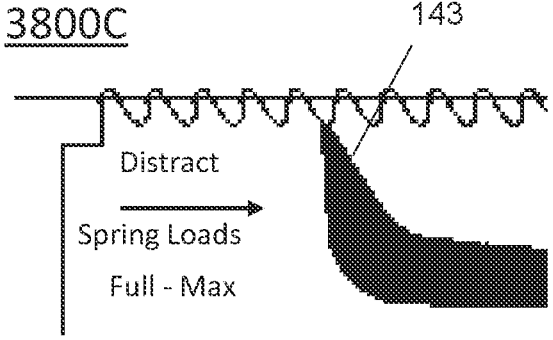
Figure 37D:
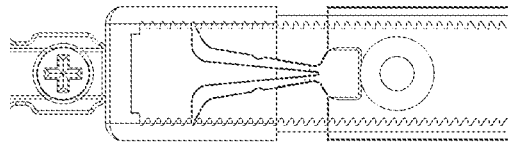
Figure 38D:
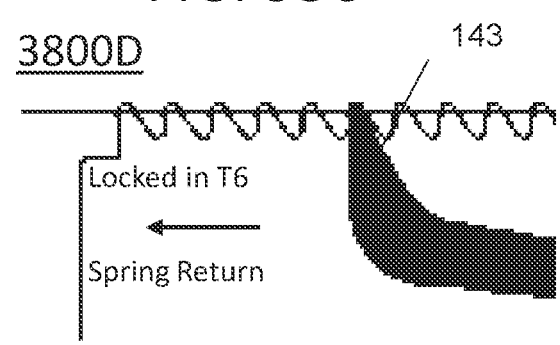

FIGS. 37A-37D illustrate translational motion of an implant device 3700A, 3700B, 3700C and 3700D during a distraction operation such that the first insertion structure distracts relative to the second insertion structure. FIGS. 38A-38D illustrate the locking mechanism of the implant device with a fixed distance defined by pitch of a rack of teeth for predetermined measured growth in a direction associated with the translation motion. In FIG. 38A, the tip of the prong 143 is at the deepest within the receptacle T5 of the teeth. In FIG. 38B, the tip of the prong 143 is at an intermediate position along the forward pitched surface of the receptacle T5. In FIG. 38C, the tip of the prong 143 is an apex or crest of the forward pitched surface of the receptacle T5. In FIG. 38D, the tip of the prong 143 is at the deepest within the receptacle T6 of the next tooth adjacent to the receptacle T5 of FIG. 38A.

In FIGS. 37A-D and FIG. 38A-D, when the male prong tip is fully engaged in a matching female tooth receptacle, its ratchet arm/leaf spring is relaxed to its preloaded level shown in FIG. 38A. As the distraction force is applied, the force causes the ratchet arm to flex as its prong tip rides up the saw tooth shaped female angled (inclined plane) tooth receptacle like a cam as shown in FIG. 38B. Further distraction force causes the ratchet prong tip to arrive at the apex or crest between female tooth receptacles as shown in FIG. 38C. At this instant, the ratchet arm is at its maximum spring deflection. Application of further distraction force then causes the prong tip to drop into the advancing female tooth receptacle with a clicking sound, as shown in FIG. 38D. At this clicking moment, the spring instantaneously goes from a fully loaded maximum deflection to its original relaxed state. The flat or negatively drafted surface of the prong tip, opposite the angled (or inclined plane/cam side of the prong tip), prevents retraction or translational motion in the opposite direction of distraction. This is considered in the resting or locked state since additional spring force must be applied in order to disengage the prong tip from its, now engaged, female ratchet receptable. The pitch of the female ratchet receptacles have a constant distance such as 0.5 mm (millimeter) so that each adjustment accounts for roughly a half day's bone growth or osteogenesis.

As shown in FIG. 1B, the ratchet 140 may be connected to the pinion 133 so that as the pinion 133 rotates, by torque force using a tool, through the teeth or receptacles of the rack, the ratchet 140 follows. The top access feature to the tool keyhole 135 is advantageous for most reduction/distraction situations since only a small access point is needed through the skin during the length adjustment (reduction or distraction) procedure.

By way of non-limiting example, the implant device 100 is configured with a fixed distance defined by the ratchet teeth pitch of a ratchet teeth rack (i.e., second rack 132) for predetermined measured growth in a direction associated with the translation motion. The at least one rack of guide structure 120 may be a dual-purpose rack to both engage the pinion and the lock mechanism.

As seen in FIGS. 1D and 2B, the first rack 130 comprises two separate rack portions 131A and 131B. The first rack portion 131A includes pinion rack teeth or receptacles. The second rack portion 131B may have a smooth surface. The pinion 133 may engage both rack portions, simultaneously.

The first insertion structure 105A includes a second rack 132 that has a first rack portion 137A and a second rack portion 137B to engage the ratchet 140. The first and second racks 130 and 132 are parallel and/or in adjacent relation.

The first insertion structure 105A includes a guide structure 120 with at least one rack. In some embodiments, the guide structure 120 may include the first rack 130 and the second rack 132 to form at least one track or guide. The first rack 130 has integrated therein a first rack portion 131A and a second rack portion 131B for the pinion 133. The second rack 132 has integrated therein a first rack portion 137A and the second rack portion 137B for the ratchet 140. The first insertion structure 105A includes a housing 160 with a channel 162 to receive the plate on which the slide switch is mounted and the channel 152 is formed. In an embodiment where the guide structure 120 has one rack, the one rack is a dual-purpose rack to both engage the pinion and the ratchet. The one rack may include one row of engaging teeth or two rows of engaging teeth.

The guide structure 120 may include one or two engaging racks. The guide structure 120 may include (1) a spur teeth engaging rack and/or (2) a ratchet teeth engaging rack. The guide structure 120 may be a single rail configuration with two engaging racks (spur and ratchet). This single rail configuration may have grooves to line up with the insertion structure or the insertion structure may have guide walls built in eliminating the need for a second guide rack.

Figure 9A:
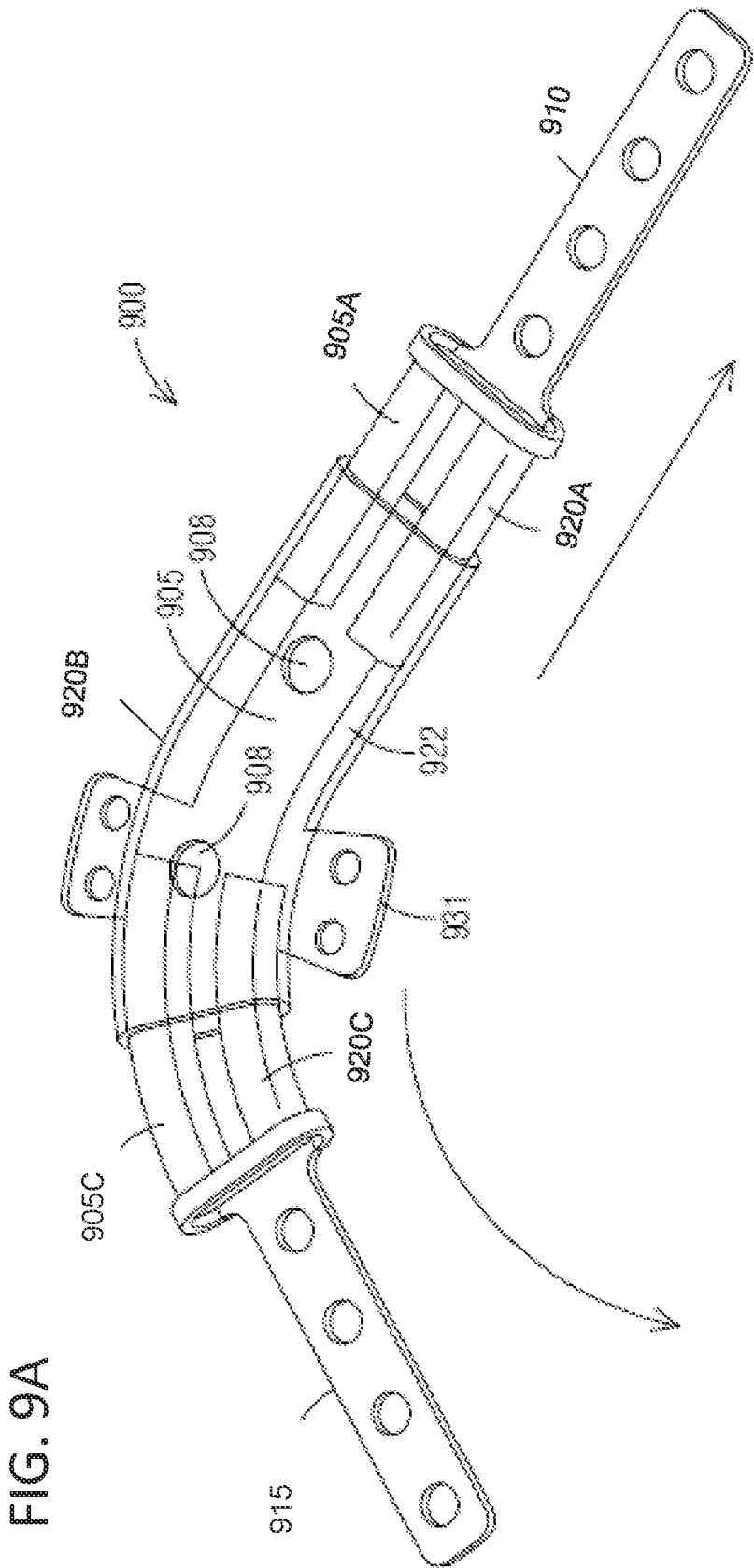
FIG. 9A illustrates a perspective view of an implant device in accordance with a third embodiment.

The mounting plates 110 and 115 and the connection bridge 105 are used in linear reduction or distraction situations. Although the first rack 130 and second rack 132 are shown to have a linear configuration, the racks may be curved and the mounting plates may have multiple hole patterns as required by the anatomy. As such, the second insertion structure 105B would have a curved profile to track and fit the curvature of the racks. An example is shown in FIG. 9A.

Figure 26A:
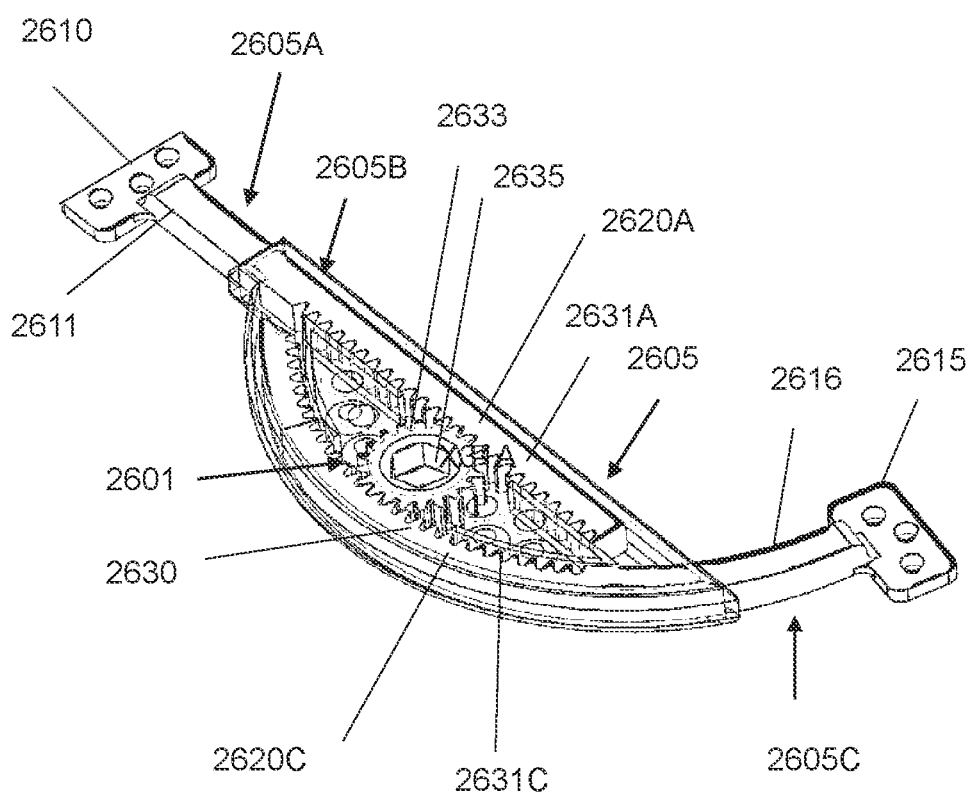
FIG. 26A illustrates a perspective view of the implant device in accordance with a tenth embodiment in a first position and with the interior components shown.
Figure 26B:
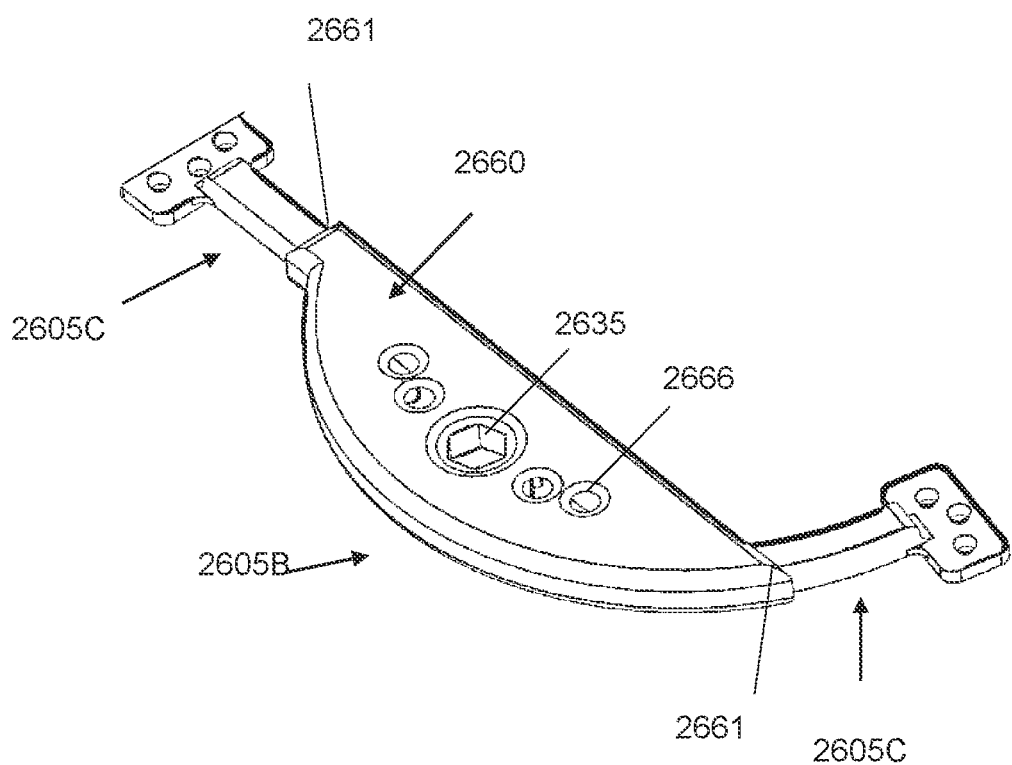
FIG. 26B illustrates a perspective view of the implant device in accordance with the tenth embodiment in a first position.
Figure 26C:
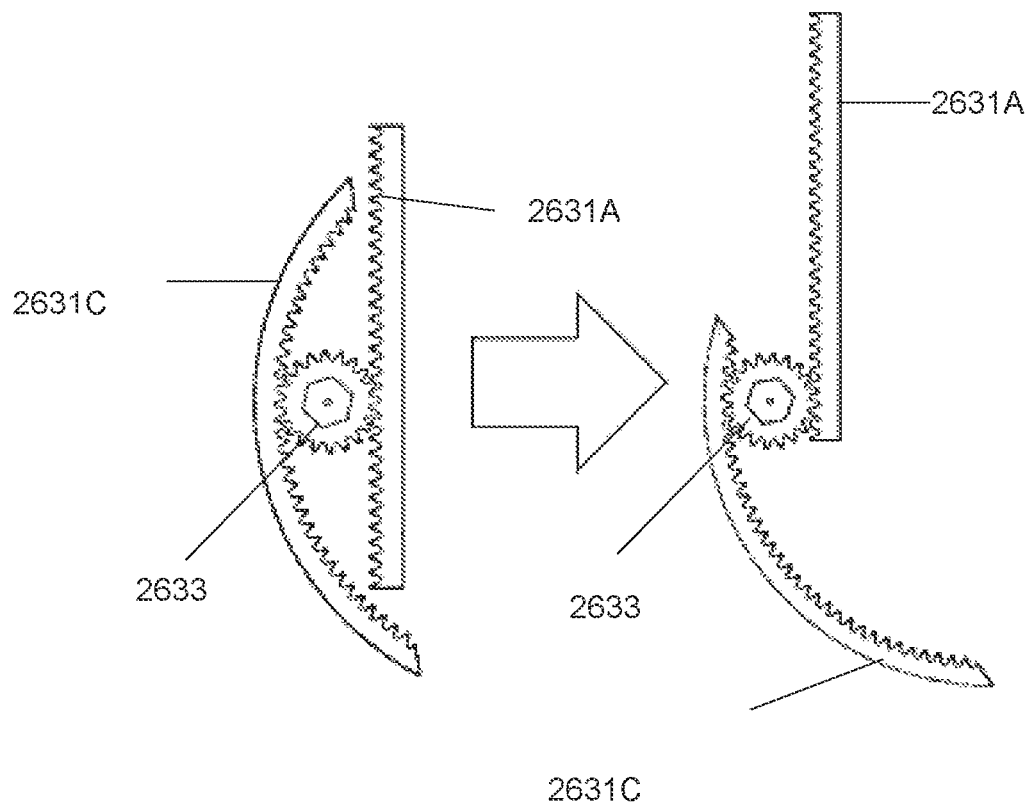
FIG. 26C illustrates a perspective view of the guide structure in accordance with the tenth embodiment in a first position and a second position.

The embodiment of FIGS. 1A-1F and 2A-2B provide a one-way retraction or distraction operation in one direction since the second rack portion 131B that has a smooth surface. However, the implant device can have a two-way retraction and/or distraction operation. In this configuration, the first insertion structure 105A may include a second rack portion 131B with receptacles or teeth, as shown in FIG. 26C) to engage the pinion 133 simultaneously with the first rack portion 131A.

The first leaf spring 142A of the ratchet 140 has a first arm having a first ratchet prong 143 at a first end of the first arm 146A. The first ratchet prong 143 engages with and mates to ratchet teeth or receptacle of the first rack portion 137A. The second leaf spring 142B of the ratchet 140 has a second arm 146B having a second ratchet prong 143 at a first end of the second arm. The second ratchet prong 143 engages the second rack portion 137B. The first arm 146A include a first indentation 147. The second arm 146B includes a second indentation 147. The first arm 146A and the second arm 146B may be cantilevered ratchet arms. The ratchet 140 may have one spring arm with a prong.

The second insertion structure 105B may include a slide switch 150, as shown in FIG. 3, to simultaneously lock/release both the first ratchet prong 143 in the first rack portion 137A and the second ratchet prong 143 in the second rack portion 137B. This release allows the installer to line up the ratchet teeth and the ratchet prongs based on the exact mounting positions of the connecting bridge. The slide switch 150 engages a slide channel 152 in which to slide the slide switch 150 between a first position and a second position. The slide switch 150 has a mount 310, as will be described in FIG. 3.

The slide switch 150 may push on a surface of the cantilevered ratchet arms so that the prongs 143 of the ratchet arms disengage with its mating ratchet teeth or receptacle in the second rack 132 so the relative distance of the two plates 110 and 115 can be adjusted during installation or upon demand by the surgeon or patient by retraction or distraction of the first insertion structure 105A and the second insertion structure 105B. The slide switch 150 locks in the disengaged position as the indentations 147 are reached. Pushing the slide switch 150 in the opposite direction disengages the indentations 147 and returns the slide switch 150 to its original position so that the ratchet prongs 143 re-engage with the adjacent ratchet teeth or receptacles in the new position.

As for mechanical operation, sliding the slide switch 150 to the first position causes the slide switch 150 to engage the first arm 146A and second arm 146B such that the first arm 146A and the second arm 146B simultaneously move away from each other to expand a distance therebetween and engage the first ratchet prong 143 in a first recess in the first rack portion 137A and engage the second ratchet prong 143 in a second recess in the second rack portion 137B.

As for mechanical operation, sliding the slide switch 150 to the second position causes the slide switch 150 to engage the first arm 146A and second arm 146B such that the first arm 146A and the second arm 146B simultaneously move toward each other to reduce a distance therebetween and disengage the first ratchet prong 143 from the first recess in the first rack portion 137A and disengage the second ratchet prong 143 from the second recess in the second rack portion 137B.

Figure 6A:
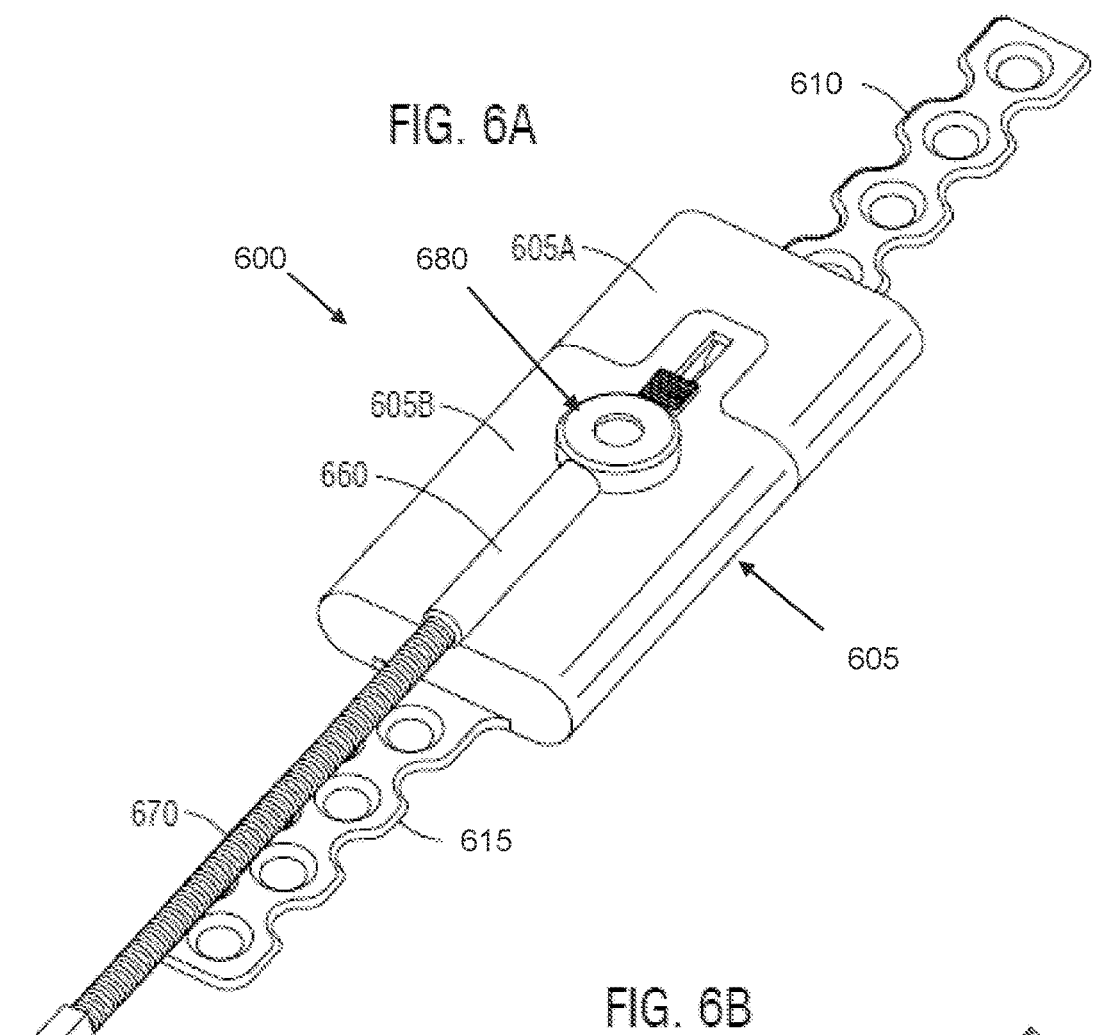
FIG. 6A illustrates a perspective view of an implant device in accordance with a second embodiment.
Figure 6B:
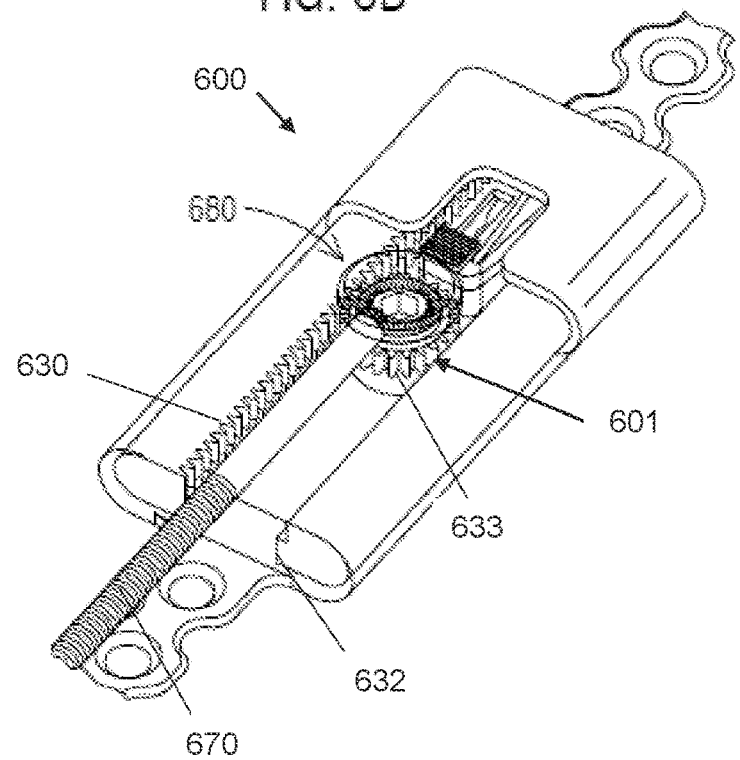
FIG. 6B illustrates a perspective view of an implant device in accordance with the second embodiment and with the second half of the connection bridge shown transparent.
Figure 7:
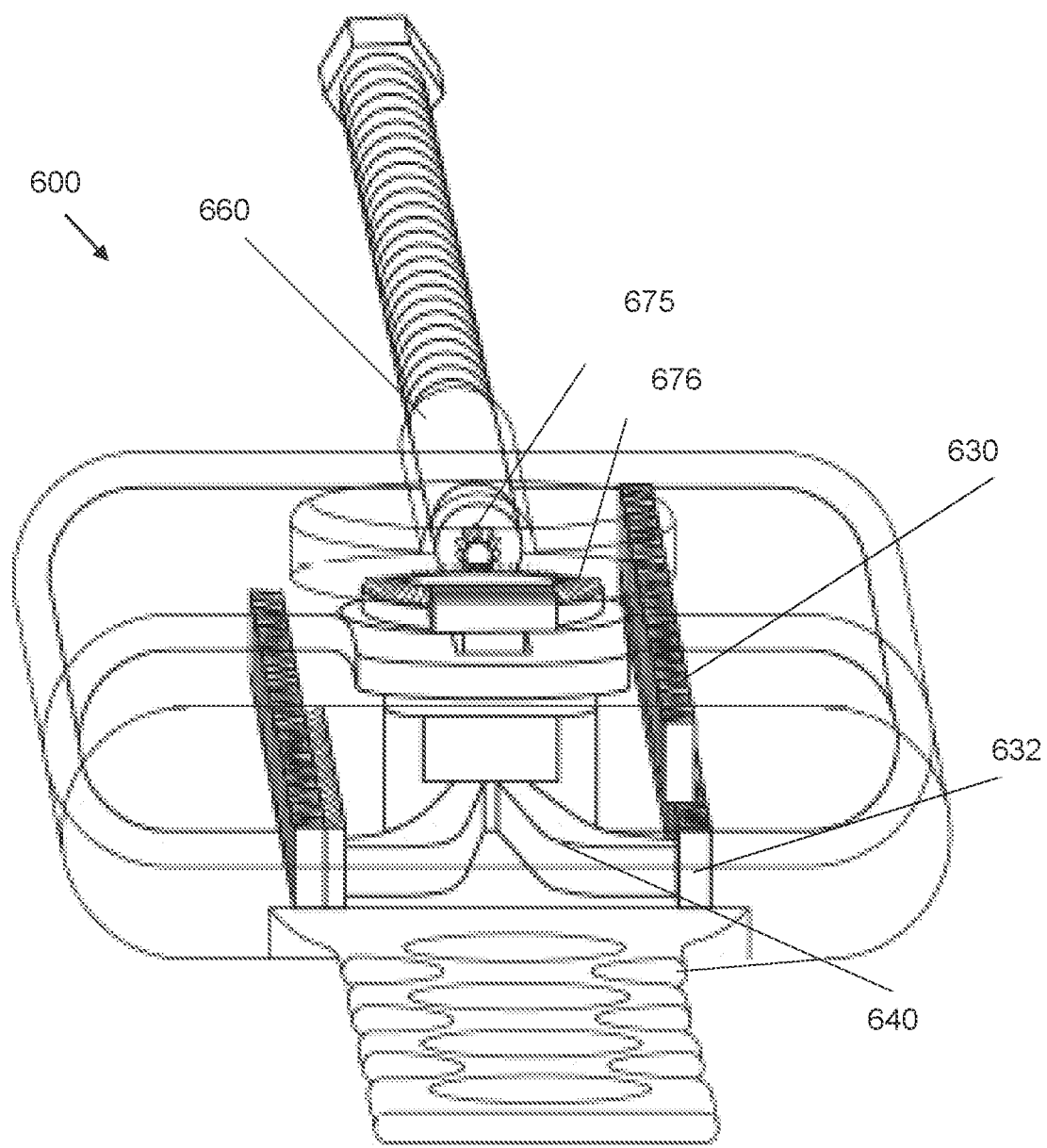
FIG. 7 illustrates an end view of the embodiment of FIG. 6A in accordance with the second embodiment.

Once the slide switch 150 is unlocked, the pinion 130 may be activated by either the top access hex tool (not shown) that engages a tool keyhole 135 or aside access bevel gear, as discussed in relation to FIGS. 6A-6B and 7, for example. The slide switch 150 may be used by the surgeon to control movement of the insertion structures of the connection bridge for easy of adjustment. However, once the surgery is complete, the slide switch 150 may remain in the first position so that the lock mechanism locks in or limits the translational motion to a predetermined measured growth in a direction associated with the translation motion provided by the pitch of the ratchet teeth rack (i.e., rack 132), for example.

By way of non-limiting example, the first insertion structure may include an arm 2611 (FIG. 26A) between the fixation plate and the guide structure 120. As described below, a third insertion structure may include an arm 2616 (FIG. 26A) between the fixation plate and its guide structure 120.

FIG. 3 illustrates an exploded view of a slide switch 150 of the telescopic connection bridge 105 in accordance with one embodiment. As a non-limiting example, the slide switch 150 includes a button 352 with a post 354 connected to an underside of the button 352. The slide switch 150 includes a first mount 320 having a hole 324 to receive the post 354. The first mount 320 may include mount legs 326. The slide switch 150 may include a second mount 310 having a hole 314 to receive post 354. The second mount and the button 352 may be one element. The second mount 310 is positioned between the underside of the button 352 and the top of the first mount 320. The second mount 310 may slide along the top side of the plate with the slide channel 152. The first mount 320 may slide along an underside of the plate with the slide channel 152.

The legs 326 are shown as generally tubular shaped. The legs 326 are configured to snap into the indentations 147 as the slide switch moves to unlock the ratchet 140. The rachet arms may fit within the gap between the legs, for example.

The implant devices include a telescopic connection bridge to cause retraction or distraction of first and second bone segments. The connection bridge includes a first insertion structure connectable to the first bone segment and at least one rack. The bridge includes a second insertion structure connectable to the second bone segment or a third bone segment between the first bone segment and the second bone segment. The second insertion structure has at least one of a pinion and a lock mechanism (i.e., ratchet). The at least one rack is insertable in the second insertion structure to interface with at least one of the pinion or lock mechanism. The lock mechanism selectively locks the first insertion structure to the second insertion structure.

FIG. 5A illustrates the osseous repair system 500A attached to bone segments B1 and B2 in accordance with one embodiment. The osseous repair system 500A includes implant device 100 and fasteners 507 to attach the first fixation plate 110 to bone segment B1 and the second fixation plate 115 to bone segment B2. The fasteners 507 are made of biocompatible material suitable for implantation in the human body or an animal body and fixation in bone.

The second insertion structure 105A includes top access to the keyhole 135 to the pinion 133 to selectively apply at least one of a first force of torque in a first direction, to cause the pinion to rotate in a first rotation direction along the at least one rack and a second force of torque in a second direction, to cause the pinion to rotate in a second rotation direction along the at least one rack. The first rotation direction and the second rotation direction are opposite rotation directions.

The osseous repair system 500A may include a first tool 565 and a second tool 560. The first (fixation) tool 565 is used to screw the fasteners 507 into a bone or bone segment. The second tool 560 may include an end 572, which mates with the keyhole 135. The end 572 may have a hexagonal shape or other shape the is keyed to the keyhole 135.

Figure 5B:
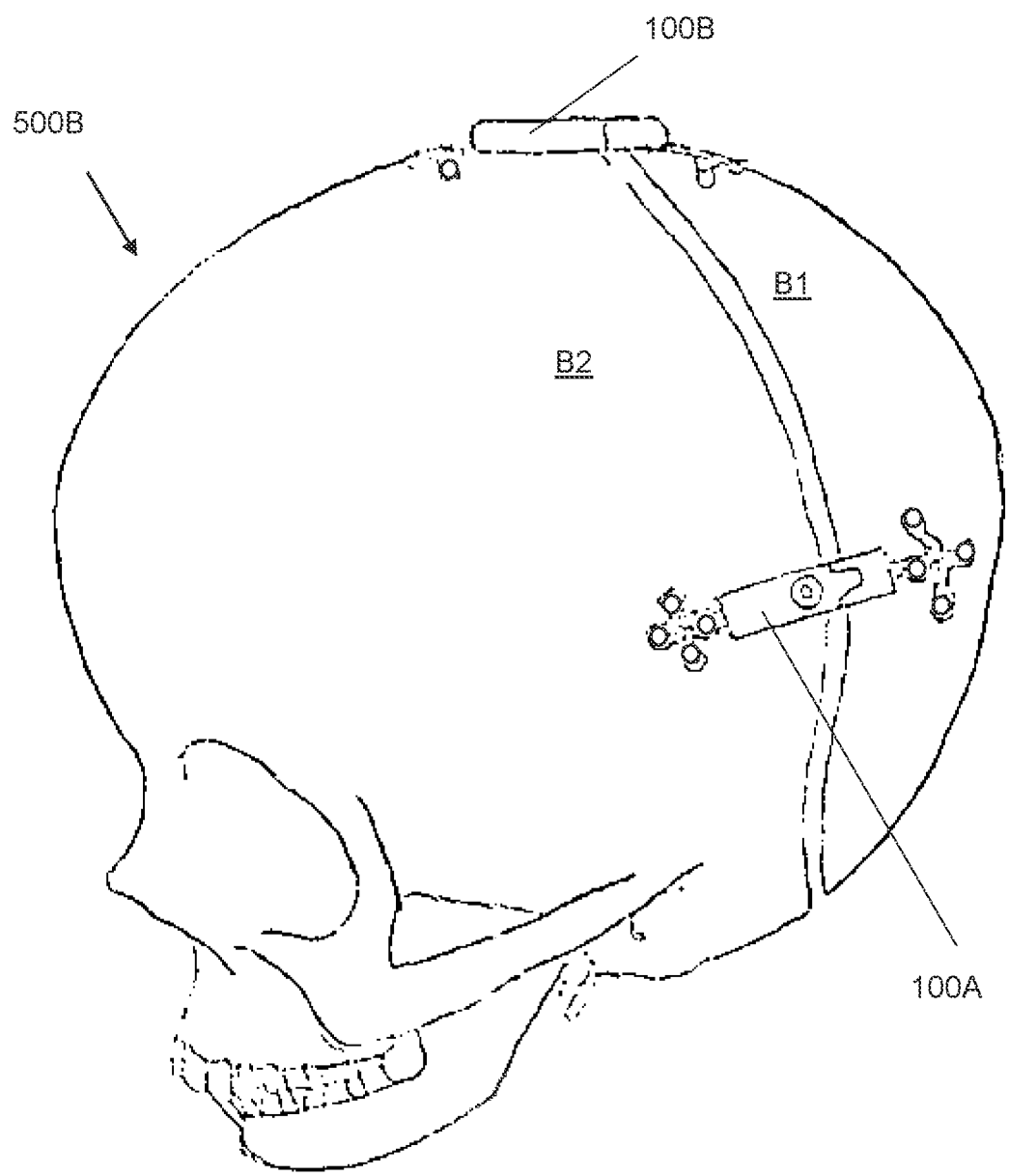
FIG. 5B illustrates the osseous repair system attached to bone sections in accordance with one embodiment.

FIG. 5B illustrates the osseous repair system 500B attached to bone sections in accordance with one embodiment. The bone sections of FIG. 5B are part of a cranium. The osseous repair system 500B includes at least two implant devices 100A and 100B, in spaced relation. The implant devices 100A and 100B are essentially the same as implant device 100 except the first fixation plate to bone segment B1 and the second fixation plate have a cross shaped configuration with crossing segments. Each segment receives at least one fastener 507. Although the system 500B has at least two implant devices, only one second tool 560 may be needed. As shown, the keyhole is accessible from the top to activate the pinion with a keyed tool (i.e., second tool 560). System 500B may include the first and second tools 565 and 560 shown in FIG. 5A.

Figure 5C:
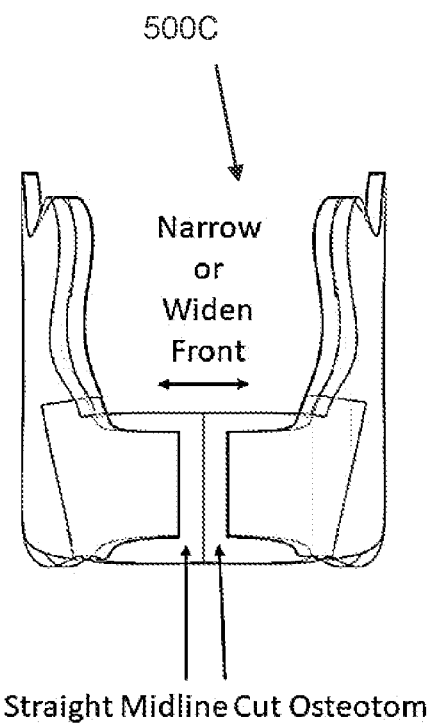
FIG. 5C illustrates an example midline cut osteotomy in the front of a mandible.

FIG. 5C illustrates an example midline cut osteotomy in the front of a mandible 500C.

Figure 5D:
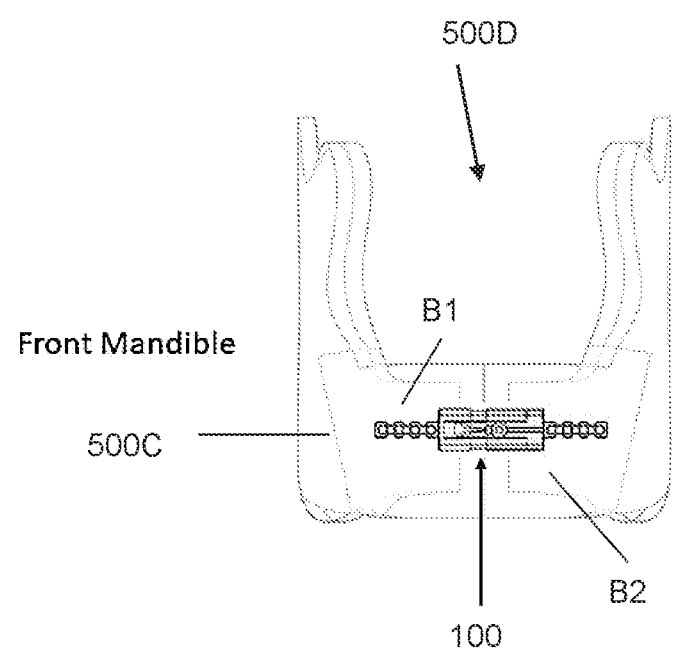
FIG. 5D illustrates the osseous repair system attached to bone sections in accordance with one embodiment.
Figure 36:
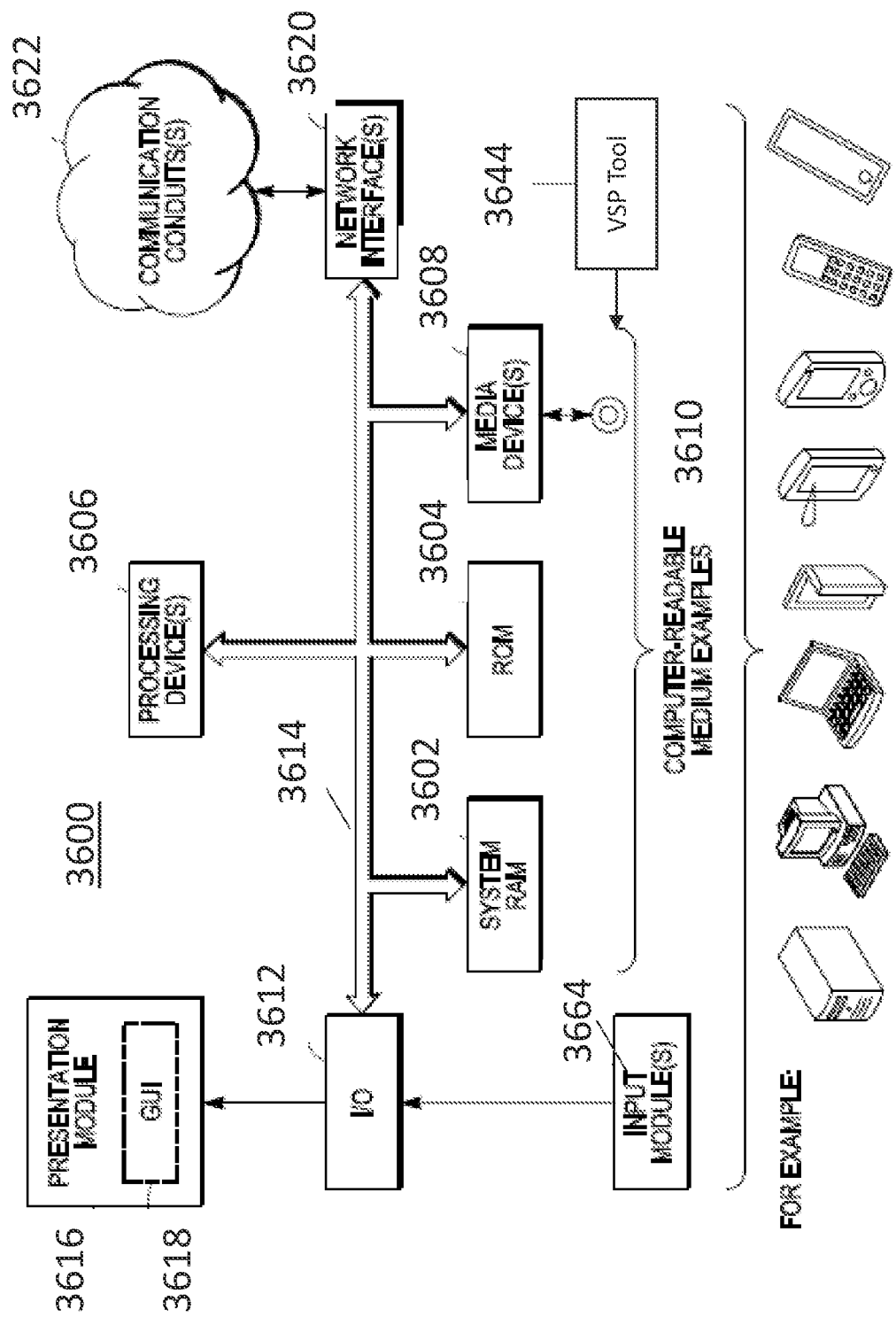
FIG. 36 illustrates a block diagram of a computer functionality.
Figure 37A:
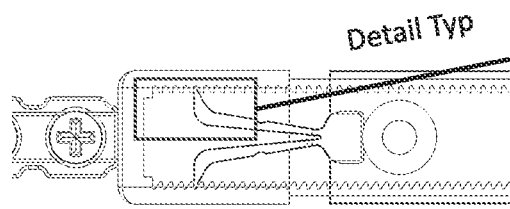
FIGS. 37A-37D illustrate translational motion of an implant device during distraction operation.

FIG. 5D illustrates the osseous repair system 500D attached to bone sections of a mandible 500C in accordance with one embodiment. The mounting plates are shown as a non-limited example. In many cases, it may be required to provide customized bands around the front teeth, to properly separate at the midline of the mandible. System 500D may include the first and second tools 565 and 560 shown in FIG. 5A. In this embodiment, the implant device 100 is attached to the front of a mandible 500C. Although the housing of the implant device 100 is shown generally straight, it may be curved in a Z-direction. The curvature of the housing of the connection bridge may be designed using a Virtual Surgical Planning (VSP) tool 3644 (FIG. 36). In some treatment scenarios, a straight midline cut osteotomy may be made, as shown in FIG. 5C. The implant device 100 may narrow or widen the mandible by retracting or distracting the cut bones segments made by a straight midline cut. The housings or components of the connection bridge and the plates can be contoured to fit with a specific anatomy contour (not just the fixation plates with holes).

Figure 5E:
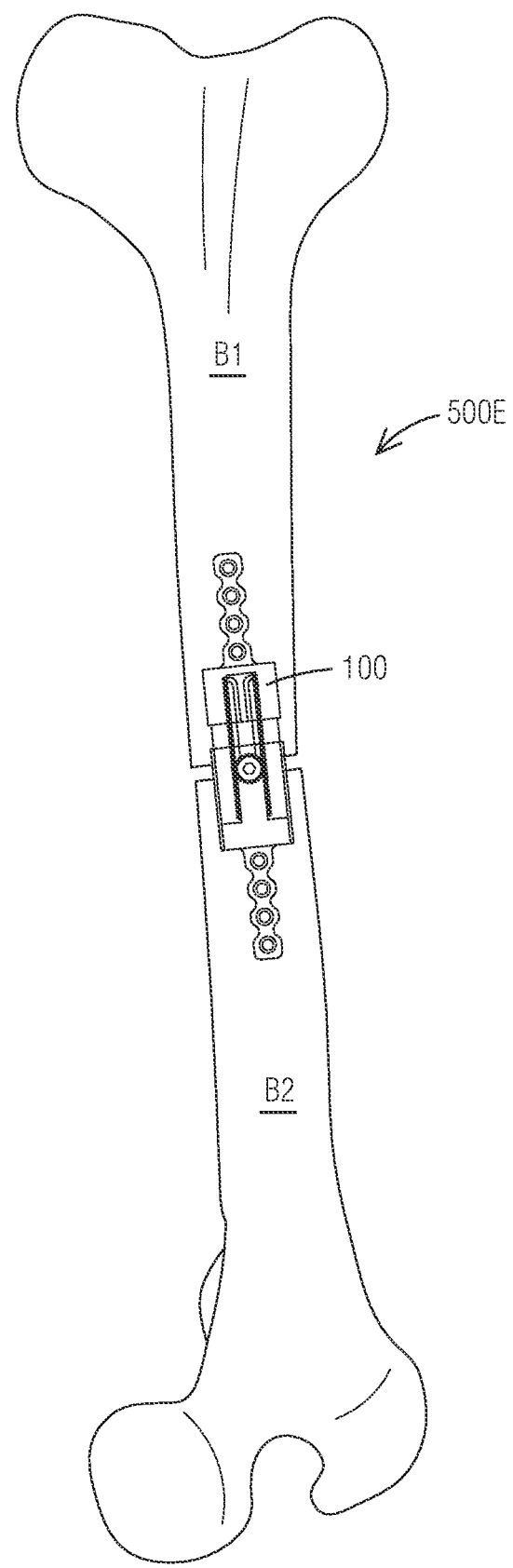
FIG. 5E illustrates the osseous repair system attached to long bone sections in accordance with one embodiment.

FIG. 5E illustrates the osseous repair system 500E having an implant device 100 attached to bone sections B1 and B2 of a long bone in accordance with one embodiment. System 500E may include the first and second tools 565 and 560 shown in FIG. 5A.

Instead of accessing the pinion using a keyhole 135, a miter gear may be used, as will now be described in relation to FIGS. 6A-6B and 7, with an adjustment handle 660. Additionally, a worm gear (see other figures for single guide rail system). The handle 660, miter gear and part of the pinion serve as an integrated adjustment tool 680 for the repair system that is built into the connection bridge. In some embodiments, the built-in tool 680 interfaces with the repositioning tool 601 so that after surgery the patient or care giver can retract or distract the bone segments connected to the implant device.

FIG. 6A illustrates a perspective view of an implant device 600 in accordance with a second embodiment. FIG. 6B illustrates a perspective view of an implant device 600 in accordance with the second embodiment and with the second half of the connection bridge shown transparent. FIG. 7 illustrates an end view of the embodiment of FIG. 6A in accordance with second embodiment.

The purpose of this embodiment is to provide post-surgical adjustment where an adjustment handle 660 is exiting the patient's anatomy via a more hidden position to minimize scarring in prominent locations. FIGS. 6A-6B and 7 show one non-limiting adjustment handle made from a coiled spring which means it has a flexible axis. The implant device 600 is similar to implant device 100, so only the differences will be described.

The implant device may include a built-in adjustment tool 680 having a handle 660. The adjustment tool may include a built-in handle 660 mounted to the connection bridge 605. The adjustment tool 680 may include an interface, such as a first gear 675, at one end of the handle 660 coupled to the repositioning tool 601, such that rotation of the built-in handle causes the translational motion.

The handle 660 and pinion 633 form a miter gear configuration. The handle 660 includes a spring 670. The handle 660 includes a first gear 675 that may be beveled with a first diameter. The pinion 633 may include a gear portion 676 with a second diameter to mate with the first gear 675 in a miter gear configuration. When the handle 660 or the spring 670 is rotated in a first direction, the pinion 633 can be adjusted tooth by tooth, for example, when the slide switch 650 is in an unlocked position to unlock the ratchet 640. The pinion 633 otherwise operates in a similar manner as pinion 133 previously described. The slide switch is designed to be used during installation or surgical adjustment. It may be locked open for patient or parental adjustment.

When the spring 670 is turned in the opposite direction, it uncoils and does not provide enough torque to advance the pinion 633 thus, providing directional "fool proofing" or an adjustment poka-yoke for parents in addition to the directional control of the ratchet pawl.

The implant device 600 includes a telescopic connection bridge 605 to cause retraction or distraction of first and second bone segments. The telescopic connection bridge 605 includes a first insertion structure 605A connectable or mountable to the outer surface of the first bone segment B1 and a second insertion structure 605B connectable or mountable to the outer surface of the second bone segment B2. The second insertion structure 605B includes at least one pinion 633 and at least one ratchet 640. The first insertion structure 605A has a first rack 630 insertable in the second insertion structure 605B to interface with a pinion 633 of the at least one pinion and a second rack 632 to interface with a ratchet 640 of the at least one ratchet. The ratchet 640 is insertable into the first insertion structure 605A and selectively locks the first insertion structure 605A to the second insertion structure 605B to prevent movement therebetween.

Figure 8:
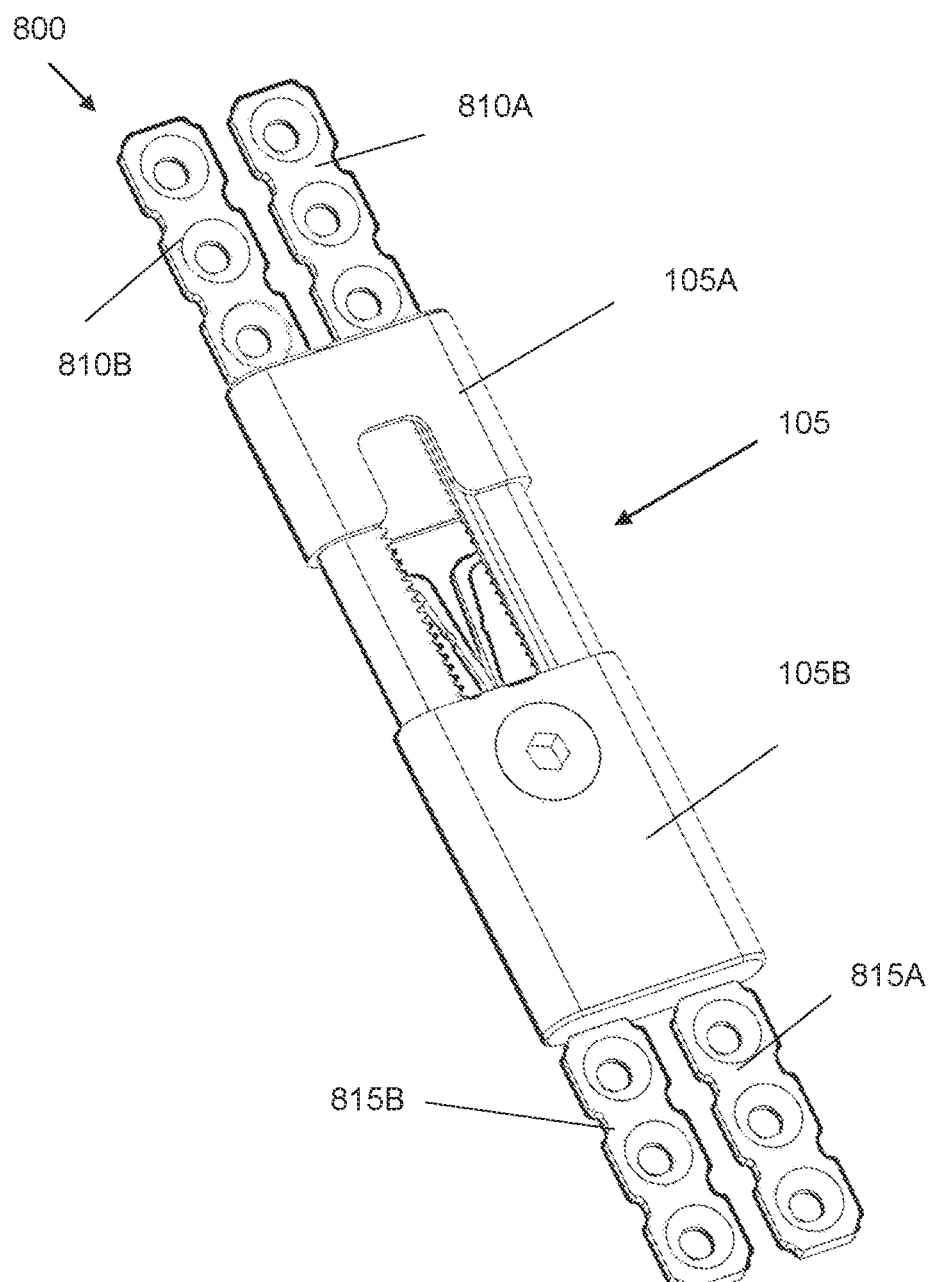
FIG. 8 illustrates a perspective of the implant device with multiple fastening plates.

The first insertion structure 605A is fastened to a bone segment using a first fixation plate 610. The second insertion structure 605B to is fastened to a bone segment using a second fixation plate 615. As should be understood, the fixation plate of the second insertion structure may vary based on whether the second insertion structure engages two other insertions structure from opposite ends as described in relation to FIGS. 9A and 10A-10B, for example, FIG. 8 illustrates a perspective of the implant device 800 with multiple fastening plates. The implant device 800 is similar to implant device 100 so only the differences will be discussed. The implant device 800 includes a telescopic connection bridge 105. The telescopic connection bridge 105 includes a first insertion structure 105A connectable to the first bone segment B1 and a second insertion structure 105B connectable to the second bone segment B2.

The first insertion structure 105A has at one end two first fixation plates 810A and 810B connected thereto. Each plate 810A and 810B has receptacles to receive fasteners. The second insertion structure 105B has at one end two second fixation plates 815A and 815B connected thereto. Each plate 815A and 815B has receptacles to receive fasteners. As should be understood, the configuration of the plates may vary based on the type of bone segment it is to be attached. Instead of being flat, it may have a curvature that tracks the curvature of the bone or bone segment.

FIG. 9A illustrates a perspective view of an implant device 900 in accordance with a third embodiment. To prevent overcrowding in the figure, some of the components have been omitted. Here, the implant device 900 includes a telescopic connection bridge 905 to cause retraction or distraction of first and second bone segments. However, the connection bridge 905 may be connected to a third bone segment between the first and second bone segments. In this embodiment, the connection bridge 905 is configured to receive a straight insertion structure and a curved insertion structure which are combined to achieve certain distraction directions, each having their own range of adjustment and a shared connection bridge 905. It should be understood that the connection bridge 905 may have two separate straight insertion structures or two curved insertion structures. The curvature of the two curved insertion structures may have different arcs of curvature. An example, two curved insertion structures is shown in FIGS. 10A-10B. Another example of a straight insertion structure and a curved insertion structure is shown in FIGS. 26A-26C.

The telescopic connection bridge 905 includes a first insertion structure 905A connectable to the first bone segment B1. The telescopic connection bridge 905 includes a second insertion structure 905B and a third insertion structure 905C. The third insertion structure 905C may be connected to a second bone segment B2 by fixation plate 915. The second insertion structure 905B may be connected via at least one fixation plate 931 to a third bone segment B3 located between the first bone segment B1 and the second bone segment B2. The second insertion structure 905B may include fixation plates 931 on opposite sides and/or external to the interior housing of the connection bridge 905.

The second insertion structure 905B may have at least one pinion (i.e., pinion 133) (not shown) and at least one ratchet (i.e., ratchet 140) (not shown). These features will be described in more detail in relation to FIGS. 12 and 13. The second insertion structure 905B also includes features similar to second insertion structure 105B and will not be repeated.

The first insertion structure 905A includes guide structure 920A that is similar to guide structures 120. The first insertion structure 905A includes first fixation plate 910. Accordingly, no further discussion will be provided. The third insertion structure 905C includes guide structure 920C that is similar to guide structure 120. However, the guide structure 920C are curved. In this example, the connection bridge 905 may have two pinions (not shown), one to engage the guide structures 920A and another pinion to engage the guide structure 920C. Likewise, the connection bridge 905 may have two ratchets, one to engage the guide structures 920A and another ratchet to engage the guide structure 920C. Each of these ratchets may be locked in a manner with a slide switch previously described.

In FIG. 9A, the second insertion structure 905B has two open ends to receive the guide structure 920A of the first insertion structure 905A through a first open end and guide structure 920C of the third insertion structure 905C through a second open end opposite of first open end. The operation of the first insertion structure 905A relative to the second insertion structure 905B is essentially the same as previously described in relation to first insertion structure 105A relative to the second insertion structure 105B, of FIG. 1A-1F. The operation of the third insertion structure 905C relative to the second insertion structure 905B is essentially the same as previously described in relation to insertion structure 105A relative to the second insertion structure 105B, of FIG. 1A-1F. The second insertion structure 905B includes holes 908 for placement of the key holes 935A and 935C (FIG. 9B).

Figure 9B:
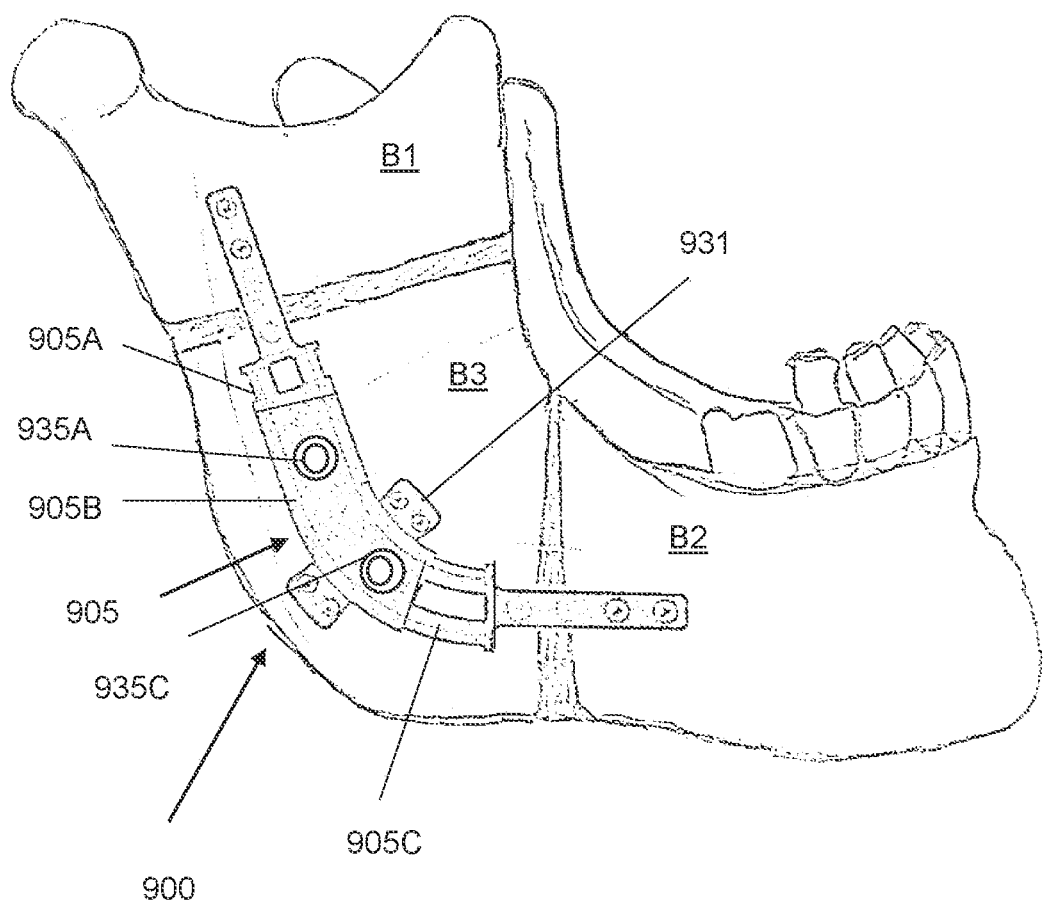
FIG. 9B illustrates the implant device of FIG. 9A implanted on a bone.

FIG. 9B illustrates the implant device 900 of FIG. 9A implanted on a bone with bone segments B1, B2 and B3. The implant device 900 may include key holes 935A and 935C to connect to pinions. This allows each insertion structure 905A and 905C to be independently adjusted. The slide switches have been omitted to prevent crowding in the figure.

FIG. 10A illustrates a top view of an implant device 1000 in accordance with a fourth embodiment and in a first position or retraction position. FIG. 10B illustrates a top view of an implant device 1000 in accordance with the fourth embodiment and in a second position or a distraction position. The implant device 1000 can be used in angled or curved reduction or distraction situations. Again, a rack and pinion 1033 of a reposition tool 1001 with a top access has been employed with an inline ratchet (not shown) to control the increment of adjustment following the curvature of the guide structure 1020A and guide structure 1020C.

The telescopic connection bridge 1005 includes a first insertion structure 1005A connectable to the first bone segment. The telescopic connection bridge 1005 includes a second insertion structure 1005B and a third insertion structure 1005C. The third insertion structure 1005C may be connected to a second bone segment. The second insertion structure 1005B may be connected to a third bone segment located between the first bone segment and the second bone segment.

The second insertion structure 1005B may have at least one pinion 1033 and at least one ratchet (i.e., ratchet 140) (not shown). These features will be described in more detail in relation to FIGS. 12 and 13. The second insertion structure 1005B also includes features similar to second insertion structure 105B and will not be repeated.

The first insertion structure 1005A includes guide structure 1020A that is similar to guide structures 120 but in this instance, the guide structure 1020A includes a first curved rack portion 1031A with a rack of teeth or receptacles and a second curved rack portion 1038A without teeth to provide a first guide rail. The first insertion structure 1005A includes first fixation plate 1010 which is curved or angled. The first fixation plates 1010 include receptacles to receive bone fasteners, for example.

The third insertion structure 1005C includes guide structure 1020C that is similar to guide structure 120. However, the guide structure 1020C is curved. The guide structure 1020C includes a first curved rack portion 1031C with a rack of teeth or receptacles and a second curved rack portion 1038C without teeth or receptacles to provide a second guide rail. The third insertion structure 1005C includes fixation plate 1015 which is curved or angled. Although not shown, the guide structures 1020A and 1020C may include racks of teeth for the ratchet.

In this embodiment, the pinion 1033 engages both first curved rack portion 1031A and first curved rack portion 1031C, simultaneously, to telescope (cause distraction) or retract (cause retraction) simultaneously the first insertion structure 1005A relative to the third insertion structure 1005C. During distraction or telescopic operation, the first curved rack portion 1031C rides along the first guide rail. Likewise, the first curved rack portion 1031A rides along the second guide rail to a fully retracted position, such as shown in FIG. 10A, to a distraction position as shown in FIG. 10B.

FIG. 11A illustrates a top view of an implant device 1100 in accordance with a fifth embodiment with a portion of the connector bridge shown as transparent. FIG. 11B illustrates a bottom view of an implant device 1100 in accordance with the fifth embodiment. To prevent overcrowding in the figures, some of the components have been omitted.

The implant device 1100 is essentially the same as the implant device 100, except the connection bridge 1105 is curved. This embodiment, like the embodiment of implant device 100, includes a connection bridge that telescopes or retracts in one direction. The guide structure 1120 (i.e., guide structures 120) is curved. The first fixation plate 1110 is linear or angled relative to the center of rotation of the pinion 1133. The second fixation plate 1115 is linear or angled relative to the center of rotation of the pinion 1133. Both the first and second insertion structures 1105A and 1105B are curved.

Figure 12:
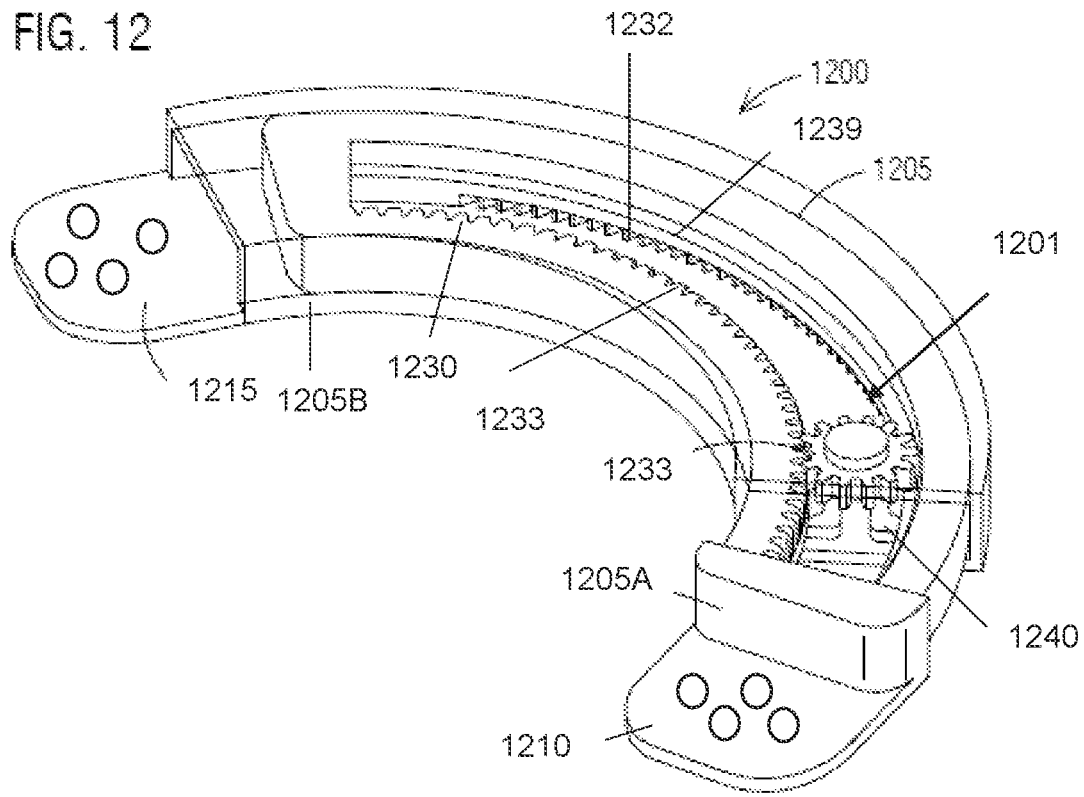
FIG. 12 illustrates a top view of an implant device in accordance with a sixth embodiment with a portion of the connection bridge transparent.
Figure 13:
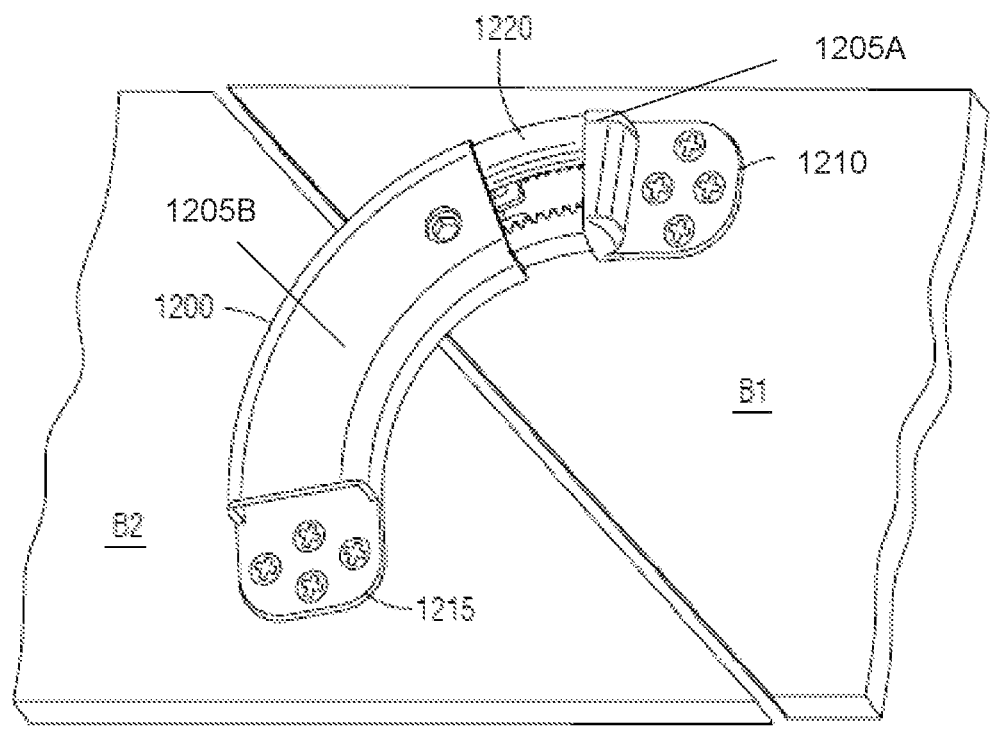
FIG. 13 illustrates a top view of the implant device in accordance with the sixth embodiment affixed to a bone.

FIG. 12 illustrates a top view of an implant device 1200 in accordance with sixth embodiment with a portion of the connection bridge transparent. FIG. 13 illustrates a top view of the implant device 1200 in accordance with sixth embodiment affixed to a bone. The implant device 1200 will also be described in relation to FIGS. 14A-14C. FIG. 14A illustrates a bottom perspective view of a portion of a the repositioning tool 1201 for one or more embodiments. FIG. 14B illustrates a bottom view of a portion of the repositioning tool 1201 of FIG. 14A. FIG. 14C illustrates an end view of the repositioning tool 1201 of FIG. 14A. The repositioning tool 1201 is curved but may function in a similar manner as described above in relation to implant device 100, 600, 800, 1200, etc.

The implant device 1200 may include a telescopic connection bridge 1205 to cause retraction or distraction of first and second bone segments B1 and B2, shown in FIG. 13. The telescopic connection bridge 1205 includes a first insertion structure 1205A connectable or mountable to the first bone segment B1 by fixation plate 1210 and a second insertion structure 1205B connectable or mountable to the second bone segment B2 by fixation plate 1215. The second insertion structure 1205B may have at least one of a pinion 1233 and a ratchet 1240. The first insertion structure 1205A has a ledge, guide, or rail 1230 insertable in the second insertion structure 1205B to interface with a pinion 1233 of the at least one pinion and a rack 1232 to interface with a ratchet 1240 of the at least one ratchet. The ratchet 1240 is insertable into the first insertion structure 1205A and selectively locks the first insertion structure 1205A to the second insertion structure 1205B. The ledge, guide, or rail 1230 and rack 1232 are separate and in stacked or adjacent relation. the ledge, guide, or rail 1230 may include a portion with teeth.

As shown in FIG. 14C, the ledge, guide, or rail 1230 includes a smooth ledge or rails 1239 along which an underside of the pinion 1233 travels. The pinion 1233 includes an upper gear element 1203 with teeth and a lower wheel element 1207. The diameter of the upper gear element 1203 is larger than the lower wheel element 1207. The diameter of the lower wheel element 1207 is dimensioned to fit between the rails 1239.

The prongs 1243 of the ratchet 1240 move in an out of the teeth or receptacle in the rack 1232. The ratchet 1240 may be connected to the pinion 1233 so that as the pinion 1233 rotates through the teeth or receptacle of the rack, the ratchet 1240 follows. The ratchet 1240 may include one cantilever arm. The lock mechanism (i.e., ratchet 1240) locks in or limits the translational motion to a predetermined measured growth in a direction associated with the translation motion provided by the pitch of the ratchet teeth rack (i.e., rack 1232), for example.

In this case, the outside ratchet curved beam and tip of the ratchet prong engages with the outside curved rail while the inside ratchet curved beam and tip of the ratchet prong engage with the inside curved rail. Again, each click of the ratchet achieves the desired amount of adjustment in only one direction. The top access to the pinion 1233 may be advantageous for most reduction/distraction situations since only a small access point is needed through the skin during the procedure.

In the case of the curved implant device, a single cantilevered ratchet leaf spring can be used on the inside or outside radius of the telescoping curvature. It can also be on the opposite side of the rack and pinion adjustment further reducing the footprint of the device. A curved slide switch can be employed similar to the straight slide switch previously described that is used to disengage and re-engage the ratchet prong with its ratchet teeth or ratchet receptacle upon demand.

FIG. 15A illustrates a perspective view of the implant device 1500 in accordance with a seventh embodiment in a first position. FIG. 15B illustrates a perspective view of the implant device 1500 in accordance with a seventh embodiment in a second position. FIG. 15C illustrates a perspective view of the implant device 1500 in accordance with a seventh embodiment in a third position. Part of the threads ride in a smooth track while the other part of the threads engage with the matching opposite thread pattern. FIG. 15D illustrates a perspective view of the implant device 1500 in accordance with a seventh embodiment in a fourth position.

Figure 16:
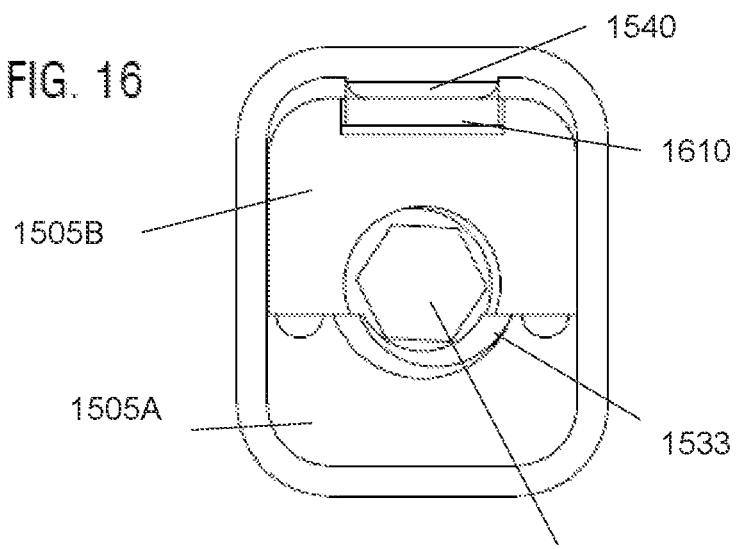
FIG. 16 illustrates an end view of the implant device in accordance with the seventh embodiment.
Figure 17:
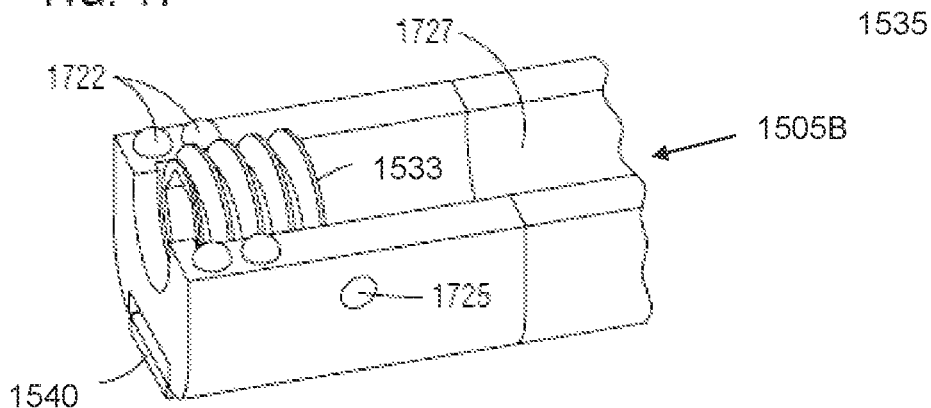
FIG. 17 illustrates a partial view of the implant device in accordance with the seventh embodiment.
Figure 18:
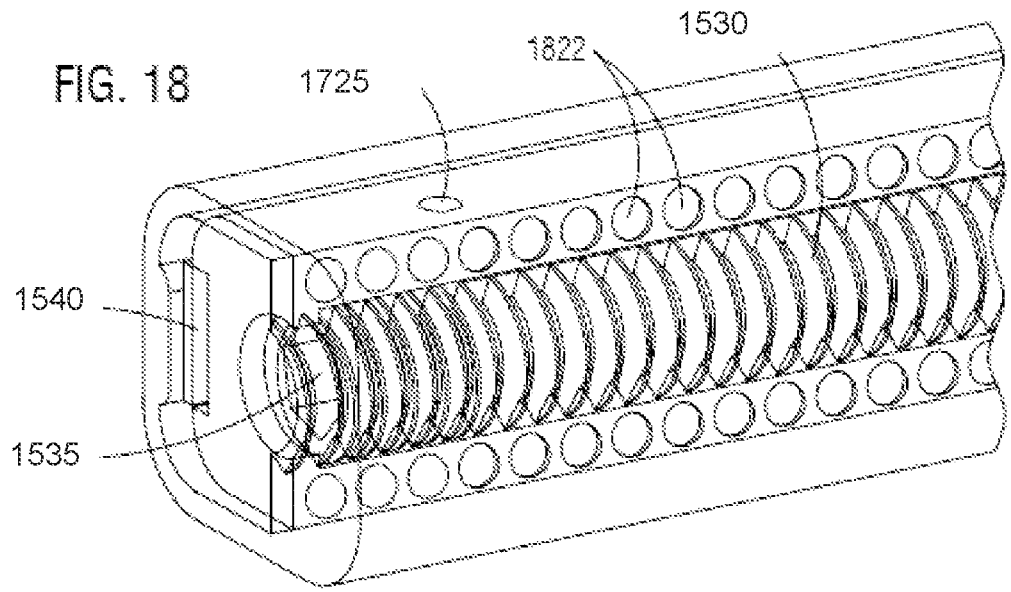
FIG. 18 illustrates a partial view of the implant device in accordance with the seventh embodiment.
Figure 19:
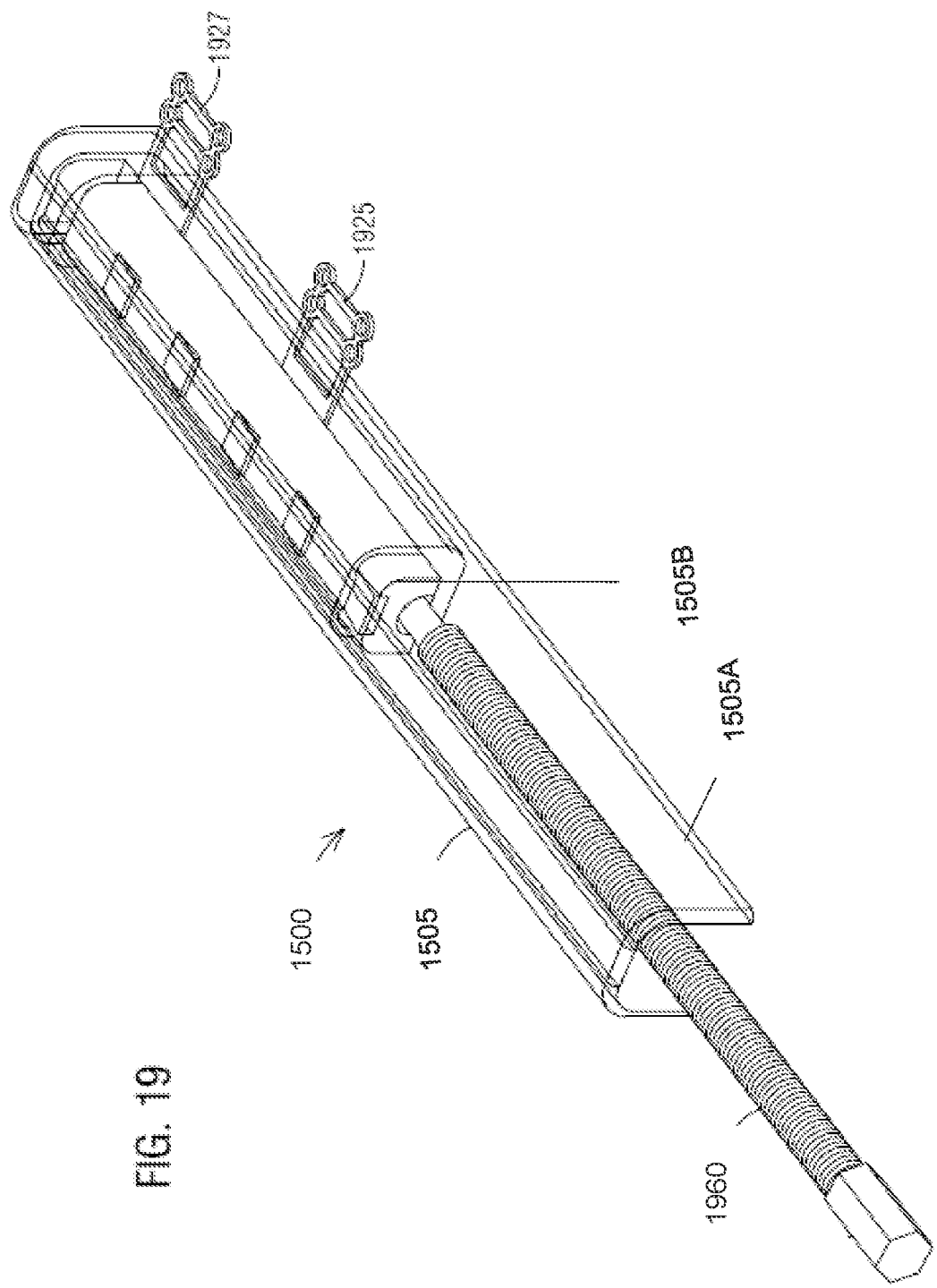
FIG. 19 illustrates a perspective of the implant device in accordance with the seventh embodiment.

Features of the implant device 1500 are also shown in FIGS. 16-19. FIG. 16 illustrates an end view of the implant device 1500 in accordance with a seventh embodiment. FIG. 17 illustrates a partial view of the implant device 1500 in accordance with a seventh embodiment. FIG. 18 illustrates a partial view of the implant device 1500 in accordance with a seventh embodiment. FIG. 19 illustrates a perspective of the implant device 1500 in accordance with a seventh embodiment.

The implant device 1500 includes a telescopic connection bridge 1505 to cause retraction or distraction of first and second bone segments. The telescopic connection bridge 1505 includes a first insertion structure 1505A and a second insertion structure 1505B connectable to the bone segments so that a repositioning tool 1501 produces a force to cause retraction or distraction therebetween. The first insertion structure 1505A has at least one gear or pinion 1533 and at least one ratchet 1540. The first insertion structure 1505A has a first rack 1530 insertable in the second insertion structure 1505B to interface with a gear or pinion 1533 and a second rack 1532 to interface with prongs of the ratchet 1540. The ratchet 1540 is insertable into the first insertion structure 1505A and selectively locks the first insertion structure 1505A to the second insertion structure 1505B. The first rack 1530 and second rack 1532 are separate and adjacent or in stacked relation. The flat leaf springs to keep the teeth engaged but allowing the pinion to compress so the detents can advance to the next receptacles.

The implant device 1500 includes a repositioning tool 1501. The repositioning tool 1501 includes the rack 1530 and the gear or pinion 1533. The repositioning tool 1501 also includes ratchet 1540 having cooperative ratchet elements or prongs 1722 (FIG. 17). The prongs may be detents. The ratchet 1540 may include leaf springs that engage the threads and spaced detents. The repositioning tool 1501 includes a rack 1532 with ratchet dents 1822 (FIG. 18) or receptacles. The rack 1530 may include a threaded rack. The repositioning tool 1501 has a worm gear configuration where the gear or pinion 1533 may be a worm gear with threads. The rack 1530 may include a threaded rack arrangement. In this configuration the keyhole 1535 is accessible from a side or end instead of a top access, such that gear or pinion 1533 rotates within rack 1530. The spring 1610 of the ratchet 1540 and prongs 1722 work in concert to lock and unlock the first and second insertion structures of the bridge 1505. The ratchet 1540 has an inclined tab biased by the spring 1610 in a raised position. The prongs 1722 click in and out of the ratchet dents 1822.

Referring now to FIG. 16, the ratchet 1540 includes at least one spring 1610. When the spring 1610 is depressed during adjustment, driving the telescoping length increase, the gear's screw threads remain partially engaged in the first rack 1530. The ratchet detents are on both sides or adjacent to the first rack 1530. The implant device 1500 includes at least one spring, which holds the ratchet detents in receptacles of the second rack 1532. The keyhole 1535 is shown to access the gear or pinion 1533.

As shown in FIGS. 17-18, the second insertion structure 1505B may have an adjustment screw retaining pin 1725 which holds the adjustment gear or pinion in position without restricting rotation. The second insertion structure 1505B includes a linear structure with a trough 1727 having a smooth surface.

Referring now to FIG. 19, the implant device 1500 includes a foot mounts 1925 and 1927. These mounts connect the first insertion structure 1505A to a first bone segment, and the second insertion structure 1505B to a second bone segment. The implant device 1500 may be used in a repair system that includes a handle 1960 keyed to the keyhole. The housing cover of the connection bridge 1505 encloses the telescoping action. The handle 1960 has one end mated to engage the keyhole 1535 so that rotation of the handle causes the gear or pinion 1533 to rotate to telescope or retract the first insertion structure 1505A relative to the second insertion structure 1505B.

The implant device 1500 may be connected to another implant device 1500 via a rack and pinion adapter, as will be described in more detail in relation to FIGS. 20-22.

FIG. 20 illustrates a perspective view of a repair system 2000 with two implant devices 1500A and 1500B joined together in accordance with an eight embodiment. Since the implant devices 1500A and 1500B are essentially the same as the implant device 1500, only the differences will be described. The implant device 1500A pivotally coupled to the implant device 1500B via a rack and pinion adapter 2049, as will be described in more detail in relation to FIG. 21.

FIG. 21 illustrates a rack and pinion adapter 2049 in accordance with an eight embodiment. The adapter 2049 has a first adapter 2057A that includes a first connector 2060 and a notch 2025. The first adapter 2057A connects to an end of the second insertion structure 1505B of implant device 1500A. The second insertion structure 1505B of implant device 1500A has a first adapter 2027 on a distal end. The adapter 2049 has a second adapter 2057B that includes to connector to connect to first adapter 2027 at the end of the second insertion structure 1505B of implant device 1500B.

The adapter 2049 includes a rack 2028 and a gear 2006. The gear 2006 is within the first housing 2004 of the connector 2060. The second adapter 2057B has a goose neck or curved neck with the rack 2028 arranged along the curvature of the goose neck 2010 or curved neck. The notch 2025 receives a portion 2014 of the goose neck 2010 such that as the gear 2006 rotates, the rack is feed through the notch 2025 in a first direction or a second direction based on the gear's rotation. The gear may be rotated by a tool (not shown).

FIG. 22 illustrates a perspective view of a system 2200 with at least two implant devices 1500A and 500B joined together in accordance with an eight embodiment. The embodiment joins two straight distractor/retractor implant devices with a curved adapter 2049.

FIG. 23A illustrates a perspective view of a system 2300 with at least two implant devices 1500A and 1500B joined together in a first position. FIG. 23B illustrates a perspective view of a system 2300 with at least two implant devices 1500A and 1500B joined in a second position. The distraction or retraction may be controlled by handles 1960 (FIG. 19).

Figure 24:
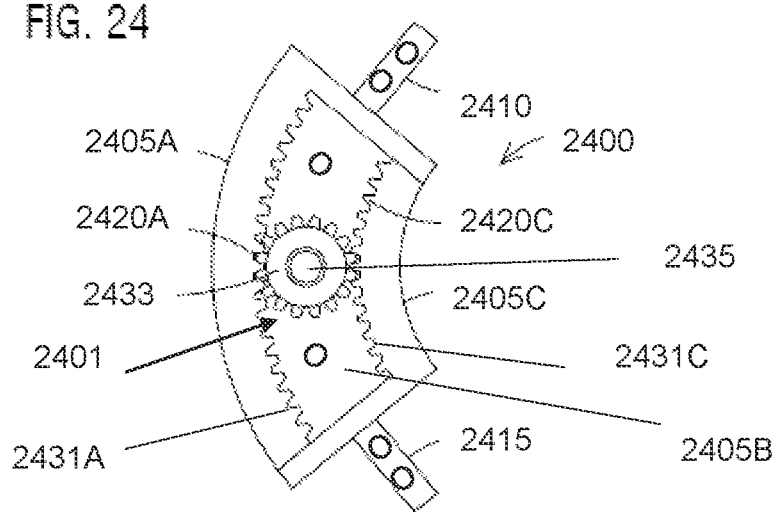
FIG. 24 illustrates a perspective view of the implant device in accordance with a ninth embodiment in a first position.
Figure 25:
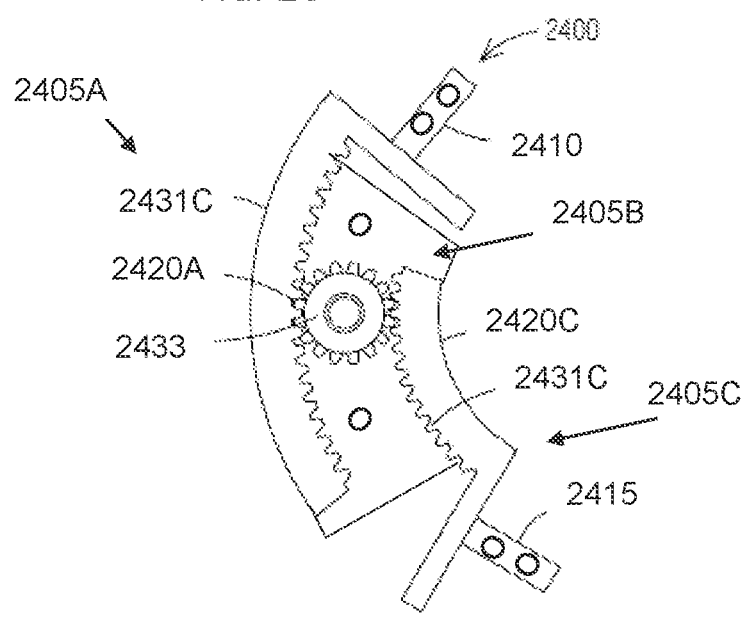
FIG. 25 illustrates a top view of an implant device of FIG. 24 in a second position.

FIG. 24 illustrates a perspective view of the implant device 2400 in accordance with a ninth embodiment in a first position. FIG. 25 illustrates a top view of an implant device of FIG. 24 in a second position. To prevent overcrowding in the figures, some of the components have been omitted. The implant device 2400 is similar to the implant device 1000. The first fixation plate 2410 is linear or angled relative to the center of rotation of the pinion 2433. The second fixation plate 2415 is linear or angled relative to the center of rotation of the pinion 2433.

The first insertion structure 2405A includes a guide structure 2420A that is similar to guide structure 1020A but in this instance, the guide structure 2420A includes a first curved rack portion 2431A with a rack of teeth. Here the guide rail has been omitted compared to the structure of implant device 1000. The second insertion structure 2405B includes the repositioning tool 2401. The repositioning tool 2401 includes a pinion 2433 and a ratchet (not shown). The ratchet connected to a curved rack is shown in FIGS. 12 and 13, for example. The second insertion structure 2405B includes a housing which supports the pinion and the keyhole 2435. The housing of the second insertion structure 2405B is fastened to a bone segment.

The second insertion structure 2605B has inner guide walls to keep the curved insertion structure with the engaging rack and straight insertion structure with the engaging rack along their expected displacement paths.

The third insertion structure 2405C includes a guide structure 2420C that is similar to guide structure 1020C. The guide structure 2420C includes a first curved rack portion 2431C with a rack of teeth. The guide rail is omitted. The third insertion structure 2405C includes a fixation plate 2415 which is curved or angled.

In this embodiment, the pinion 2433 engages both first curved rack portion 2431A and first curved rack portion 2431C, simultaneously, to telescope (cause distraction) or retract (cause retraction). The pinion 2433 is a sun gear. The first curved rack portion 2431A is a ring gear. The first curved rack portion 2431C is a sun gear.

FIG. 26A illustrates a perspective view of the implant device 2600 in accordance with a tenth embodiment in a first position and with the interior components shown. FIG. 26B illustrates a perspective view of the implant device 2600 in accordance with a tenth embodiment in a first position.

The implant device 2600 can be used in angled or curved reduction or distraction situations. Again, a rack 2630 and pinion 2633 of a reposition tool 2601 with a top access has been employed with an inline ratchet (not shown) to control the increment of adjustment following the curvature of the guide structure 2620A and guide structure 2620C.

Figure 27:
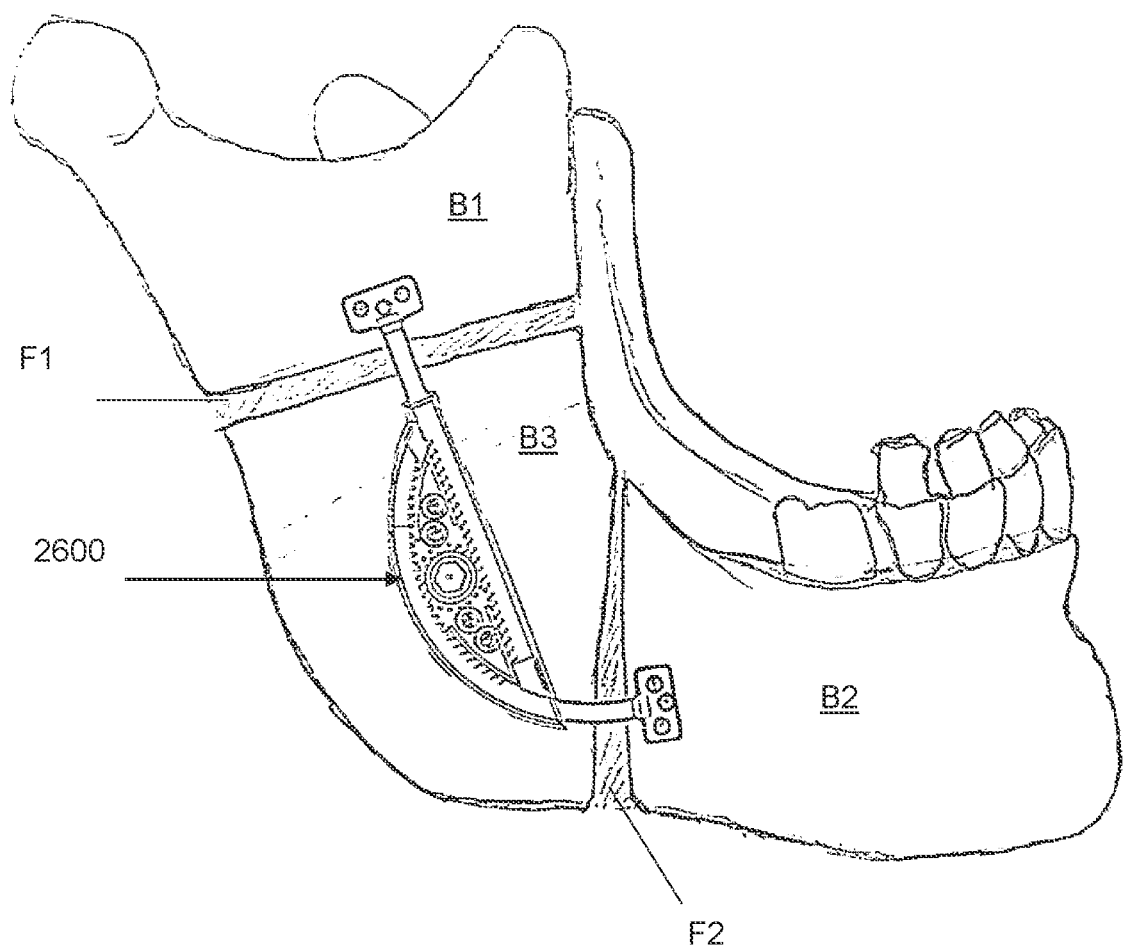
FIG. 27 illustrates the implant device implanted first, second and third bone segments.

The telescopic connection bridge 2605 includes a first insertion structure 2605A connectable to the first bone segment. The telescopic connection bridge 2605 includes a second insertion structure 2605B and a third insertion structure 2605C. The third insertion structure 2605C may be connected to a second bone segment. The second insertion structure 2605B may be connected to a third bone segment located between the first bone segment and the second bone segment, as shown in FIG. 27.

The second insertion structure 2605B may have at least one pinion 2633 and at least one ratchet (i.e., ratchet 140) (not shown). The second insertion structure 2605B also includes features similar to second insertion structure 105B and will not be repeated. However, in this configuration, the second insertion structure 2605B is stationary while the first and third insertion structures move relative to the second insertion structure from opposite sides of the second insertion structure. The second insertion structure 2605B may be fastened to a bone segment.

The first insertion structure 2605A includes guide structure 2620A that is similar to guide structure 120. By way of example, in this instance, the guide structure 2620A includes a first linear rack portion 2631A with a rack teeth. The first insertion structure 2605A includes first fixation plate 2610 which is curved, straight or angled. The first fixation plate 2610 includes receptacles to receive bone fasteners. In this view, the first fixation plate 2610 is connected to an end of an arm 2611 inline and integrated with the first linear rack portion 2631A. The first insertion structure 2605A includes the arm 2611, the guide structure 2620A and first fixation plate 2610 which are movable relative to the second insertion structure 2605B in response to turning of the repositioning tool.

The third insertion structure 2605C includes guide structure 2620C that is similar to guide structure 120. However, the guide structure 2620C is curved. The guide structure 2620C includes a first curved rack portion 2631C with a rack teeth. The third insertion structure 2605C includes fixation plate 2615 which is curved, straight or angled. In this view, the fixation plate 2615 is connected to an end of an arm 2616 inline and integrated with the curved rack portion 2631C. The third insertion structure 2605C includes the arm 2616, the guide structure 2620C and first fixation plate 2615 which are movable relative to the second insertion structure 2605B.

The second insertion structure 2605B may include a housing 2660 to support and house the repositioning tool 2601 with top access using the keyhole 2635 to the pinion 2633. The housing 2660 includes opening 2661 and 2662 through which arms 2611 and 2616, respectively, telescope or retract. The housing 2660 includes a linear edge following the profile of the guide structure 2620A and a curved edge following the profile of the guide structure 2620C. The housing 2660 may be fastened to a bone segment via fasteners 2666. The housing may include a cover, which may be removable. One or more fasteners 2666 may be secure the cover to the housing. The housing 2660 may include a fixation plate for attaching the second insertion structure 2605B to the bone segment. The fixation plate may be a bottom surface of housing 2660, in some instances or may radiate from edges of the housing, as shown in FIG. 9A.

FIG. 26C illustrates a perspective view of the guide structure in accordance with a tenth embodiment in a first position and a second position. In this embodiment, the pinion 2633 engages both first linear rack portion 2631A and first curved rack portion 2631C, simultaneously, to telescope (cause distraction) or retract (cause retraction) simultaneously of the first insertion structure 2605A and the third insertion structure 2605C. As the first linear rack portion 2631A and first curved rack portion 2631C move, each applies a force to distract or retract bone segments relative to the other.

The embodiment of FIGS. 26A-26C retracts or distracts simultaneously in two different directions, one linear and one curved. It should be understood, that replacing the rack teeth of the first linear rack portion 2631A causes, the embodiment of FIGS. 26A-26C to move in a curved direction only.

Although one rack is linear and the other is curved, the telescoping between the first insertion structure and the second insertion structure may be in a first curved or linear direction; and the telescoping between the second insertion structure and the third insertion structure may be in a second linear or curved direction depending on whether the racks are linear or curved.

Accordingly, the implant device 2600 may be modular so that the surgeon can select the parts needed for the particular surgery. For example, the first insertion structure 2605A with rack teeth may be replaced with a first insertion structure 2605A without rack teeth.

FIG. 27 illustrates the implant device 2600 implanted first, second and third bone segments B1, B2 and B3. In this example, bone segment B1 is the ramus below the mandibular notch. The second bone segment may be the body after the angle of mandible. The third bone segment B3 may be a portion of the mandible between the fractures F1 separating segments B1 and B3 and fracture F2 separating B2 and B3.

Figure 28A:
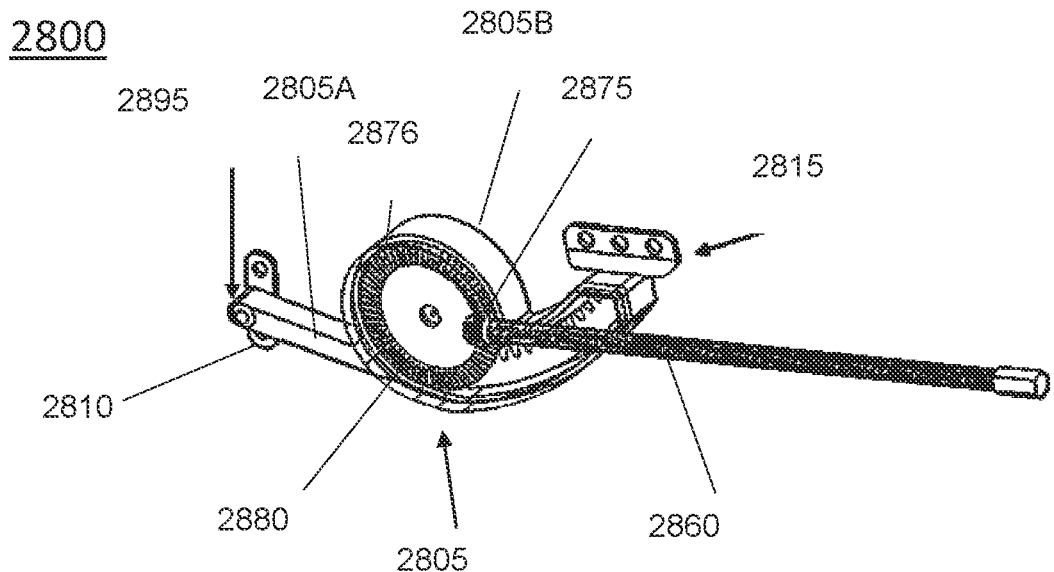
FIG. 28A illustrates a front view of an implant device according to an eleventh embodiment.
Figure 28B:
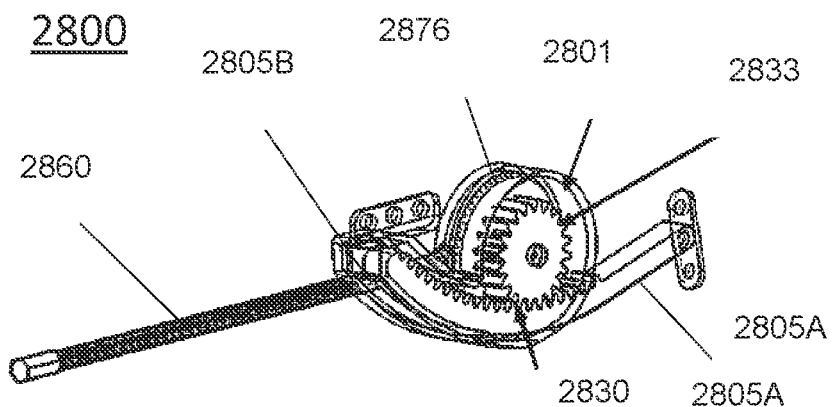
FIG. 28B illustrates a back view of an implant device according to the eleventh embodiment.
Figure 28C:
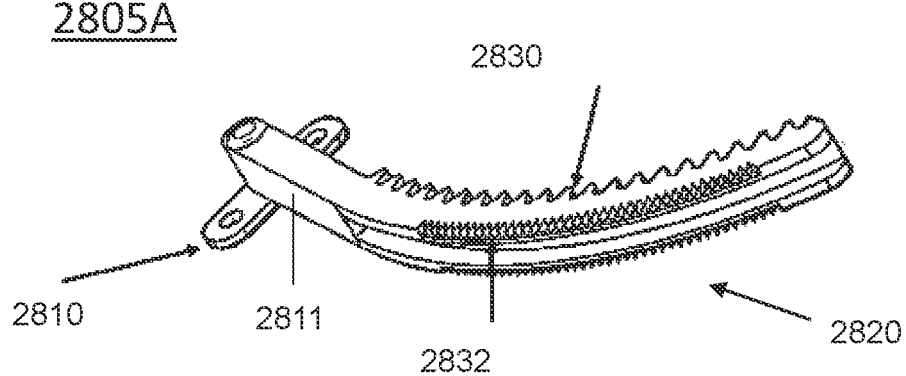
FIG. 28C illustrates a perspective view of the first insertion structure of FIG. 28A.
Figure 28D:
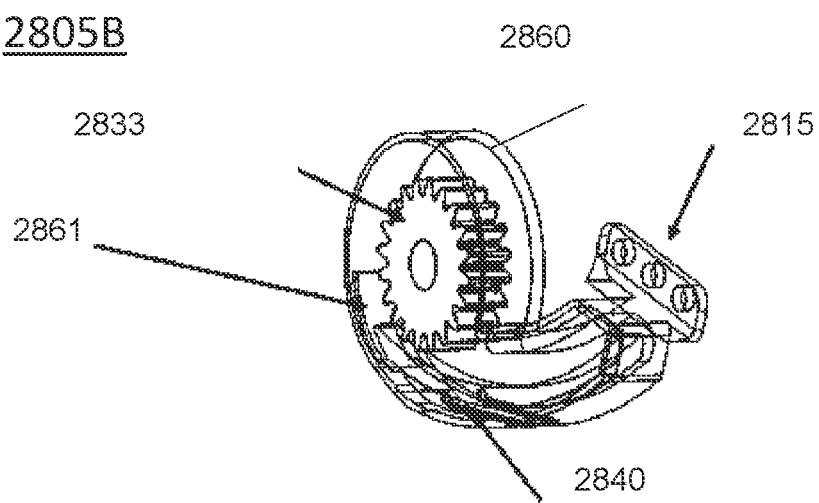
FIG. 28D illustrates a perspective view of the second insertion structure of FIG. 28A.

FIG. 28A illustrates a front view of an implant device 2800 according to an eleventh embodiment. FIG. 28B illustrates a back view of an implant device 2800 according to an eleventh embodiment. FIG. 28C illustrates a perspective view of the first insertion structure 2805A of FIG. 28A. FIG. 28D illustrates a perspective view of the second insertion structure 2805B of FIG. 28A.

The implant device 2800 is similar to the implant device 600 of FIGS. 6A-6B previously described. Thus, only the differences will be described in detail. The implant device 2800 may include a built-in adjustment tool 2880 having a handle 2860. The built-in handle 2860 may be mounted to the connection bridge 2805. The adjustment tool 2880 may include an interface, such as a first gear 2875, at one end of the handle 2860 coupled to the repositioning tool 2801, such that rotation of the built-in handle causes the translational motion. The first gear 2875 interfaced with gear or teeth 2876 adjacent to pinion 2833, such that form a miter gear configuration.

In this configuration, the access to the repositioning tool 2801 may be from the side of the connection bridge and not directly perpendicular to the to the translational motion of the first insertion structure 2805A, for example.

In FIG. 28C, the guide structure 2820 is shown with a curvature configuration. In this example, the first rack 2830 may be positioned on an interior curvature of the guide structure. The second rack 2832 may be positioned along an exterior surface of the curvature of the guide structure 2820. As can be seen, in some embodiments, the pitch or separation of the teeth of the first rack is different from the pitch or separation of the teeth of the second rack. In this configuration, the first insertion structure 2805A includes an arm 2811 between the guide structure 2820 and fixation plate 2810. By way of example, at least one fixation plate may be connected to an arm (i.e., arm 2811) via a swivel connection 2895.

The connection bridge 2805 of the implant device 2800 has a circular portion housing 2860 with an open end 2961 (FIG. 28D). The connection bridge 2805 includes a narrowed housing with a cavity projecting in a direction toward a bone section. As shown in FIG. 28D, the lock mechanism (i.e., ratchet) 2840 is shown mounted in the housing of the connection bridge 2805. The connection bridge 2805 includes fixation plates 2810 and 2815 which are in different planes.

Figure 29A:
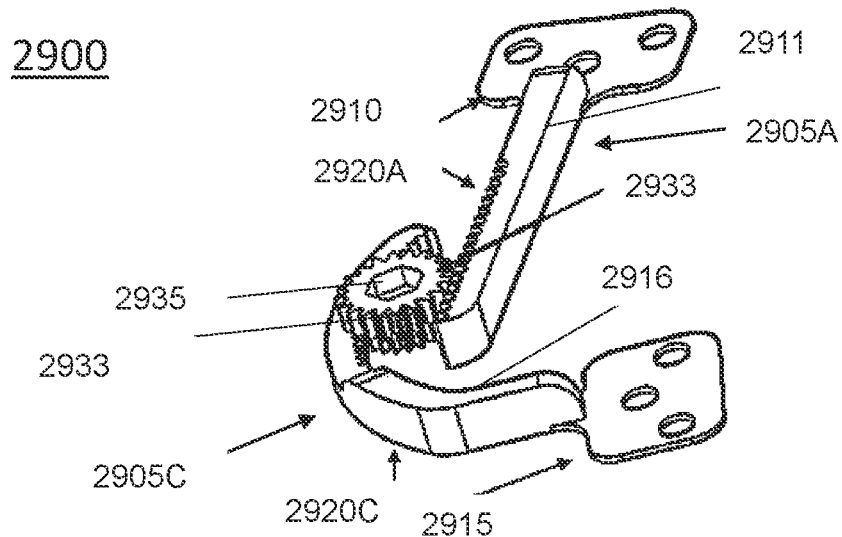
FIG. 29A illustrates a top view of a portion of the implant device with multiple pinions.
Figure 29B:
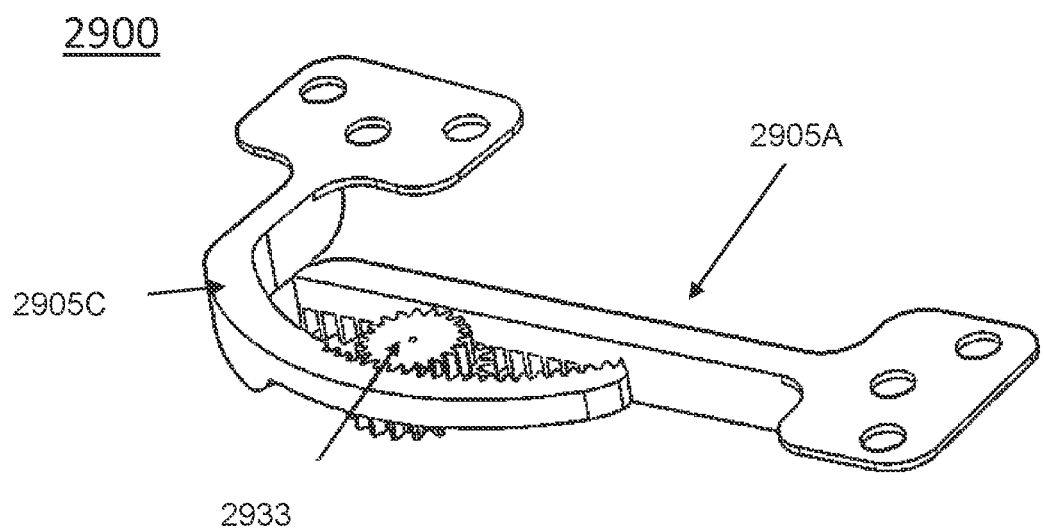
FIG. 29B illustrates a bottom view of a portion of the implant device with multiple pinions.

FIG. 29A illustrates a top view of a portion of the implant device 2900 with multiple pinions 2933. FIG. 29B illustrates a bottom view of a portion of the implant device 2900 with multiple pinions 2933. The configuration of implant device 2900 is double translational motion action. The pinions 2933 are in stacked relation and may share the same access point, such as keyhole 2935, for example. The first insertion structure 2905A includes the guide structure 2920A and fixation plate 2910 and arm 2911. The pinions 2933 are housed in the second insertion structure. The third insertion structure 2905C includes the guide structure 2920C and fixation plate 2915. The guide structure 2920A has a curved configuration. The guide structure 2920C has a curved configuration. The translation motion of the guide structures 2920A and 2920C may be simultaneous.

In FIG. 29A, the third insertion structure 2905C includes an arm 2916 between the guide structure 2920C and fixation plate 2915. The arm 2916 may have a V-shape or L-shape. As shown in FIG. 29C, the third insertion structure 2905C may have a C-shape.

FIG. 30A illustrates a top view of an implant device 3000A with a built-in adjustment handle or tool. FIG. 30B illustrates a top view of an implant device 3000B with a built-in adjustment handle or tool. The implant device 3000A and 3000B are essentially the same as implant device 2800. In this instance, section 3010 for designing an arm and fixation plate may originally be blank but then designed using the VSP tool 3644 (FIG. 36) to have the design of FIG. 2800, including forming a curvature in section 3010, for example.

Figure 31:
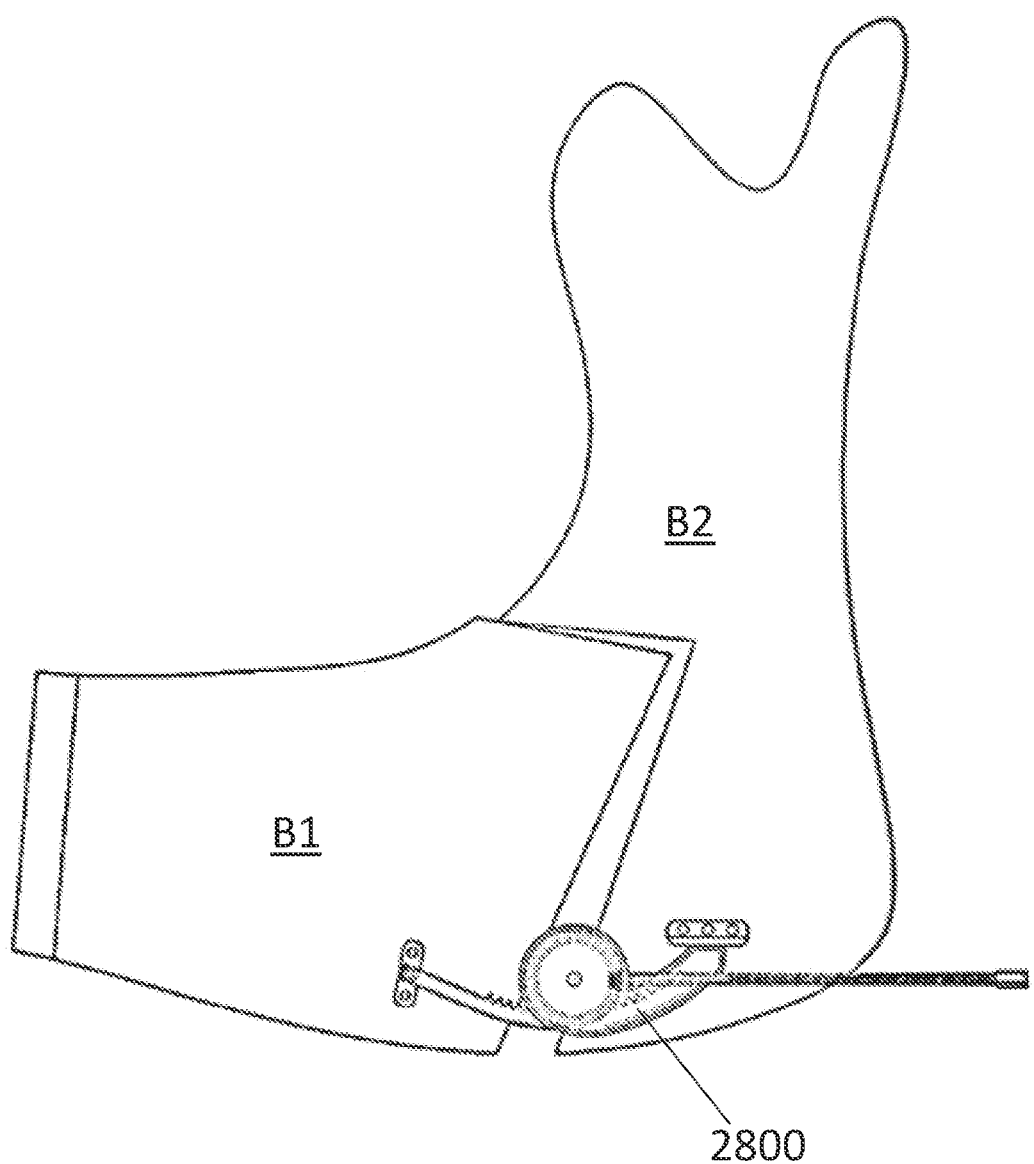
FIG. 31 illustrates the implant device installed on bone segments.

FIG. 31 illustrates the implant device 2800 installed on the outer surfaces of bone segments B1 and B2 of the mandibular.

Figure 32:
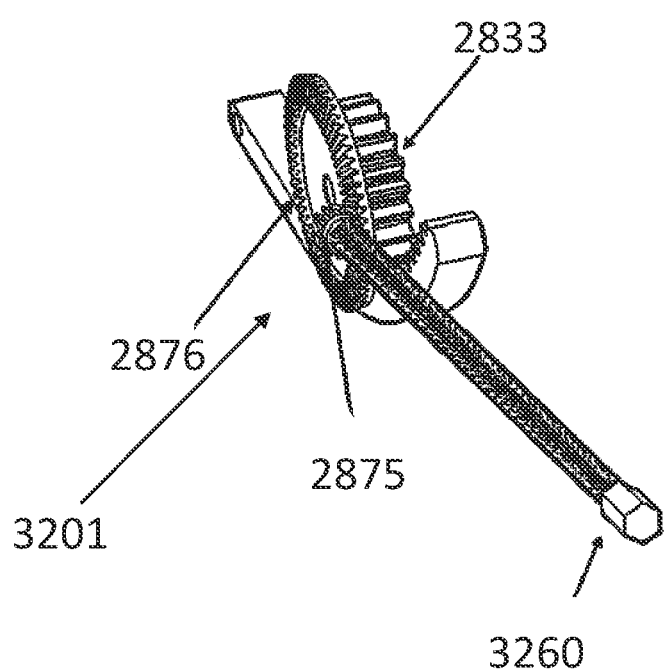
FIG. 32 illustrates an adjustment handle of an integrated adjustment tool of an implant device.

FIG. 32 illustrates an adjustment handle 3260 of an integrated adjustment tool 3280 interfaced with a repositioning tool 3201 of an implant device such that access is from the side. For example, the pinion 2833 rotates in a first direction which the interface or first gear 2875 rotates orthogonal to the first direction. The gear or teeth 2876 adjacent to pinion 2833 engages gear 2875.

Figure 33:
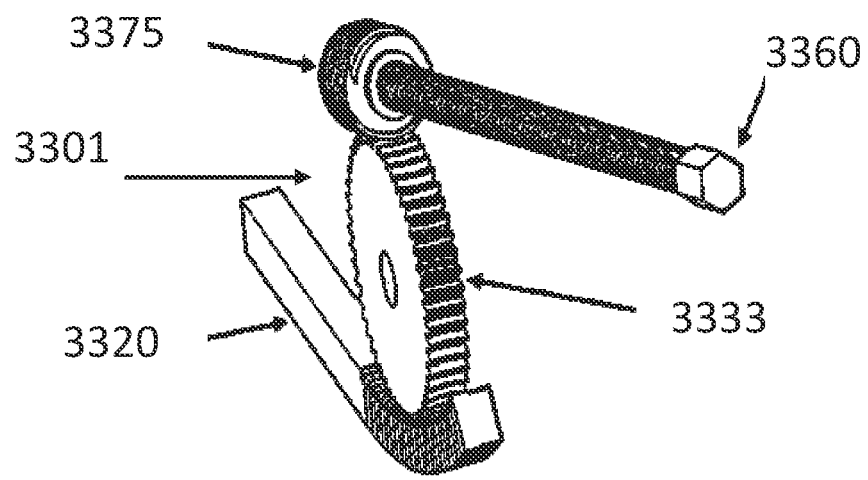
FIG. 33 illustrates an adjustment handle of an integrated adjustment tool of an implant device.

FIG. 33 illustrates an adjustment handle 3360 of an integrated adjustment tool 3380 interfaced with a repositioning tool 3301 of an implant device. For example, the pinion 3333 rotates in a first direction which the interface or first gear 3375. The pinion 3333 engages the guide structure 3320 and rotates. As the handle 3360 rotates, the interface or first gear 3375 rotates.

Figure 34:
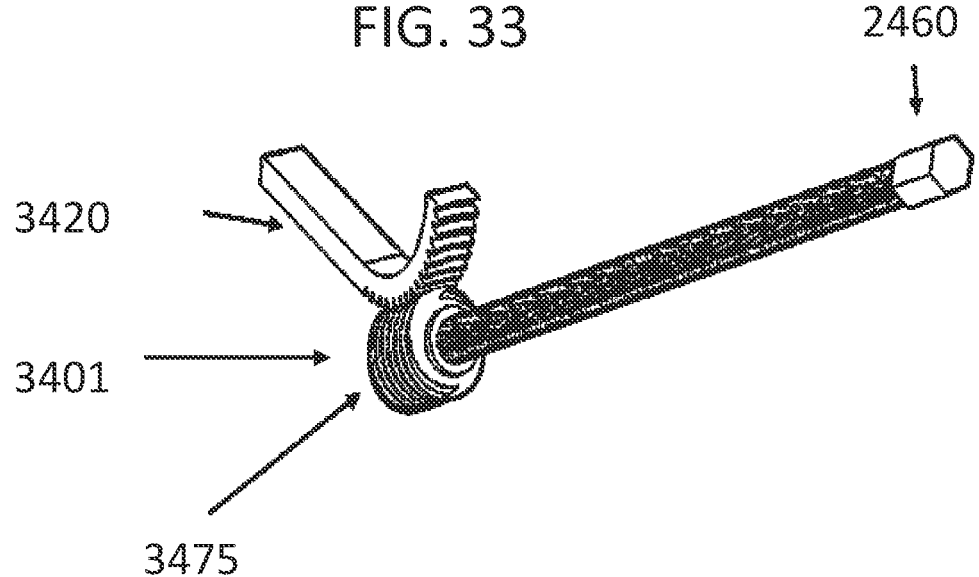
FIG. 34 illustrates an adjustment handle of an integrated adjustment tool of an implant device.

FIG. 34 illustrates an adjustment handle 3460 of an integrated adjustment tool 3480 interfaced with a repositioning tool 3401 of an implant device. As the handle 3460 rotates, the interface or first gear 3475 rotates along the guide structure 3420.

Figure 35:
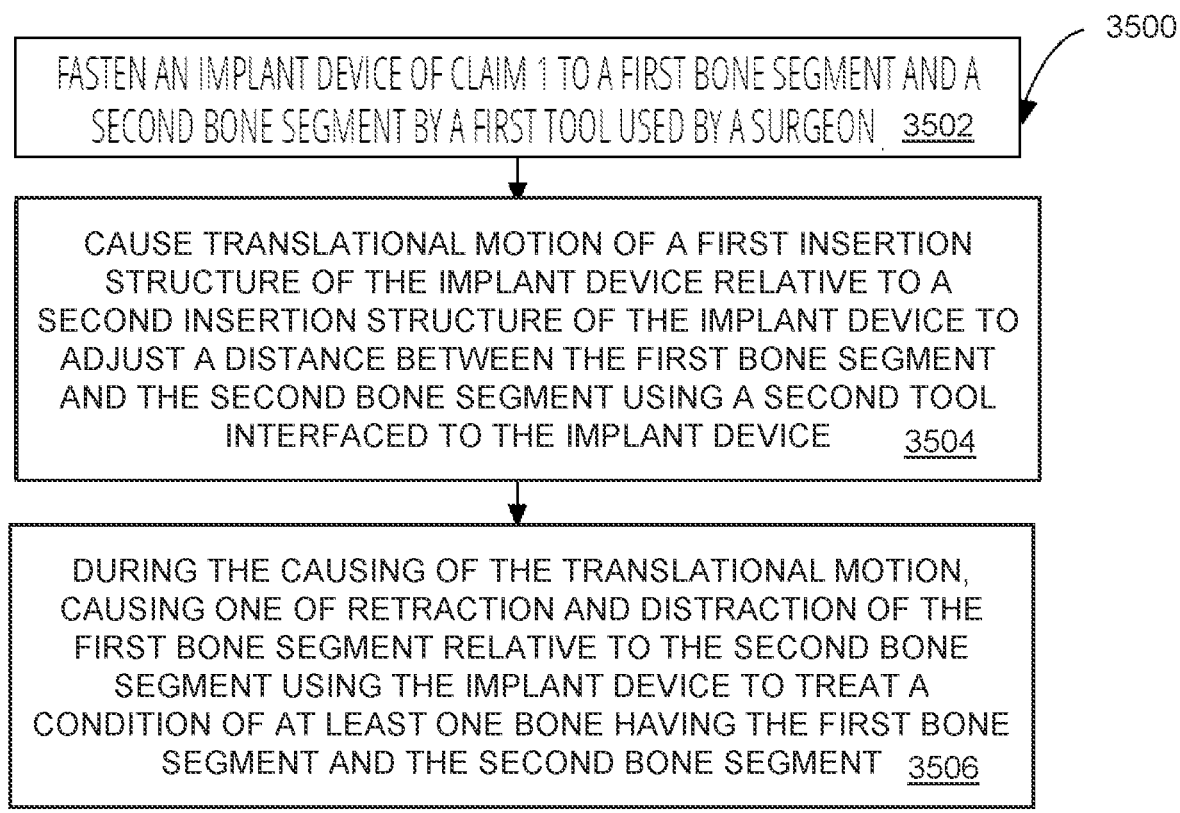
FIG. 35 illustrates a method to cause distraction or retraction using the implant device in accordance with one embodiment.

FIG. 35 illustrates a method 3500 to cause distraction or retraction using the implant device in accordance with one embodiment. In block 3502, method 3500 fastens an implant device 100, for example, to a first bone segment and a second bone segment by a first tool (i.e., tool 565) used by a surgeon. In block 3504, method 3500 causing translational motion of a first insertion structure of the implant device relative to a second insertion structure of the implant device to adjust a distance between the first bone segment and the second bone segment using a second tool interfaced to the implant device. In block 3506, method 3500 during the causing of the translational motion, causing one of retraction and distraction of the first bone segment relative to the second bone segment using the implant device to treat a condition of at least one bone having the first bone segment B1 and the second bone segment B2.

An embodiment of a method for repairing a bone fracture utilizing the embodiments is disclosed herein. The steps include determining the strategy of repair which includes selecting a best access, incisions locations, a fixation or distraction assembly, build and tools. Next, creating the incisions need to place the assembly. Next, locating the plates as necessary and then install the plates by drilling bone holes using access tools and installing the fasteners.

After the initial position of the implant device and fastening to the bone, the next step is to close the incisions once the installation of the implant device is complete.

The treatment of a condition of the bone may take many weeks. For example, distraction of bone segments may start days 3-5 after regenerate forms. The implant device may cause distraction 0.5 mm every 12 hours, which equals about 1 mm per day for X #days depending on length needed. The value of X may be 10-21 days. However, X may be longer or shorter depending on the treatment needed. This is followed by 8 weeks of consolidation. Then, the implant device is removed. So, the treatment in some instances is about 10-12 weeks total depending on length needed.

In other instances, based on the bone condition, age of the patient, the treatment may be longer or shorter. Also, the amount of distraction needed will vary, thus increasing or decreasing the treatment time. For example, if the amount of adjustment is 4 mm. It may require 4 days for the distraction, phase. The number of weeks needed for consolidation may vary also based on the patient's demographics and/or bone condition.

The embodiments disclosed herein such as the implant device may be used with a Virtual Surgical Planning (VSP) tool configured to bringing the hardware (implant device) into the virtual space and pre-planning the length, shape, bends, and types of mounting plates needed to repair or reconstruct the bone fracture or for the treatment of a bone condition. Once selected the plates may be pre-formed into the desired configuration, utilizing the friction fit/draft feature of the plate connectors, as a drop-in solution and the order of reduction and fixation with screws printed out as a surgical plan.

The system may include a Virtual Surgical Planning (VSP) tool. The VSP tool allows a surgeon or another to plan the implant device into a virtual space and pre-planning the length and types of plates needed to repair the injury. For example, for a mandible repair, the VSP tool may be used to design the profile of the implant device for a patient specific curved distraction device for the patient's mandible. The VSP tool may use an image of the patient's mandible.

The surgeon or another may use the VSP tool to design the implant device using a before and after bone segment positions from the image using medical imaging techniques of the bone segments to define a path for the translational motion. The imaging techniques may include radiographic imagery, X-rays, fluoroscopy, computed tomography (CT) scan, and magnetic resonance imaging (MRI), for example.

During VSP, the original mandible would (in the virtual world), for example, receive, for example, an inverted L-Cut osteotomy bilaterally. Virtually, the detached (front) half would be suspended in space, in its desired final distracted position (both anteriorly—in line with the upper front teeth—and angled up to close the bite). Then, simply. we would identify the two mounting positions (one on posterior base and one on anterior to-be-distracted bone surface). We assume that the bone grows in straight increments from start to finish. We just make the distraction arm connect point A to point B in its resulting distraction path (considering the pre-distracted position and the post-distracted position in 3D space). The left distractor would be the mirror image of the right distractor and in this way, at least in theory, the forces work be as equal/opposite and uniform as possible, and thus, we would achieve the most efficient bilateral distraction path to the front mandible's final position . . . we would build this path into our patient specific, additively manufactured, device plus the specific patient's anatomical contours into the housing and mounting brackets. The cutting guides for the patient specific osteotomy would be manufactured as described in the previously sent article.

Prior to fastening the implant device, at 3502, the method 3500 may include using a virtual surgical planning tool to design the implant device using a before and after bone segment positions of an image of the bone segments to define a path for the translational motion.

An embodiment of a method for repairing a bone fracture utilizing the embodiments is disclosed herein. The steps include determining the strategy of repair which includes selecting a best access, incisions locations, a fixation plate assembly, build and tools. Next, creating the incisions need to place the fixation plates of the implant device. Next, locating the fixation plates and implant device as necessary and then install the fixation plates of at least one insertion structure by drilling bone holes using flexible access tools and installing the fasteners.

Locating or mounting the fixation plates of the implant device includes attaching (by installing cortical screws). After a first one of the insertion structures is mounted to a bone segment, the other insertion structure may be inserted to make two of the insertion structures together. The location of the inserted structure may be adjusted by controlling the repositioning tool before mounting the insertion structure to an outer surface of the bone segment.

In some embodiments, implant components of the osseous repair system 500A may be fabricated from medical grade metals such as titanium, stainless steel, cobalt chrome, and alloys thereof. The osseous repair system 500A may be fabricated using biocompatible implant material having high tensile strength and biocompatible properties for implantation in a human, animal or synthetic structure.

Additionally, the implant components can be at least partially fabricated from a shape memory metal, for example Nitinol, which is a combination of titanium and nickel. Such materials are typically radiopaque, and appear during x-ray imaging, and other types of imaging. Portions of the implant components can also be fabricated from medical grade biocompatible polymers, copolymers, blends, and composites of polymers. The polymers, copolymers, blends, and composites of polymers may be radiolucent and do not appear during x-ray or other types of imaging.

Referring now to FIG. 36, in a basic configuration, a computing device 3600 which may include any type of stationary computing device, server or a mobile computing device for planning the surgery and designing the configuration of the implant device for a particular patient's bone structure.

The computing device 3600 may include one or more processing devices 3606 and system memory in a hard drive. Depending on the exact configuration and type of computing device 3600, system memory may be volatile (such as RAM 3602), non-volatile (such as read only memory (ROM 3604), flash memory, and the like) or some combination of the two. A system memory may store an operating system, one or more applications, and may include program data providing the VSP tool 3644.

The computing device 3600 may carry out one or more blocks/steps of a process described in relation to FIGS. 1 and 2. The computing device 3600 may also have additional features or functionality. As a non-limiting example, the computing device 3600 may also include additional data storage media devices 3608 (removable and/or non-removable) such as, for example, magnetic disks, optical disks, or tape. The computer storage media devices 3608 may include volatile and non-volatile, non-transitory, removable, and non-removable media implemented in any method or technology for storage of data, such as computer readable instructions, data structures, program modules or other data. The system memory, removable storage and non-removable storage are all non-limiting examples of computer storage media 3610. The computer storage media 3610 may include, but is not limited to, RAM 3602, ROM 3604, Electrically Erasable Read-Only Memory (EEPROM), flash memory or other memory technology, compact-disc-read-only memory (CD-ROM), digital versatile disks (DVD) or other optical storage, magnetic cassettes, magnetic tape, magnetic disk storage or other magnetic storage devices, or any other physical medium which can be used to store the desired data and which can be accessed by computing device. Any such computer storage media may be part of device.

The computing device 3600 may also include or have input/output (I/O) interfaces 3612 for input modules 3664 such as a keyboard, mouse, pen, voice input device, touch input device, etc. The computing device may include or have I/O interfaces 3612 for connection to output device(s) such as a display, a presentation module 3616, speakers, etc. A graphical user interface (GUI) 3618 may be displayed on the presentation module 3616. The VSP tool 3644 may include user interfaces such as in the form of one or more GUIs to plan one or more of: the surgery, the translation motion of the implant device, the bone fixation points for the fasteners to connect the plates of the implant device to the bone segments, design the curvatures of the plates, the housing of the connection bridge, and the racks of repositioning tool, for example. The VSP tool may plan the lock mechanism.

The computing device 3600 may include a peripheral bus 3614 for connecting to peripherals. Computing device 3600 may contain communication connection(s) that allow the device to communicate with other computing devices, such as over a network or a wireless network. By way of example, and not limitation, communication connection(s) may include wired media such as a wired network or direct-wired connection, and wireless media such as acoustic, radio frequency (RF), infrared and other wireless media. The computing device 3600 may include a network interfaces 3620, such as a network interface card to connect (wired or wireless) to a network or other communication conduits 3622.

Computer program code for carrying out operations described above may be written in a variety of programming languages, including but not limited to a high-level programming language, such as C or C++, Python, Java, for development convenience. In addition, computer program code for carrying out operations of embodiments described herein may also be written in other programming languages, such as, but not limited to, interpreted languages. Some modules or routines may be written in assembly language or even micro-code to enhance performance and/or memory usage. It will be further appreciated that the functionality of any or all of the program modules may also be implemented using discrete hardware components, one or more application specific integrated circuits (ASICs), or a programmed Digital Signal Processor (DSP) or microcontroller. A code in which a program of the embodiments is described can be included as a firmware in a RAM, a ROM, and a flash memory. Otherwise, the code can be stored in a tangible computer-readable storage medium such as a magnetic tape, a flexible disc, a hard disc, a compact disc, a photo-magnetic disc, and a digital versatile disc (DVD).

The embodiments may be configured for use in a computer or a data processing apparatus which includes a memory, such as a central processing unit (CPU), a RAM and a ROM as well as a storage medium such as a hard disc.

The "step-by-step process" for performing the claimed functions herein is a specific algorithm, and may be shown as a mathematical formula, in the text of the specification as prose, and/or in a flow chart. The instructions of the software program create a special purpose machine for carrying out the particular algorithm. Thus, in any means-plus-function claim herein in which the disclosed structure is a computer, or microprocessor, programmed to carry out an algorithm, the disclosed structure is not the general-purpose computer, but rather the special purpose computer programmed to perform the disclosed algorithm.

A general-purpose computer, or microprocessor, may be programmed to carry out the algorithm/steps for creating a new machine. The general-purpose computer becomes a special purpose computer once it is programmed to perform particular functions pursuant to instructions from program software of the embodiments described herein. The instructions of the software program that carry out the algorithm/steps electrically change the general-purpose computer by creating electrical paths within the device. These electrical paths create a special purpose machine for carrying out the particular algorithm/steps.

Unless otherwise defined, all terms (including technical and scientific terms) used herein have the same meaning as commonly understood by one of ordinary skill in the art to which embodiments belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

"Communication media" typically comprise computer readable instructions, data structures, program modules, or other data in a modulated data signal, such as carrier wave or other transport mechanism. The communication media may also comprise any information delivery media. The term "modulated data signal" means a signal that has one or more of its characteristics set or changed in such a manner as to encode information in the signal. By way of example, and not limitation, communication media comprises wired media such as a wired network or direct-wired connection, and wireless media such as acoustic, infrared, and other wireless media. Combinations of any of the above are also included within the scope of computer readable medium.

Alternatively, or in addition, any of the functions described herein may be performed, at least in part, by one or more hardware logic components. For example, without limitation, illustrative types of hardware logic components that may be used include Field-programmable Gate Arrays (FPGAs), Application-specific Integrated Circuits (ASIC s), Application-specific Standard Products, System-on-a-chip systems, Complex Programmable Logic Devices, and the like.

The terms "module" and "component" as used herein generally represent software, firmware, hardware, or combinations thereof. In the case of a software implementation, the module or component represents program code that performs specified tasks when executed on a processor. The program code may be stored in one or more computer readable memory devices, otherwise known as non-transitory devices. The features of the embodiments described herein are platform-independent, meaning that the techniques can be implemented on a variety of commercial computing platforms having a variety of processors (e.g., set-top box, desktop, laptop, notebook, tablet computer, personal digital assistant (PDA), mobile telephone, smart telephone, gaming console, wearable device, an Internet-of-Things (IoT) device, and the like).

Unless otherwise defined, all terms (including technical and scientific terms) used herein have the same meaning as commonly understood by one of ordinary skill in the art to which embodiments of the invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

In particular, unless specifically stated otherwise as apparent from the discussion, it is appreciated that throughout the description, discussions utilizing terms such as "processing" or "computing" or "calculating" or "determining" or "displaying" or the like, refer to the action and processes of a computer system, or similar electronic computing device, that manipulates and transforms data represented as physical (electronic) quantities within the computer system's registers and memories into other data similarly represented as physical quantities within the computer system memories or registers or other such data storage, transmission or display devices.

The terminology used herein is for the purpose of describing particular embodiments only and is not intended to be limiting. As used herein, the singular forms "a," "an," and "the" are intended to include the plural forms as well, unless the context clearly indicates otherwise. Furthermore, to the extent that the terms "including," "includes," "having," "has," "with," or variants thereof are used in either the detailed description and/or the claims, such terms are intended to be inclusive in a manner similar to the term "comprising." Moreover, unless specifically stated, any use of the terms "first," "second," etc., does not denote any order or importance, but rather the terms "first," "second," etc., are used to distinguish one element from another. As used herein the expression "at least one of A and B," will be understood to mean only A, only B, or both A and B.

While various disclosed embodiments have been described above, it should be understood that they have been presented by way of example only, and not limitation. Numerous changes, omissions and/or additions to the subject matter disclosed herein can be made in accordance with the embodiments disclosed herein without departing from the spirit or scope of the embodiments. Also, equivalents may be substituted for elements thereof without departing from the spirit and scope of the embodiments. In addition, while a particular feature may have been disclosed with respect to only one of several implementations, such feature may be combined with one or more other features of the other implementations as may be desired and advantageous for any given or particular application. Furthermore, many modifications may be made to adapt a particular situation or material to the teachings of the embodiments without departing from the scope thereof.

Further, the purpose of the foregoing Abstract is to enable the U.S. Patent and Trademark Office and the public generally and especially the scientists, engineers and practitioners in the relevant art(s) who are not familiar with patent or legal terms or phraseology, to determine quickly from a cursory inspection the nature and essence of this technical disclosure. The Abstract is not intended to be limiting as to the scope of the present disclosure in any way.

Therefore, the breadth and scope of the subject matter provided herein should not be limited by any of the above explicitly described embodiments. Rather, the scope of the embodiments should be defined in accordance with the following claims and their equivalents.

What is claimed is:
1. An implant device comprising:
  a connection bridge to cause retraction or distraction of first and second bone segments of a bone, the connection bridge mountable to overlap an outer surface of the bone and configured to, in at least one plane, exert a force of retraction or distraction to one of the first and second bone segments in response to translational motion of the connection bridge and includes:
a first insertion structure mountable to in overlapping relationship with an outer surface of the first bone segment, the first insertion structure having at least one rack;
an internal repositioning tool having a pinion to engage the at least one rack to cause the translational motion;
a lock mechanism to selectively lock the translational motion of the repositioning tool; and
a second insertion structure mountable to in overlapping relationship with an outer surface of the second bone segment or a third bone segment between the first bone segment and the second bone segment, the second insertion structure includes a housing to:
internally house at least one of the pinion and the lock mechanism; and
receive a portion of the at least one rack of the first insertion structure within the housing to engage the at least one of the pinion and the lock mechanism,
wherein:
the lock mechanism comprises a ratchet;
the at least one rack comprises a ratchet rack; and
the ratchet comprises:
a first spring including a first arm having a first ratchet prong at a first end of the first arm, the first ratchet prong to engage a first rack portion of the ratchet rack;
a second spring including a second arm having a second ratchet prong at a first end of the second arm, the second ratchet prong to engage a second rack portion of the ratchet rack;
a first indentation in the first arm; and
a second indentation in the second arm.

2. The implant device of claim 1, wherein the at least one rack is a dual-purpose rack to both engage the pinion and the lock mechanism.

3. The implant device of claim 1, wherein:
the second insertion structure includes the pinion; and
the second insertion structure further comprises a keyhole to the pinion to selectively apply at least one of:
a first force of torque in a first direction, to cause the pinion to rotate in a first rotation direction along the at least one rack; and
a second force of torque in a second direction, to cause the pinion to rotate in a second rotation direction along the at least one rack and the first rotation direction and the second rotation direction are opposite rotation directions.

4. The implant device of claim 3, wherein the at least one rack has one of a linear configuration and a curved configuration.

5. The implant device of claim 1, wherein the second insertion structure further comprises a slide switch to simultaneously lock or unlock both the first ratchet prong in the first rack portion and the second ratchet prong in the second rack portion.

6. The implant device of claim 5, wherein:
the slide switch includes a slide channel in which to slide the slide switch between a first position and a second position;
sliding the slide switch to the first position causes the slide switch to engage the first arm and second arm such that the first arm and the second arm simultaneously move away from each other to expand a distance therebetween and engage the first ratchet prong in a first recess in the first rack portion and engage the second ratchet prong in a second recess in the second rack portion; and
sliding the slide switch to the second position causes the slide switch to engage the first arm and second arm such that the first arm and the second arm simultaneously move toward each other to reduce a distance therebetween and disengage the first ratchet prong from the first recess in the first rack portion and disengage the second ratchet prong from the second recess in the second rack portion.

7. The implant device of claim 1, further comprising:
a built-in adjustment tool having a handle, the adjustment tool includes:
a built-in handle mounted to the connection bridge; and
an interface at one end of the handle coupled to the repositioning tool, such that rotation of the built-in handle causes the translational motion.

8. An osseous repair system, comprising:
the implant device of claim 1;
a plurality of fasteners to fasten the implant device to an outer surface of a first bone segment and an outer surface of a second bone segment; and
a tool to interface with the implant device to cause translational motion of at least one of the first insertion structure of the implant device relative to the second insertion structure of the implant device to adjust a distance between the first bone segment and the second bone segment.

9. The osseous repair system of claim 8, wherein the translational motion is in one of a linear direction and a curved direction and configured to be locked by locking the first insertion structure to the second insertion structure.

10. The osseous repair system of claim 8, wherein the implant device includes a third insertion structure, the tool to cause translational motion of the third insertion structure of the implant device relative to the second insertion structure to adjust the distance between the first bone segment and the second bone segment.

11. The osseous repair system of claim 10, wherein:
the translational motion of the third insertion structure is in one of a linear direction and a curved direction and configured to be locked by locking the first insertion structure to the second insertion structure; and
the second insertion structure is mounted to a third bone segment between the first bone segment and the second bone segment.

12. The osseous repair system of claim 10, wherein:
the tool is built-in to the implant device.

13. A method, comprising:
fastening the implant device of claim 1, to a first bone segment and a second bone segment by a first tool used by a surgeon;
causing translational motion of the first insertion structure of the implant device relative to the second insertion structure of the implant device to adjust a distance between the first bone segment and the second bone segment using a second tool interfaced to the implant device; and
during the causing of the translational motion, causing one of retraction and distraction of the first bone segment relative to the second bone segment using the implant device to treat a condition of at least one bone having the first bone segment and the second bone segment, wherein the implant device includes a fixed distance defined by teeth pitch of a rack of teeth for predetermined measured growth in a direction associated with the translational motion.

14. The method of claim 13, wherein the translational motion is in a linear direction or a curved direction.

15. The method of claim 13, further comprising:
during the translational motion, causing translation motion of a third insertion structure of the implant device relative to the second insertion structure.

16. The method of claim 15, wherein:
during the translational motion of the first insertion structure relative to the second insertion structure, the second insertion structure is mounted to a third bone segment between the first bone segment and the second bone segment; and
during the translation motion of the third insertion structure relative to the second insertion structure, the third insertion structure is mounted to the second bone segment and the second insertion structure is mounted to the third bone segment.

17. The method of claim 13, further comprising:
prior to fastening the implant device, using a virtual surgical planning tool to design the implant device using before and after bone segment positions of an image of the bone segments to define a path for the translational motion.

18. An implant device comprising:
a connection bridge to cause retraction or distraction of first and second bone segments of a bone, the connection bridge mountable to overlap an outer surface of the bone and configured to, in at least one plane, exert a force of retraction or distraction to one of the first and second bone segments in response to translational motion of the connection bridge and includes:
a first insertion structure mountable to in overlapping relationship with an outer surface of the first bone segment, the first insertion structure having at least one rack;
an internal repositioning tool having a pinion to engage the at least one rack to cause the translational motion;
a lock mechanism to selectively lock the translational motion of the repositioning tool; and
a second insertion structure mountable to in overlapping relationship with an outer surface of the second bone segment or a third bone segment between the first bone segment and the second bone segment, the second insertion structure includes a housing to:
internally house at least one of the pinion and the lock mechanism; and
receive a portion of the at least one rack of the first insertion structure within the housing to engage the at least one of the pinion and the lock mechanism,
wherein:
the second insertion structure is configured to be mounted to in overlapping relationship with an outer surface of the third bone segment;
the connection bridge further comprises a third insertion structure mountable to in overlapping relationship with the second bone segment, the third insertion structure includes at least one rack having a rack portion insertable into the second insertion structure to engage the pinion; and
the internal repositioning tool is configured to cause translational motion of the first and third insertion structures.

19. The implant device of claim 18, wherein:
the least one rack of the first insertion structure has one of a first linear configuration and a first curved configuration; and
the least one rack of the third insertion structure has one of a second linear configuration and a second curved configuration.

* * * * *